(12) United States Patent
Aguilera et al.

(10) Patent No.: US 9,999,499 B2
(45) Date of Patent: Jun. 19, 2018

(54) PRELOADED INTRAOCULAR LENS (IOL) SYSTEM AND METHOD

(71) Applicant: Aaren Scientific, Inc., Ontario, CA (US)

(72) Inventors: Rick Aguilera, Rancho Cucamonga, CA (US); Bob Glick, Trabuco Canyon, CA (US); Stephen Q. Zhou, Irvine, CA (US)

(73) Assignee: Carl Zeiss Meditec Production, LLC, Ontario, CA (US)

(*) Notice: Subject to any disclaimer, the term of this patent is extended or adjusted under 35 U.S.C. 154(b) by 91 days.

(21) Appl. No.: 13/840,435

(22) Filed: Mar. 15, 2013

(65) Prior Publication Data

US 2014/0066946 A1    Mar. 6, 2014

Related U.S. Application Data

(60) Provisional application No. 61/696,545, filed on Sep. 4, 2012.

(51) Int. Cl.
*A61F 2/06* (2013.01)
*A61F 2/16* (2006.01)

(52) U.S. Cl.
CPC ............ *A61F 2/1662* (2013.01); *A61F 2/167* (2013.01); *A61F 2/1678* (2013.01); *A61F 2/1691* (2013.01)

(58) Field of Classification Search
CPC ...... A61F 2/1662; A61F 2/167; A61F 2/1691; A61F 2/1664; A61F 2/1667; A61F 2/16;
(Continued)

(56) References Cited

U.S. PATENT DOCUMENTS 4,863,464 A * 9/1989 Dusek ................... 623/6.55
5,474,562 A * 12/1995 Orchowski et al. ...... 606/107
(Continued)

FOREIGN PATENT DOCUMENTS

EP    0688183 B1   10/2002
RU    2375992 C2    8/2009
(Continued)

OTHER PUBLICATIONS

Mamalis, Nick et al., "Hydrophobic Acrylic Oils: A Primer", Mar. 2011. Cataract & Refractive Surgery Today Europe. pp. 39-44.*
(Continued)

*Primary Examiner* — Elizabeth Houston
*Assistant Examiner* — Mohamed Gabr
(74) *Attorney, Agent, or Firm* — Walter Ottesen, P.A.

(57) ABSTRACT

A preloaded intraocular lens (IOL) system/method utilizing haptic compression is disclosed. The disclosed system/method utilizes an IOL packaged in a compressed state that is inserted into a patient using a cartridge and lumen through which the IOL is advanced. Within this context the haptics to the IOL are wrapped around the IOL in a coplanar fashion during the loading of the IOL to permit the IOL to be shipped and stored in a compressed state. This compressed state is achieve by wrapping the haptics of the IOL during the manufacturing process to ensure that the IOL is properly aligned and thus delivered in a predetermined orientation within the patient's eye. This compressed packaging of the IOL permits a more uniform and consistent placement of the IOL in the patient and eliminates the potential for physician error during the critical IOL placement procedure.

60 Claims, 64 Drawing Sheets

(58) Field of Classification Search
CPC .... A61F 2/1675; A61F 2/1613; A61F 2/1678; A61F 2/164; A61F 2/1648; A61F 2002/1681; A61F 2002/1683; A61F 2002/16965; A61F 9/00834; B29D 11/023; G02B 1/041
USPC ............ 606/107; 623/6.12, 6.23, 6.34, 6.56; 526/279, 320
See application file for complete search history.

(56) References Cited

U.S. PATENT DOCUMENTS

| | | | |
|---|---|---|---|
| 5,499,987 | A | 3/1996 | Feingold |
| 7,422,604 | B2 | 9/2008 | Vaquero et al. |
| 8,858,625 | B2 | 10/2014 | Putallaz et al. |
| 2004/0042073 | A1 | 3/2004 | Pynson |
| 2005/0049606 | A1 | 3/2005 | Vaquero et al. |
| 2006/0142781 | A1 | 6/2006 | Pynson et al. |
| 2006/0167466 | A1 | 7/2006 | Dusek |
| 2006/0276606 | A1* | 12/2006 | Benz et al. ............... 526/320 |
| 2008/0058830 | A1 | 3/2008 | Cole et al. |
| 2008/0097460 | A1 | 4/2008 | Boukhny et al. |
| 2009/0318933 | A1* | 12/2009 | Anderson ............... 606/107 |
| 2010/0211170 | A1* | 8/2010 | Liao ............... 623/6.34 |
| 2010/0228345 | A1 | 9/2010 | Bille |
| 2014/0378987 | A1 | 12/2014 | Putallaz et al. |

FOREIGN PATENT DOCUMENTS

| | | |
|---|---|---|
| WO | 2007/037689 A2 | 4/2007 |
| WO | 2010144318 A1 | 12/2010 |

OTHER PUBLICATIONS

International Preliminary Report on Patentability and Written Opinion dated Mar. 19, 2015 of corresponding international application PCT/US2013/057100.

Translation of Chinese Office Action of Chinese Patent Office dated Dec. 16, 2015 of corresponding Chinese application 201380057654.1.

Supplementary European Search Report of European Patent Office dated Mar. 22, 2016 of corresponding European application 13834652.

Extended European Search Report of European Patent Office dated Apr. 1, 2016 of corresponding European application 13834652.

Translation of Notice of Reason for Refusal issued by Japanese Patent Office dated Jun. 6, 2017.

English Translation of Second Office Action from Chinese Patent Office dated Oct. 10, 2016 in corresponding patent application 201380057654.1 filed Aug. 28, 2013.

First Office Action from Australian Patent Office dated Nov. 14, 2016 in corresponding patent application 2013313118.

Search Report issued by Chinese Patent Office dated Mar. 17, 2017 in corresponding patent application 201380057654.1.

English Translation of Third Office Action from Chinese Patent Office dated Apr. 5, 2017 in corresponding patent application 201380057654.1 filed Aug. 28, 2013.

Translation of First Office Action issued by Russian Patent Office dated Jul. 26, 2017 of corresponding Russian application 2015112242.

\* cited by examiner

U.S. Patent Application Publication 2009/0318933

Aaren Scientific HPI System

Aaren Scientific HPI System

Prior Art

1900

*Prior Art*

2300

Prior Art

3000

Prior Art

3800

Prior Art

PRELOADED INTRAOCULAR LENS (IOL) SYSTEM AND METHOD

CROSS REFERENCE TO RELATED APPLICATIONS

This application claims benefit under 35 U.S.C. § 119 and incorporates by reference United States Provisional patent application for A PRELOAD SYSTEM FOR INTRAOCULAR LENS (IOL) UTILIZING HAPTIC COMPRESSION by inventors Rick Aguilera, Bob Glick, and Stephen Zhou, filed electronically with the USPTO on Sep. 4, 2012, with Ser. No. 61/696,545.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention relates to systems and methods associated with storage, manipulation, and insertion of intraocular lenses (IOLs) in patients. The present invention teaches a preloaded IOL system/method wherein the IOL may be loaded into the injector with its haptic bodies in compressed form to allow:
 the delivery of the IOL into a patient's eye with a predictable orientation of the IOL;
 a simplified system of loading of the IOL by the physician.

By way of example only, the present invention may have application in U.S. Patent Classifications 623/6, 623/6.12, and 606/107.

PRIOR ART AND BACKGROUND OF THE INVENTION

Overview

Intraocular lenses (IOL) have been widely used after a cataractous human lens is removed by a surgeon. Intraocular lenses are usually made of an optic body and haptic bodies. The optic body can be made from a rigid material, such as poly (methylmethacrylate) (PMMA), or flexible acrylic polymers or silicone. PMMA IOLs are rigid so it requires a large incision of about 6 mm on the cornea in order to be implanted into the eye. Recently, foldable IOLs have become very popular because they can be folded with the use of a cartridge ("cartridge") and then implanted through cornea into the eye with an incision size of about 2 to 3 mm. This cartridge is comprised of a lens loading portion that holds and folds the IOL and a lumen portion which has gradually decreasing dimensions through which the lens is delivered to an eye. To implant an IOL using such a cartridge, a surgeon or a nurse takes an IOL from a separate IOL package with a forceps and places the IOL into the cartridge (the "placement"). The cartridge is then closed and as a result of the closing the lens is folded into the desired configuration (the "folding"). After the folding, the IOL is injected into the eye by pushing the folded IOL through the lumen with a plunger of some design (the "injection"). Once the IOL is in the eye it is designed to recover to:
 its prior shape; and
 a predetermined orientation within the eye.

In this process, the placement is critical. If the placement is not done correctly the following may occur:
 the lens may be damaged by the folding or the injection; or
 upon injection the lens may not obtain the desired predetermined orientation inside the eye. If this happens, surgeon will need to use a tool to manually re-orientate the lens inside the eye. Obviously, this additional step not only makes the surgery longer, but also brings unnecessary risks of possible damage to the eye tissue by this manual maneuver, thus causing additional surgical trauma.

To obviate the above described risks it is desirable for a manufacturer of a Preloaded System to properly place the lens in the cartridge for the nurse or doctor in the manufacturing facility to avoid the potential for error in the placement. Considering the potential 3-5 years of shelf-life for IOLs, the literature has stated that it is not advisable to apply any stress, compression, or stretch on the IOL cartridge during the period of shelf-life time. The industry believes that if stress, compression, or stretch is exerted on the lens for an extended period of time these environmental factors may irreversibly deform the lens.

According to the existing technology in the prior art, the lens should rest in a lens holding station in a totally relaxed state. For example, U.S. Patent Application Publication 2009/0318933 discloses a Preloaded System which includes a handpiece with a holding station for placement of the IOL. The IOL is placed within the holding station during manufacturing in a relaxed state without compression or stretch of the lens body or its haptic body. The holding station desirably maintains the IOL in a relaxed configuration during storage. When the surgeon begins the injection process the natural contours of the lumen are used to gradually fold the lens into the appropriate configuration. This injection and folding step is conducted by a surgeon and usually only takes a few minutes to finish.

In another example, U.S. Pat. No. 7,422,604 (Vaquero) discloses a retainer which holds an IOL in an unstressed state. The IOL is held in place by a small removable retaining device. The retainer which holds the lens in an unstressed state is attached to an injector body and is sealed in the same package for delivery by a surgeon. To inject the IOL through the injector body, the retainer is removed from the injector body causing the IOL to become located in an unstressed state in the injector body. The IOL is folded and a plunger is advanced to push the IOL through and out the injector body tip and into the eye.

Deficiencies in the Prior Art

Prior art IOL systems require that the lens be transported and stored in a relaxed state, requiring that the physician exercise skill at the time of placement to ensure that the lens is delivered in a predictable orientation. If the lens is improperly oriented, the physician is required to manipulate the lens in some fashion after the lens has been injected into the eye. This manipulation increases the risk for damaging eye tissues, causing unnecessary additional surgical trauma.

Prior art IOL systems do not permit the IOL manufacturer to control the placement of the IOL in the cartridge or within the patient as this is determined in large part by the skill of the physician.

To date the prior art has not fully addressed these deficiencies.

OBJECTIVES OF THE INVENTION

Accordingly, the objectives of the present invention are (among others) to circumvent the deficiencies in the prior art and affect the following objectives:
(1) Provide for a preloaded IOL system and method that permits the IOL to be loaded, transported, and stored in a preloaded configuration. This system avoids manipulation of the IOL by the physician and thus reduces the potential for damage of the IOL during the physician manipulation process.
(2) Provide for a preloaded IOL system and method that permits the IOL to be loaded, transported, and stored with its haptic bodies in a compressed configuration to ensure that it is not damaged by the physician through improper loading prior to injection.
(3) Provide for a preloaded IOL system and method that permits the IOL to be loaded, transported, and stored with its haptic bodies in a compressed configuration to ensure that it is not damaged by the physician during the implantation process into the patient's eye.
(4) Provide for a preloaded IOL system and method that permits the IOL to be loaded, transported, and stored in a compressed configuration to ensure that its orientation is proper after the implantation into the patient's eye.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention pertains to a system, method, and product-by-process wherein an IOL may be stored in a compressed state and implanted into a patient's eye with predictable orientation by a physician. Once the lens is implanted inside the eye, the compressed haptic bodies recover back to their initial uncompressed state within minutes. The present invention discloses a Preloaded System which comprises:
An IOL which is packaged and stored with its haptic bodies in a compressed state;
An lens holding portion, such as the loading chamber of a cartridge;
A Lumen (such as the tube portion of a cartridge) through which the IOL is advanced; and
An injector body including a plunger which advances the lens from the lens holding portion through the lumen into a patient's eye.

The difference between the disclosed invention and the existing prior art technology is that the haptics to the IOL are wrapped around the lens optic body in a coplanar manner during the loading process and thus the IOL is stored in a compressed state (the "wrapping"). The wrapped IOL can be delivered into the patient's eye in a predictable orientation within the eye. As a result of wrapping, the IOL is consistently delivered into the eye with the haptic bodies in a coplanar fashion with the optic body. The coplanar delivery is very important because it insures that the IOL is consistently delivered in the desired predetermined orientation. Prior art preloaded IOL delivery systems do not contain an IOL which has been stored in a compressed state. On the contrary, many prior art literatures teach a preload system containing an IOL in an unstressed relaxed state.

BRIEF DESCRIPTION OF THE DRAWINGS

For a fuller understanding of the advantages provided by the invention, reference should be made to the following detailed description together with the accompanying drawings wherein.

Figure 1:
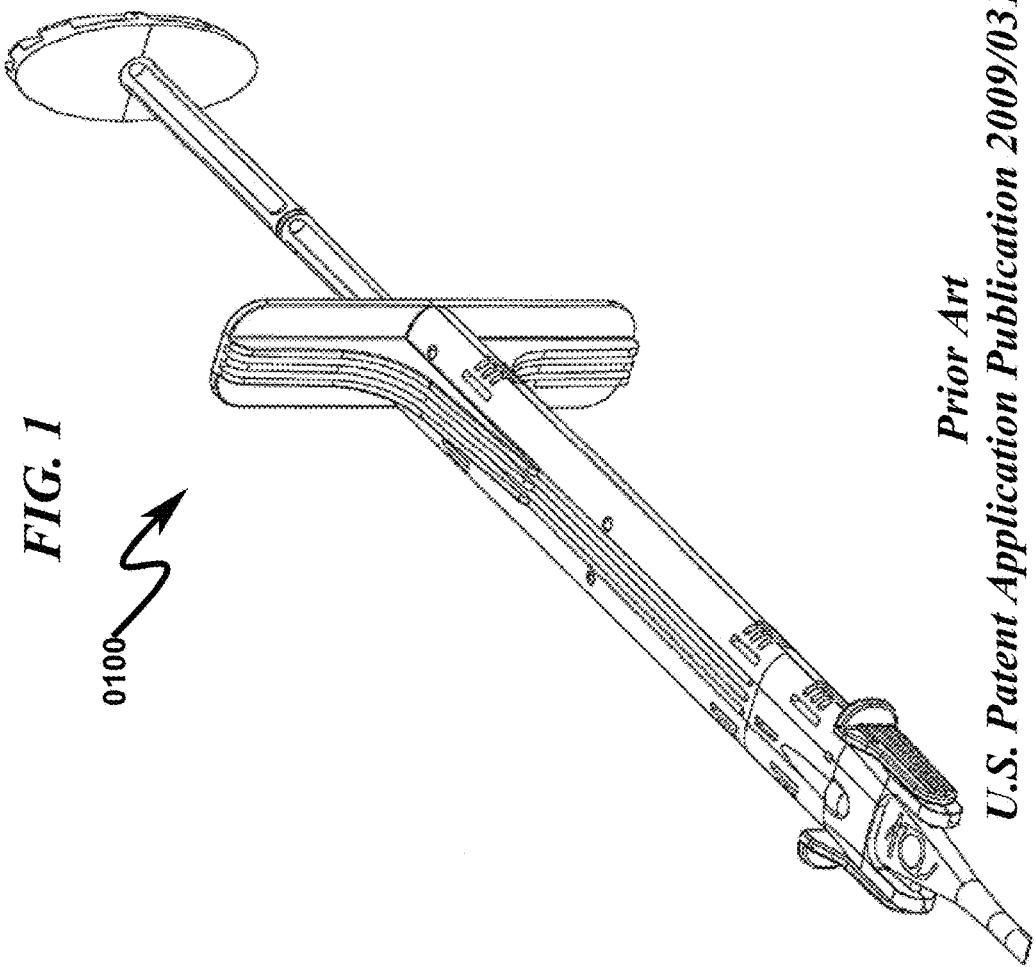
FIG. 1 illustrates a perspective view of a prior art preloaded intraocular lens cartridge as taught by United States Patent Application Publication 2009/0318933.
Figure 2:
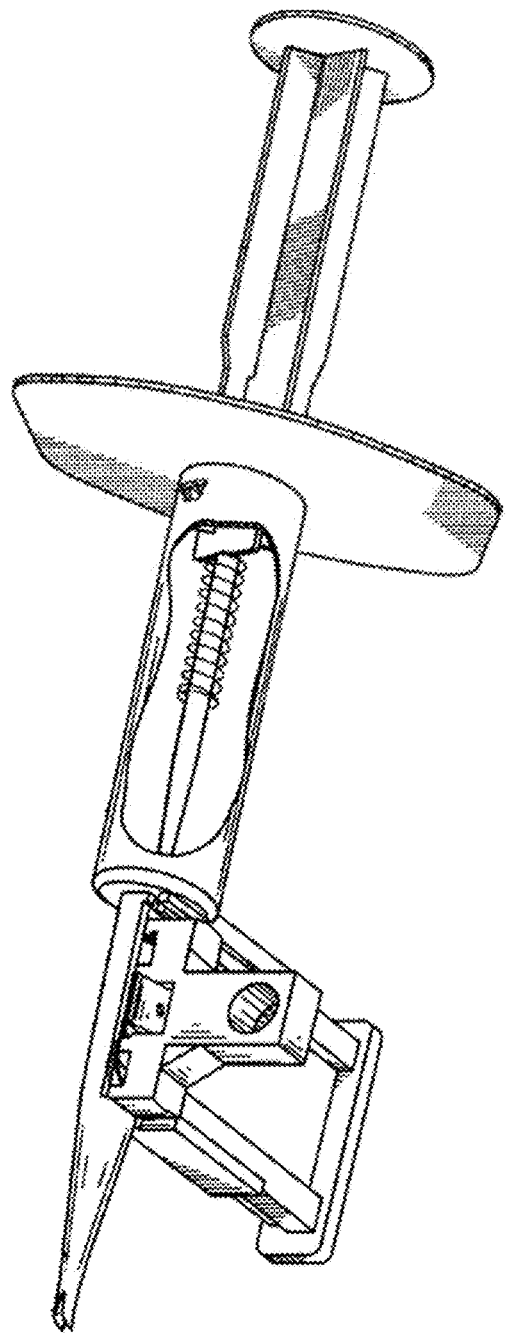
FIG. 2 illustrates a perspective view of a prior art preloaded intraocular lens cartridge as taught by U.S. Pat. No. 7,422,604.

DESCRIPTION OF THE PRESENTLY
PREFERRED EXEMPLARY EMBODIMENTS

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of a PRELOADED INTRAOCULAR LENS (IOL) SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Intraocular Lens (IOL) not Limitive

The present invention may be advantageously applied to the construction of dynamically adjustable optical lenses incorporating a wide range of materials. The mechanisms of incorporation of a wide variety of materials within the optical lens are not limited by the present invention. Therefore, the terms "intraocular lens", "lens", "(IOL)" and their equivalent construction embodiments should be given the broadest possible meaning within this context.

Preloaded System not Limitive

Figure 17:
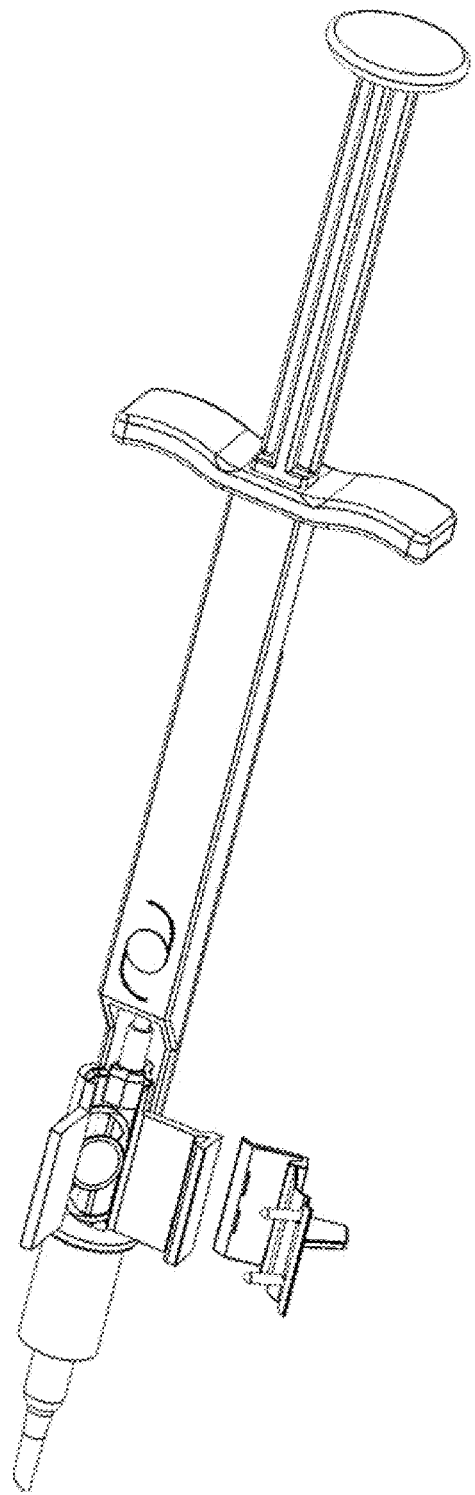
FIG. 17 illustrates a top perspective view of a prior art IOL preload system assembly.
Figure 18:
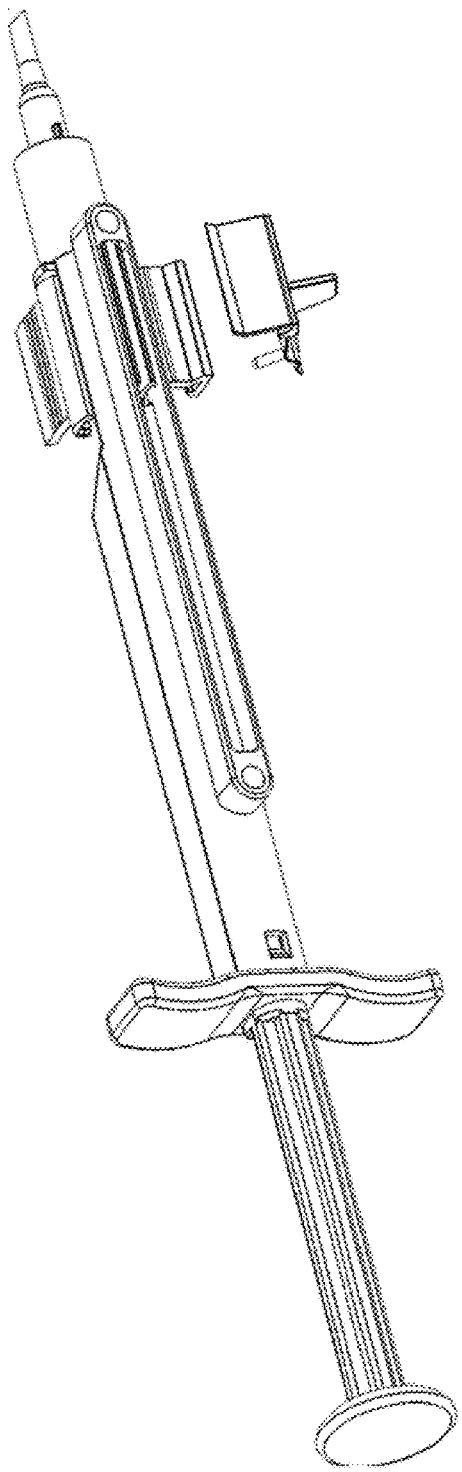
FIG. 18 illustrates a bottom perspective view of a prior art IOL preload system assembly.
Figure 19:
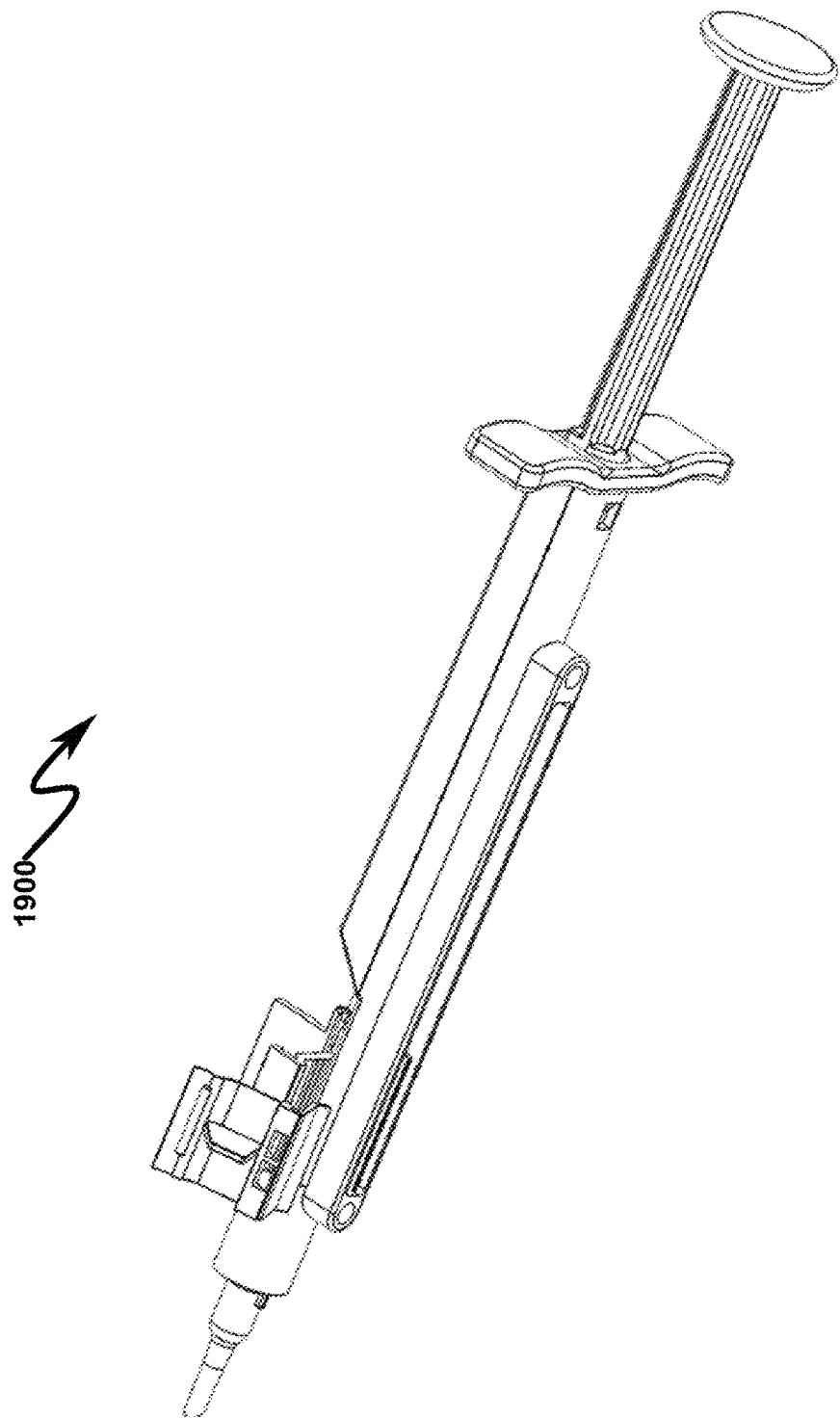
FIG. 19 illustrates a side perspective view of a prior art IOL preload system assembly.
Figure 20:
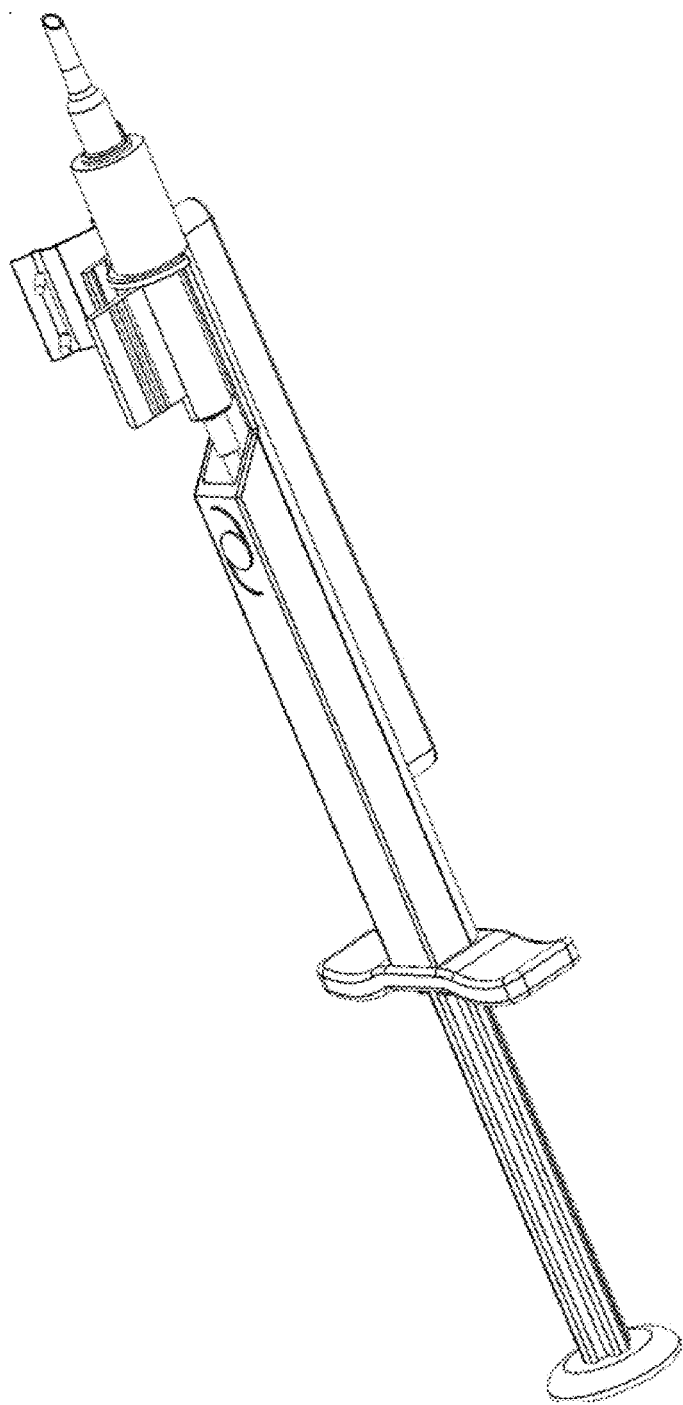
FIG. 20 illustrates a side perspective view of a prior art IOL preload system assembly.
Figure 21:
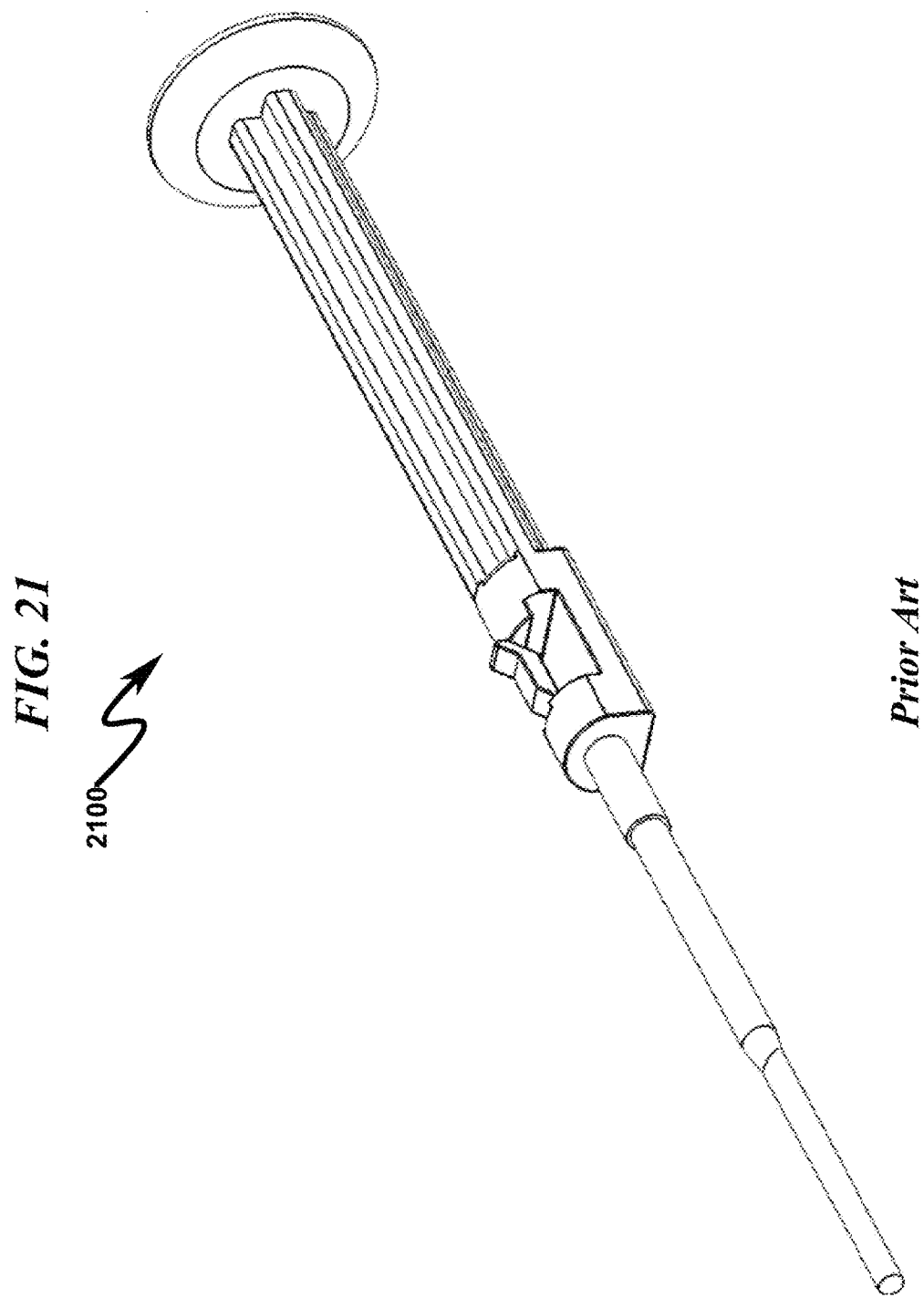
FIG. 21 illustrates a top perspective view of a prior art IOL preload plunger.
Figure 22:
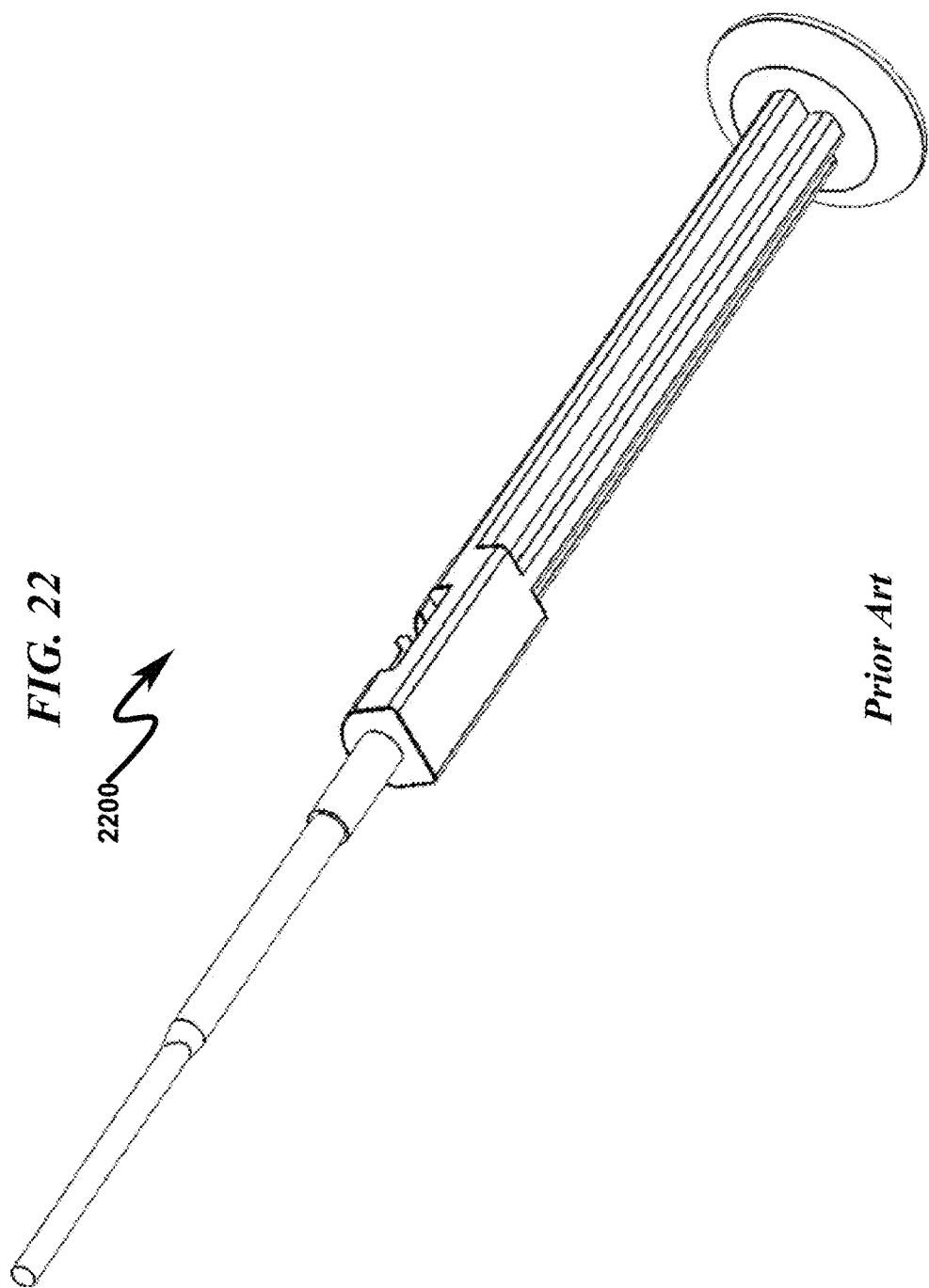
FIG. 22 illustrates a bottom perspective view of a prior art IOL preload plunger.
Figure 23:
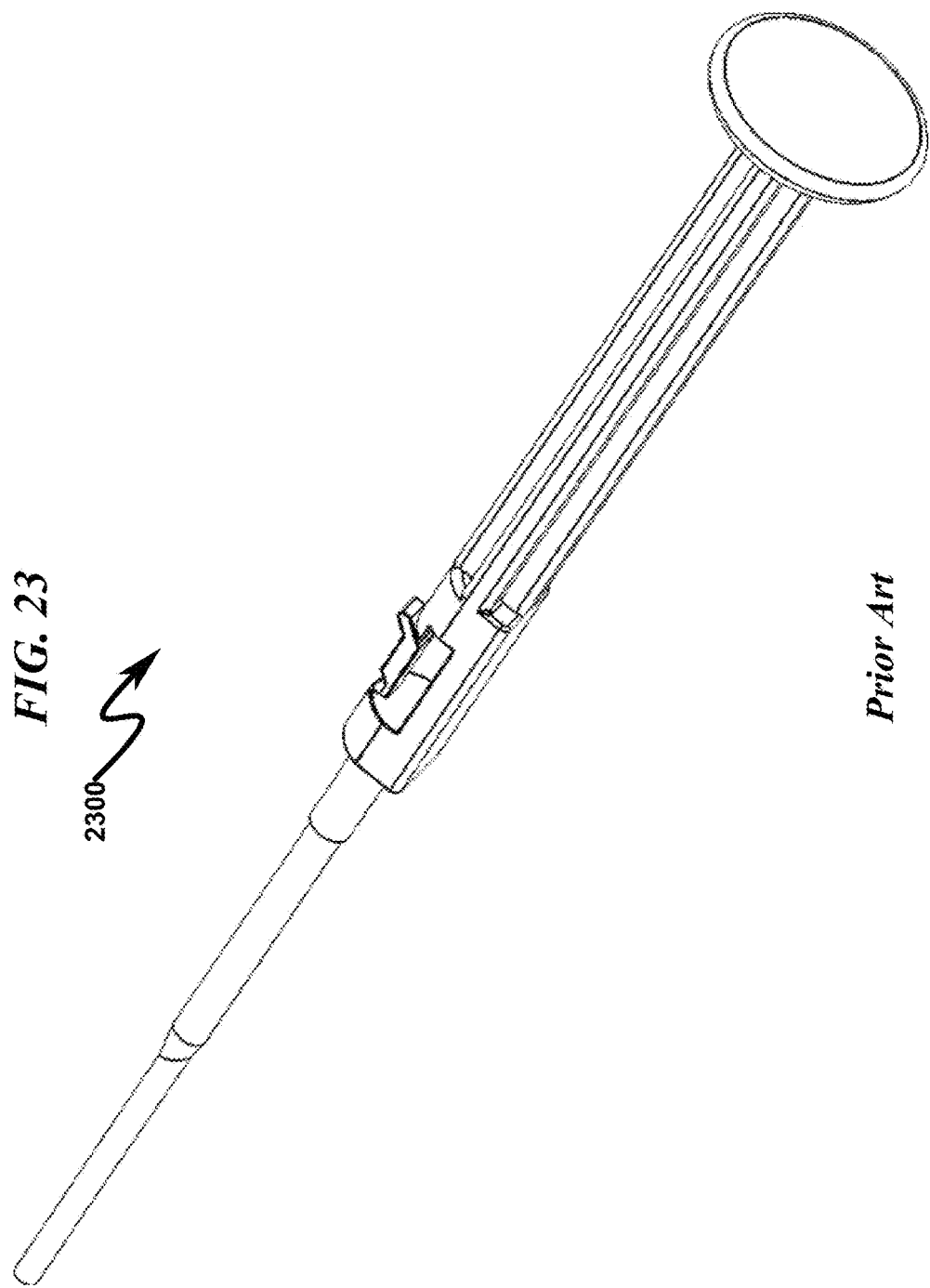
FIG. 23 illustrates a side perspective view of a prior art IOL preload plunger.
Figure 24:
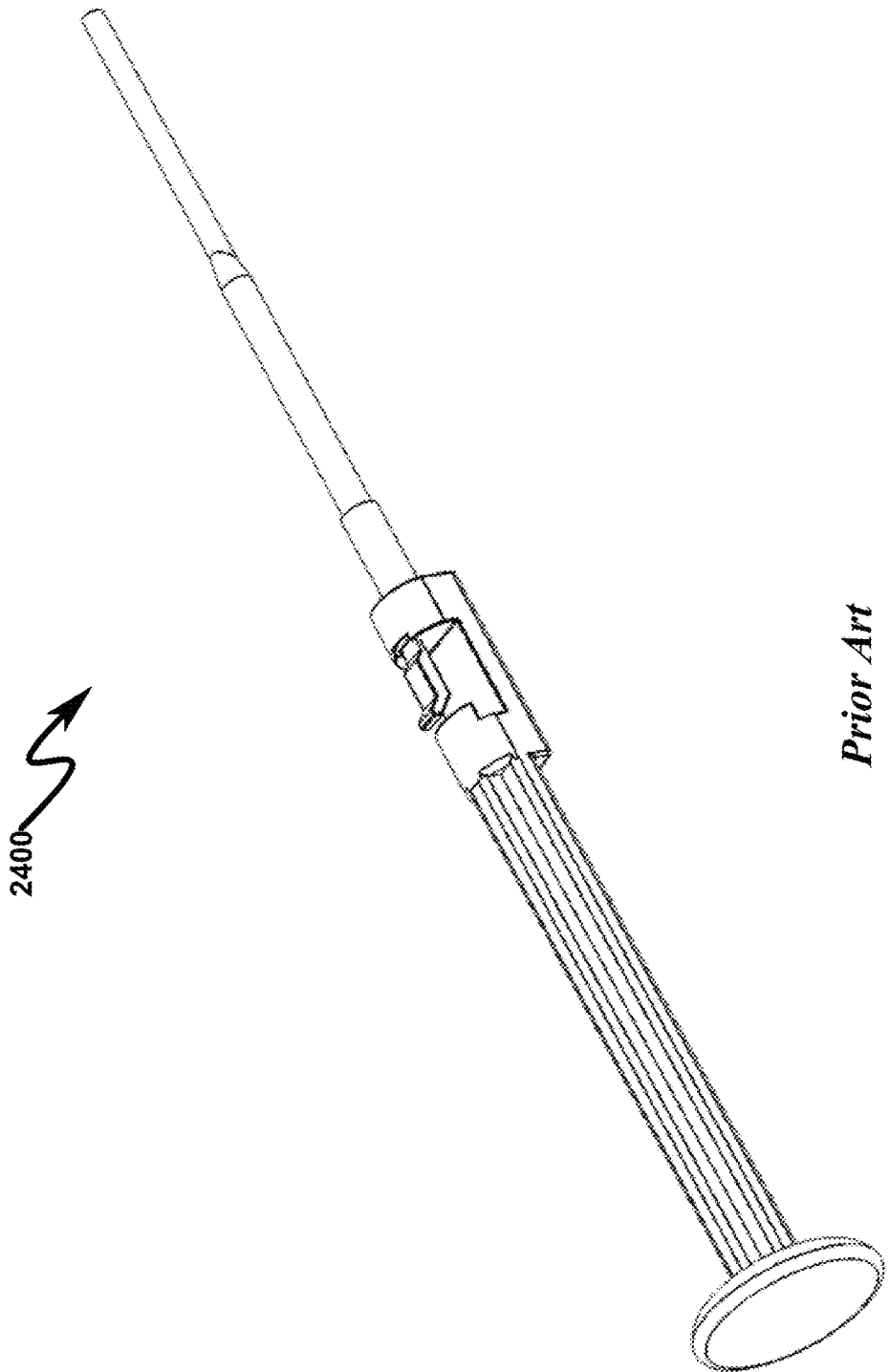
FIG. 24 illustrates a side perspective view of a prior art IOL preload plunger.
Figure 25:
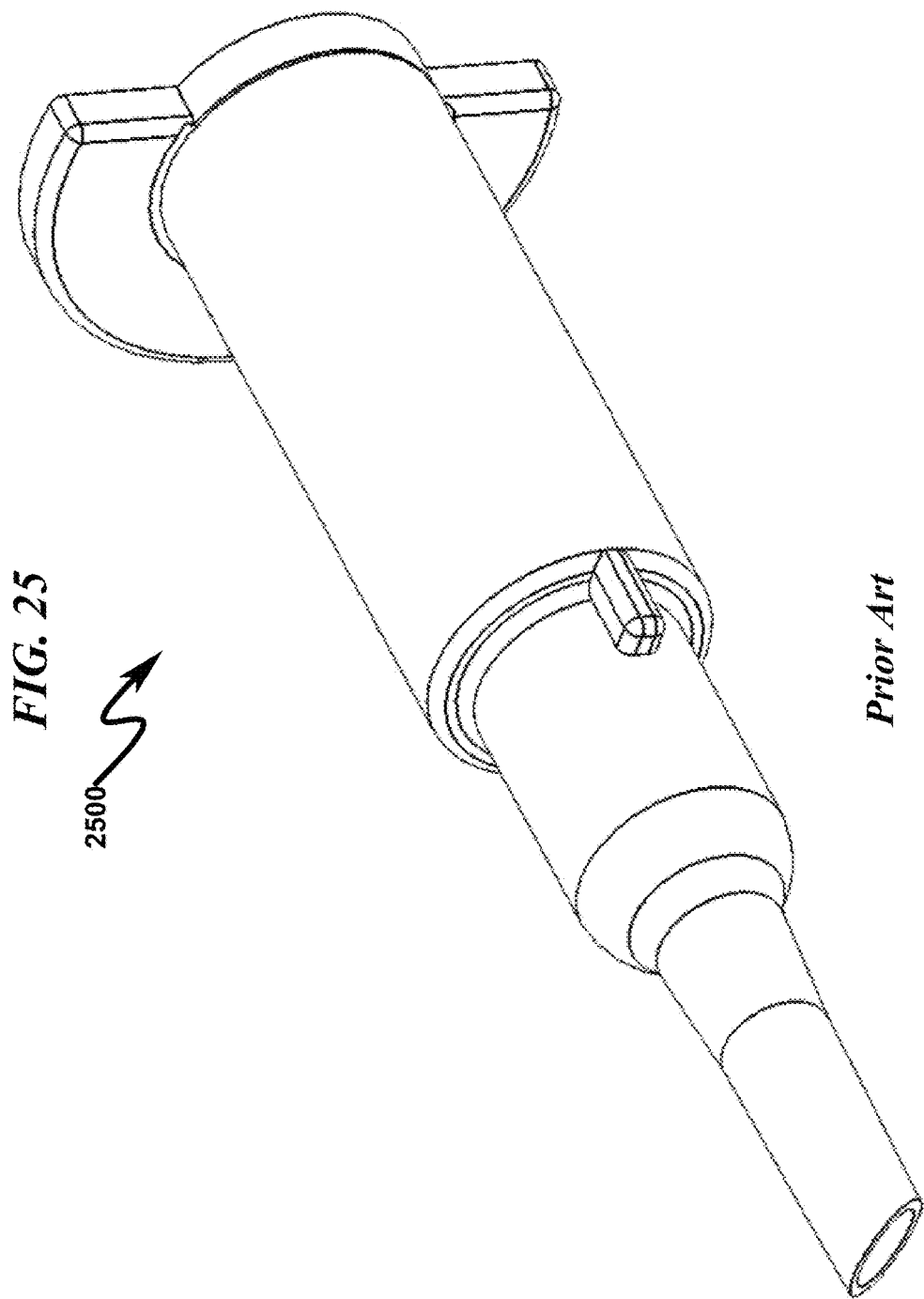
FIG. 25 illustrates a top perspective view of a prior art IOL preload lumen.
Figure 26:
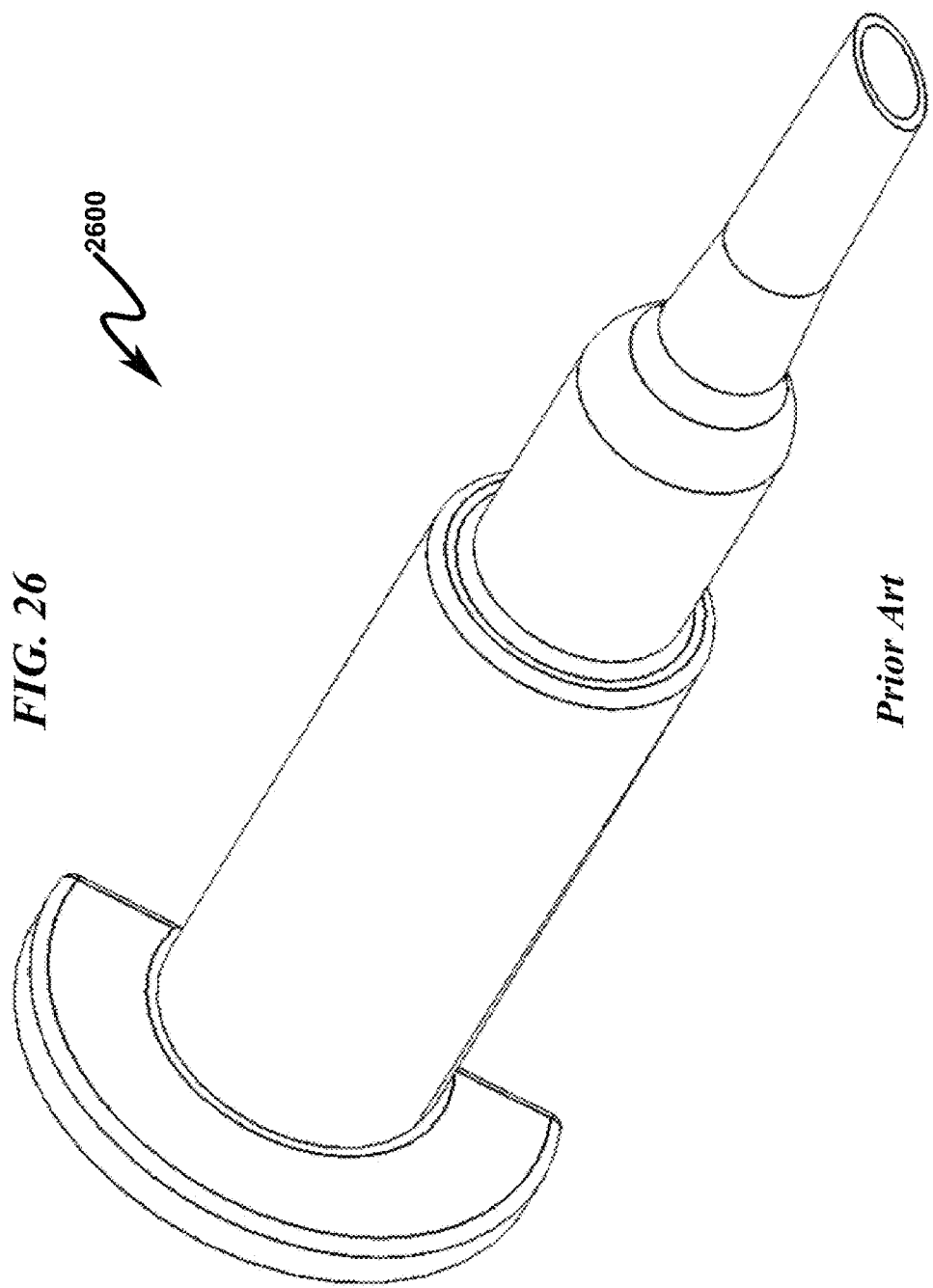
FIG. 26 illustrates a bottom perspective view of a prior art IOL preload lumen.
Figure 27:
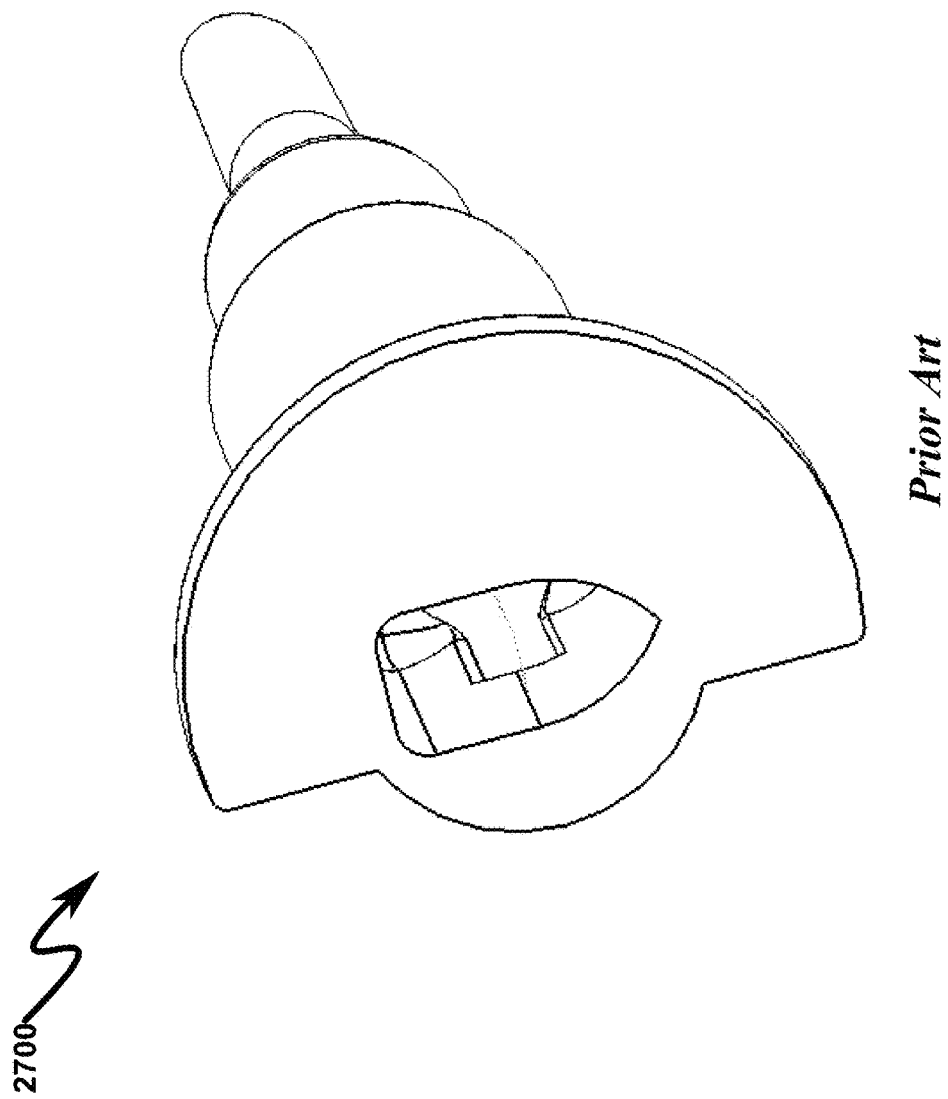
FIG. 27 illustrates an end perspective view of a prior art IOL preload lumen.
Figure 28:
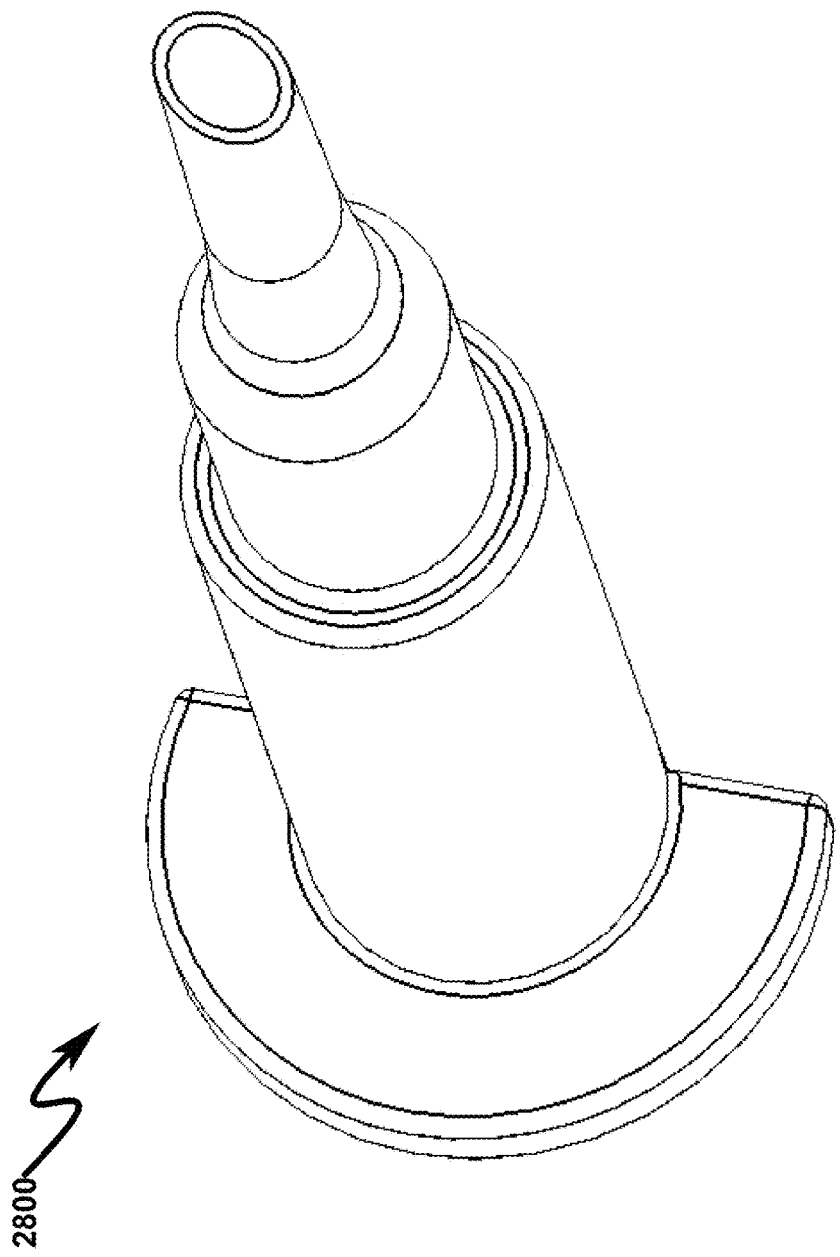
FIG. 28 illustrates a distal end perspective view of a prior art IOL preload lumen.
Figure 29:
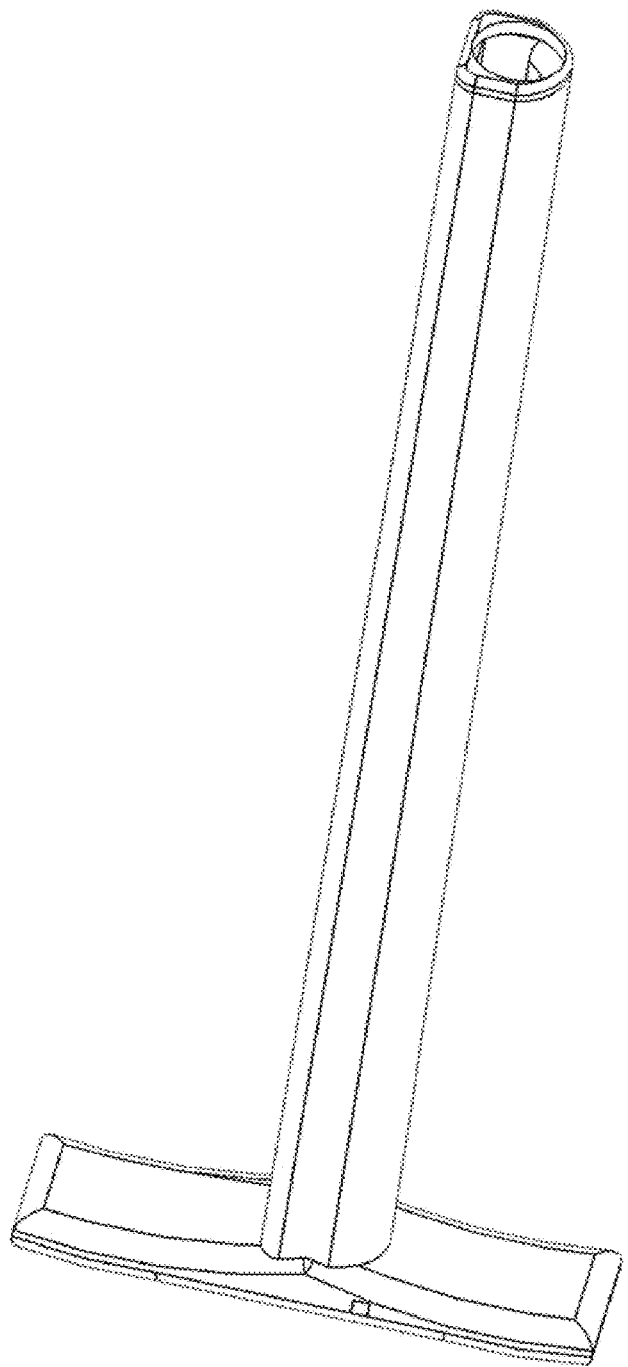
FIG. 29 illustrates a top perspective view of a prior art IOL preload handle body.
Figure 30:
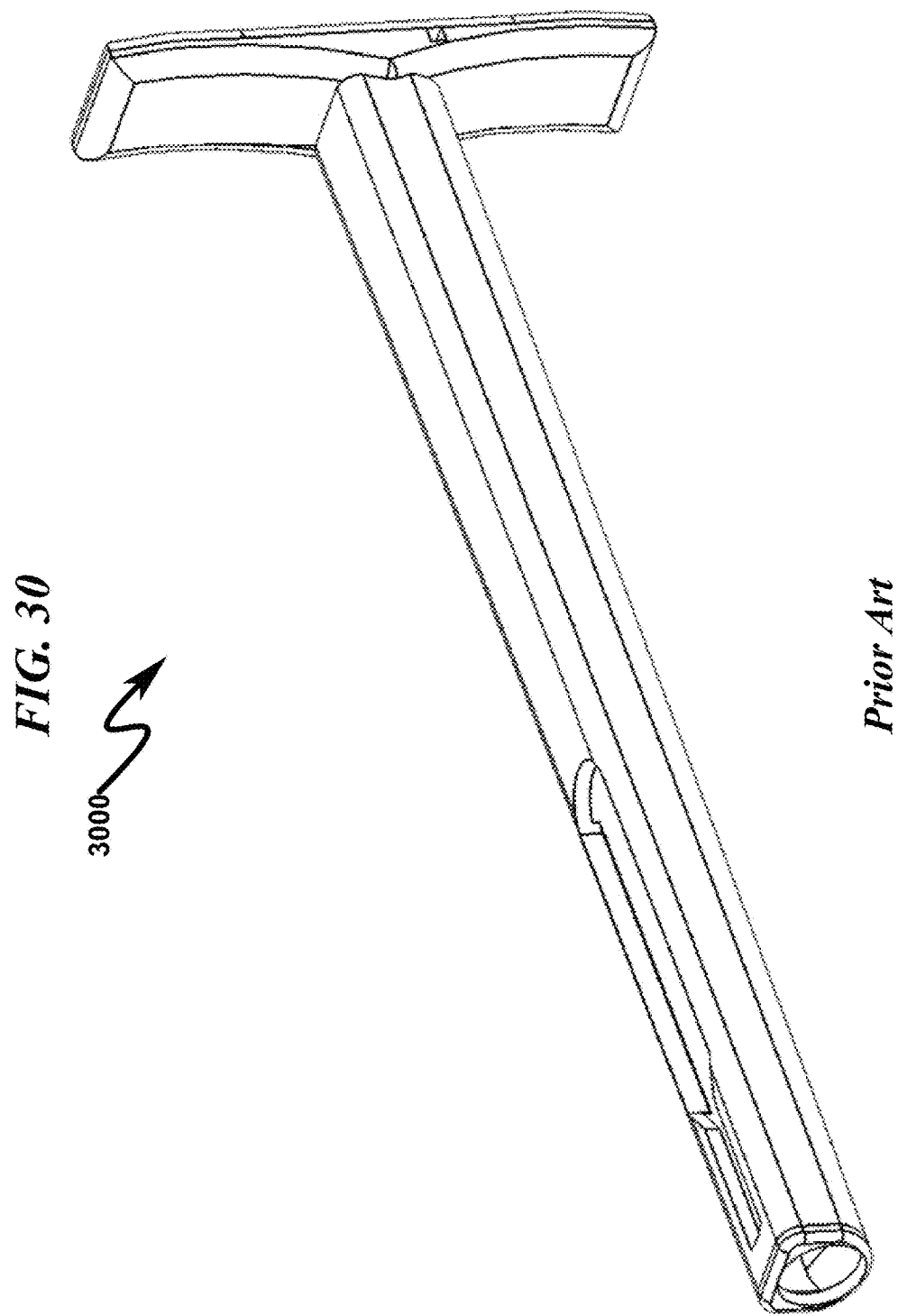
FIG. 30 illustrates a bottom perspective view of a prior art IOL preload handle body.
Figure 31:
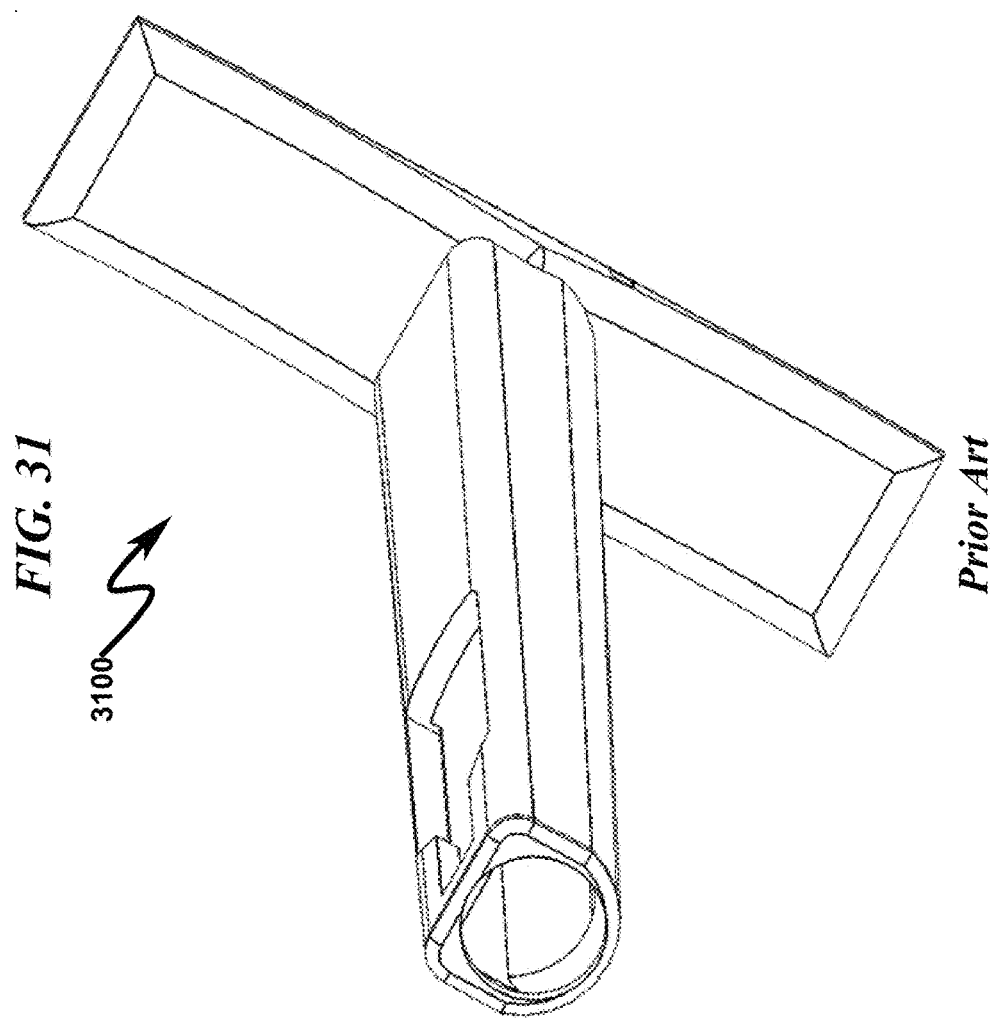
FIG. 31 illustrates a distal end perspective view of a prior art IOL preload handle body.
Figure 32:
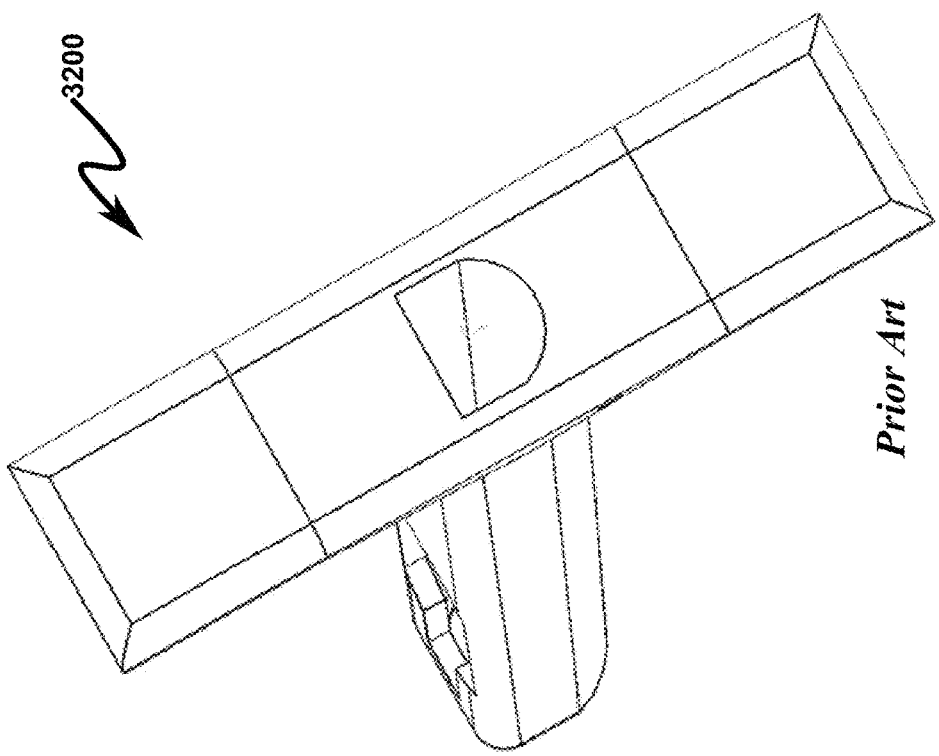
FIG. 32 illustrates a handle end perspective view of a prior art IOL preload handle body.

Within the context of the present invention scope, the term "preloaded IOL system" and its derivatives shall be defined to comprise:
  injector;
  cartridge; and
  lens;
such as depicted in FIG. 17 (1700), or in some circumstance may be defined to comprise:
  injector;
  lens holding chamber;
  lumen; and
  lens;
such as depicted in FIG. 1 (0100) wherein there is no separate cartridge. As the lens passes through lumen, it changes shape into a small profile and out from the distal opening end.

Prior Art Operational Overview (0300)-(0800)

Figure 3:
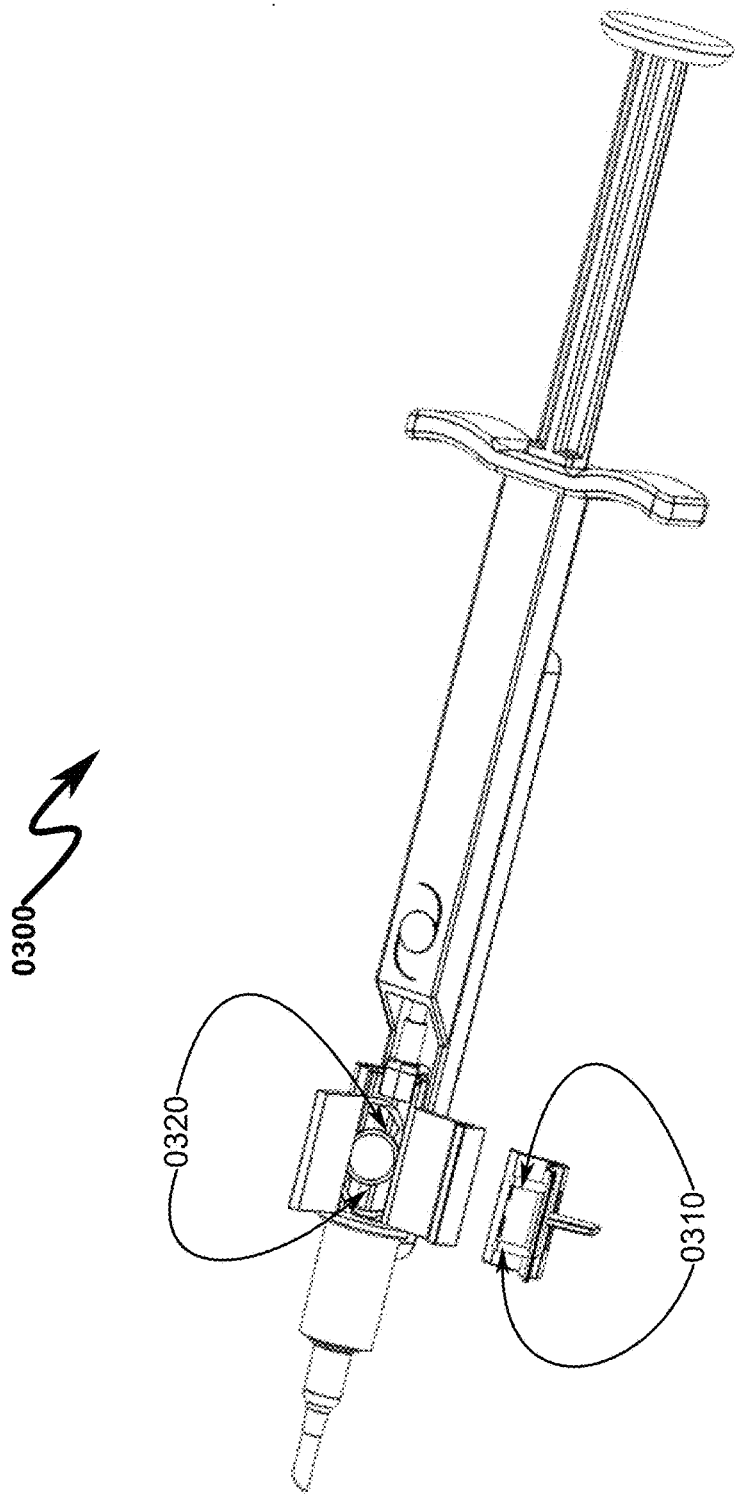
FIG. 3 illustrates a perspective view of a prior art preloaded intraocular lens cartridge as taught by AAREN SCIENTIFIC'S High Precision Injector (HPI) system.
Figure 4:
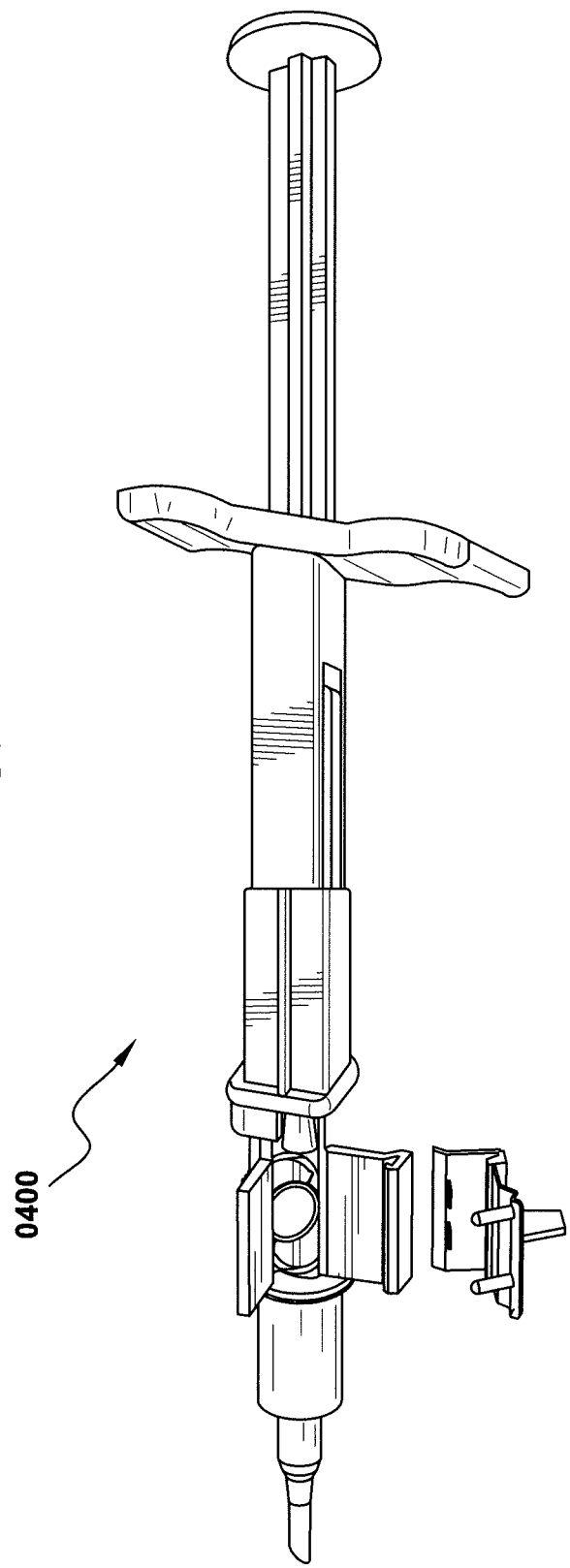
FIG. 4 illustrates a perspective view of a prior art preloaded intraocular lens cartridge as taught by AAREN SCIENTIFIC'S High Precision Injector (HPI) system, detailing the IOL and haptics.

A typical prior art IOL typically consists of:
  an optical body of approximately 6 mm; and
  haptic bodies with an overall diameter from haptic-to-haptic in the range of 12 to 13 mm.
In a typical Preload System, the IOL is positioned in the loading chamber with its optic body and haptic bodies totally relaxed, i.e. without compress or stretch. An example of such a preload system is AAREN SCIENTIFIC'S High Precision Injector (HPI) system, as generally shown in FIG. 3 (0300)-FIG. 4 (0400).

Figure 5:
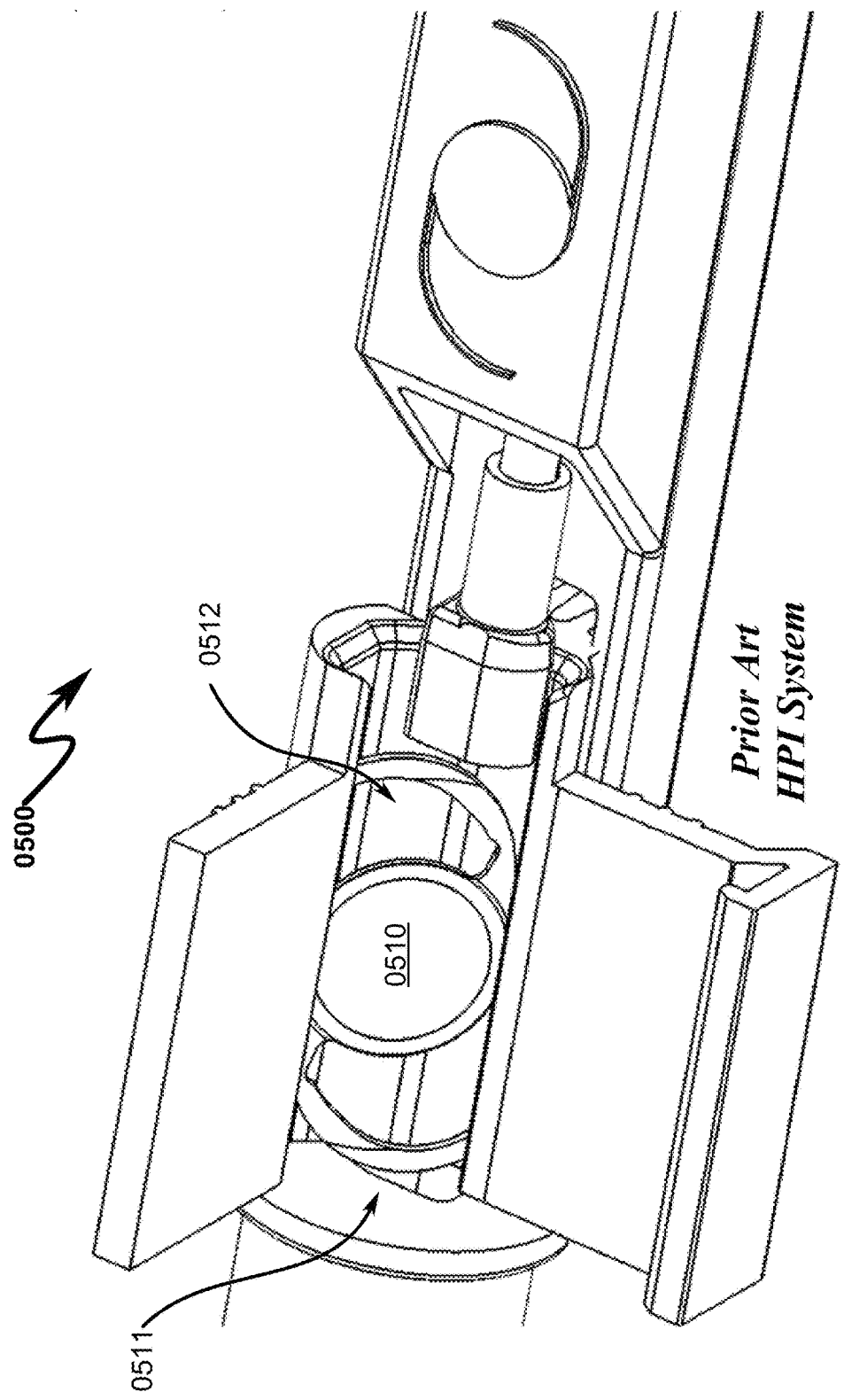
FIG. 5 illustrates a perspective view of a prior art preloaded intraocular lens cartridge as taught by AAREN SCIENTIFIC'S High Precision Injector (HPI) system, detailing the IOL and haptics.
Figure 6:
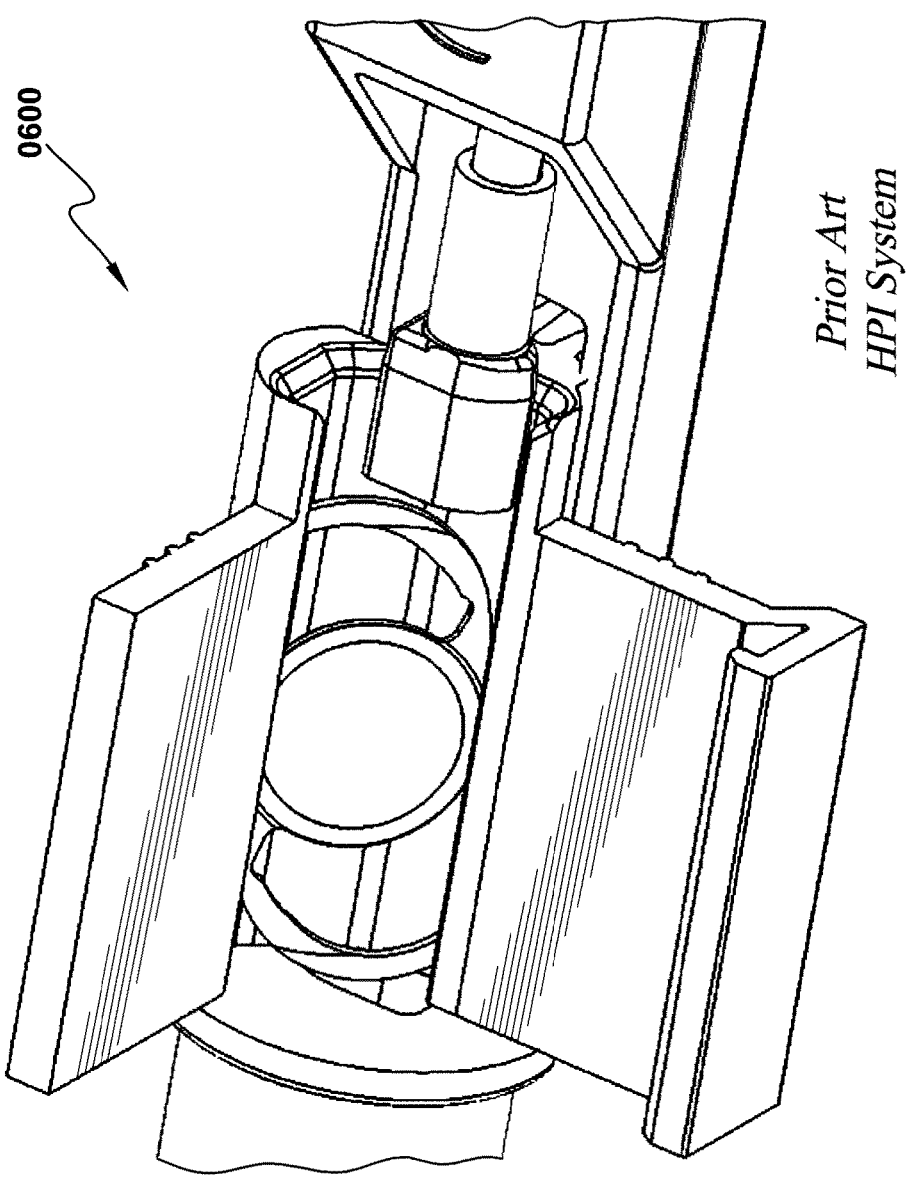
FIG. 6 illustrates a perspective view of a prior art preloaded intraocular lens cartridge as taught by AAREN SCIENTIFIC'S High Precision Injector (HPI) system.
Figure 7:
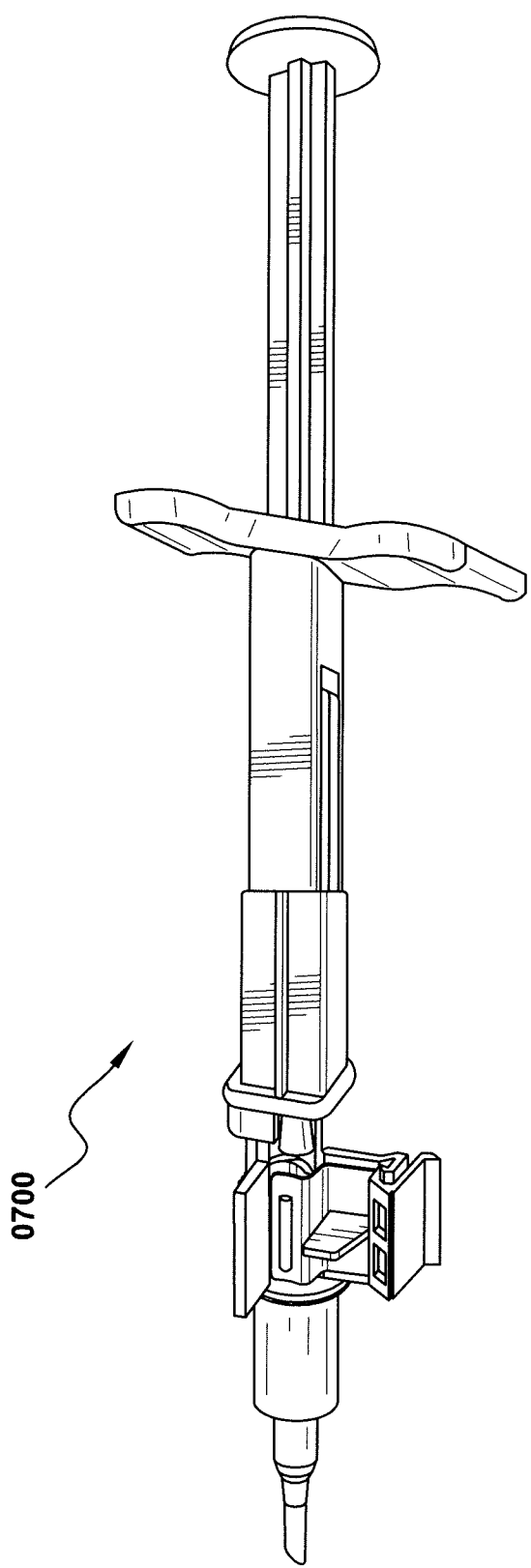
FIG. 7 illustrates a perspective view of a prior art preloaded intraocular lens cartridge as taught by AAREN SCIENTIFIC'S High Precision Injector (HPI) system.
Figure 8:
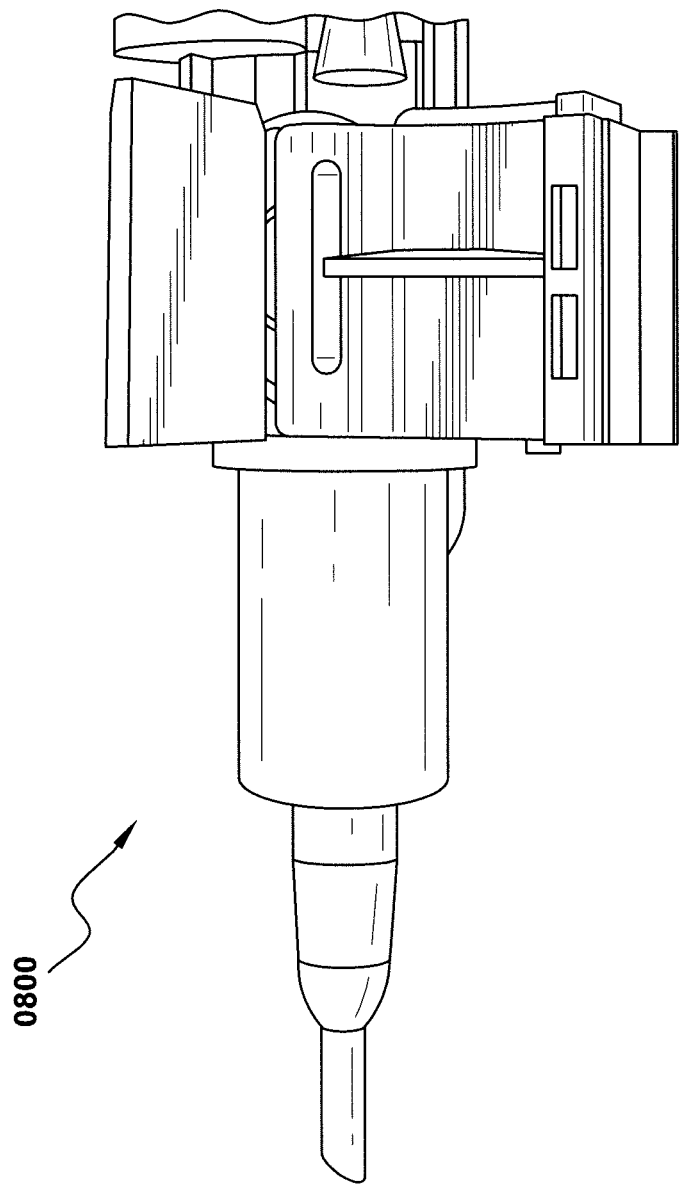
FIG. 8 illustrates a perspective view of a prior art preloaded intraocular lens cartridge as taught by AAREN SCIENTIFIC'S High Precision Injector (HPI) system.

FIG. 5 (0400)-FIG. 6 (0600) illustrate the IOL (0510) positioning within this conventional Preload System. The IOL in a typical preload system (such as the one illustrated in FIG. 3 (0300)-FIG. 4 (0400)) is totally relaxed without compression of the haptics (0511, 0512). The lens (0510) is fixed into position by a positioning clip with two pins to prevent the lens movement during shipping, storage, and other situations as generally illustrated in FIG. 7 (0700) and FIG. 8 (0800).

Figure 9:
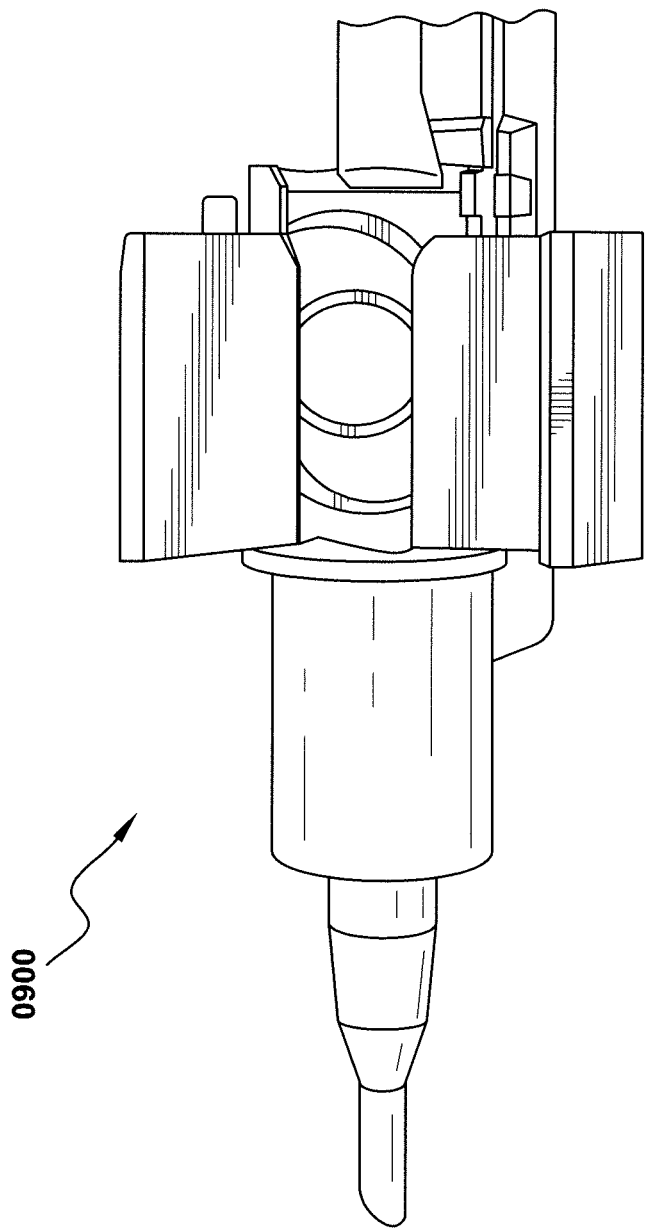
FIG. 9 illustrates a perspective view of a prior art preloaded intraocular lens cartridge as taught by AAREN SCIENTIFIC'S High Precision Injector (HPI) system, detailing relaxed haptics.
Figure 10:
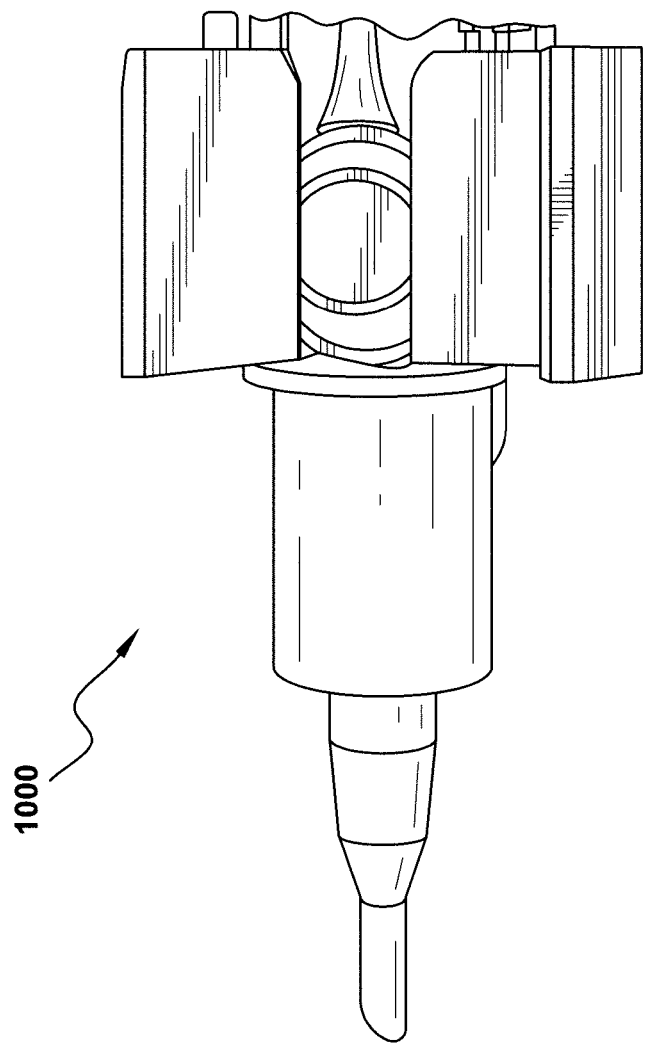
FIG. 10 illustrates a perspective view of a prior art preloaded intraocular lens cartridge as taught by AAREN SCIENTIFIC'S High Precision Injector (HPI) system, detailing compressed haptics.

In this type of Preloading System, which is representative of existing technology, it is necessary for surgeons to compress the haptics (0511, 0512) of the IOL around the optic body prior to the folding step in the surgical center. It is usually done by slowly advancing the plunger of the injector with a manual control by a surgeon or an experienced nurse. In this manner haptic bodies are wrapping around the optic body in an approximately coplanar fashion with a haptic-to-haptic diameter of 7 to 12 mm, preferably 8-11 mm. The next step is to inject viscoelastic into the lens holding chamber, and then fold the lens by closing the two wings. This procedure is designed to insure that the injected lens will unfold in an approximately coplanar fashion within the eye. This technique is generally illustrated in FIG. 9 (0900) and FIG. 10 (1000) wherein an IOL in the preload system (optical body and haptic bodies are in a totally relaxed state (FIG. 9 (0900)) and haptics are in the compressed state by manually moving forward the plunger (FIG. 10 (1000)), a step done by a surgeon or a nurse prior to folding the lens.

Achieving Consistent IOL Placement (0900)-(1000)

In order to achieve a predictable orientation of an IOL into an eye, it is necessary for surgeons to compress the haptics around the optic body prior to the folding step. This is usually achieved by slowly advancing the plunger of the injector with a manual control by a surgeon or an experienced nurse (the "Wrapping Step"). In this fashion, haptic bodies are wrapping around the optic body in an approximately coplanar fashion with a haptic-to-haptic diameter of 7 to 12 mm, preferably 8-11 mm. The second step is to inject viscoelastic into the lens holding chamber, followed by folding the lens by closing two wings. This procedure will ensure that the injected lens will unfold in an approximately coplanar fashion to provide a predictable and corrective lens orientation inside the eye.

To summarize, achieving predictable orientation of the IOL may be accomplished by executing the following steps:
  (1) slowly advancing the plunger of the injector with a manual control to wrap the haptic bodies around the optic body in an approximately coplanar fashion (the "Wrapping Step");
  (2) inject viscoelastic into the lens holding chamber; and
  (3) folding the lens by closing two wings.
This procedure is generally illustrated in FIG. 9 (0900) and FIG. 10 (1000).

Present Invention Operational Comparison (1100)-(1400)

Figure 11:
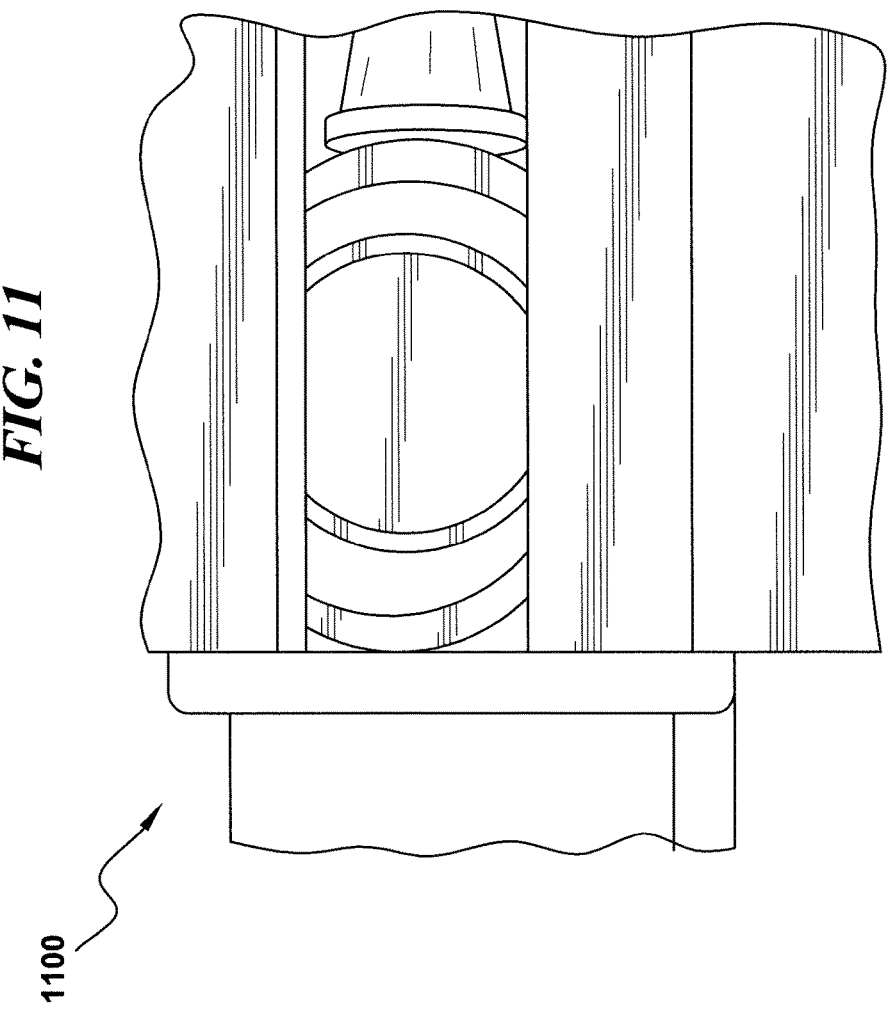
FIG. 11 illustrates a view of an exemplary invention embodiment employing compressed haptic storage.
Figure 12:
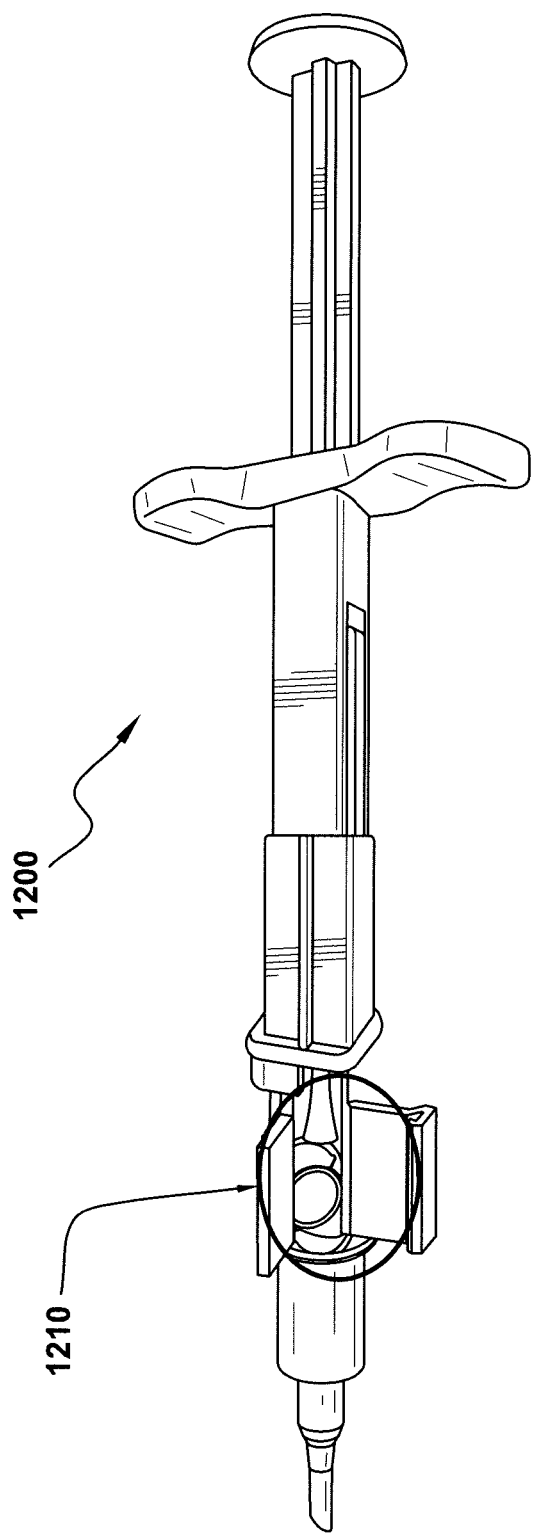
FIG. 12 illustrates a view of an exemplary invention embodiment employing compressed haptic storage in an IOL delivery system.

The present invention eliminates the need for the Wrapping Step by preloading the lens with haptics in an already compressed configuration as generally shown in FIG. 11 (1100) and FIG. 12 (1200). This "preloaded compressed" configuration (as illustrated in FIG. 12 (1210) also allows the lens manufacturer to tightly control lens positioning within the injector body up to the point of injection of the lens into the patient. This step not only saves time for surgeons or nurses but also enhances the success rate by eliminating the potential errors during or as a result of the Wrapping Step. One of the errors which often occurs is the over-compression of the haptics in such a way that the haptic bodies bend over (above or below) the optic body. Consequently, the haptic bodies, as injected with the optic body, increase the size of the folded lens significantly. This increase in size makes it more difficult to inject the lens and creates in some cases damage to the lens or cosmetic issues as to the lens.

Another benefit of the present invention is the elimination of the pins or other apparatus which are required to fixate the lens in place during storage and shipping (see FIG. 3 (0300, 0310)). When the pins or other apparatus is assembled at manufacturer's site, an operator has to ensure that two pins (0310) are precisely located OUTSIDE the optic body but INSIDE (0320) of the haptic bodies and that two pins cannot touch or poke into the optic body accidentally, resulting in damage to the optic body. All of these areas are of concern in the manufacturing process.

In the present invention the elastic forces created by compressing haptics around the optic body provide a means for fixating the lens in place. Therefore, the present invention eliminates the risks identified above by manufacturing the IOL delivery in a predefined configuration as generally illustrated in FIG. 12 (1200).

In one of the preferred embodiments of the present invention, the cartridge 5400 comprises a lens holding portion (or loading chamber) 5403 for storage and folding the lens. This lens holding portion is connected to a gradually tapered inner tube portion 5701 leading to a distal opening end 5601 wherein the folded lens is delivered into the eye of a patient. The lens holding portion comprises a cylindrical shaped tube with internal rails 5402 which contact the edge of a lens during storage and assist in folding the lens into folded shape. The lens holding portion further comprises a hinge 4102 which allows the tube to be opened by separating two wings 4101 connected to the tube structure for receiving an IOL and for folding the lens by closing the two wings.

Figure 13:
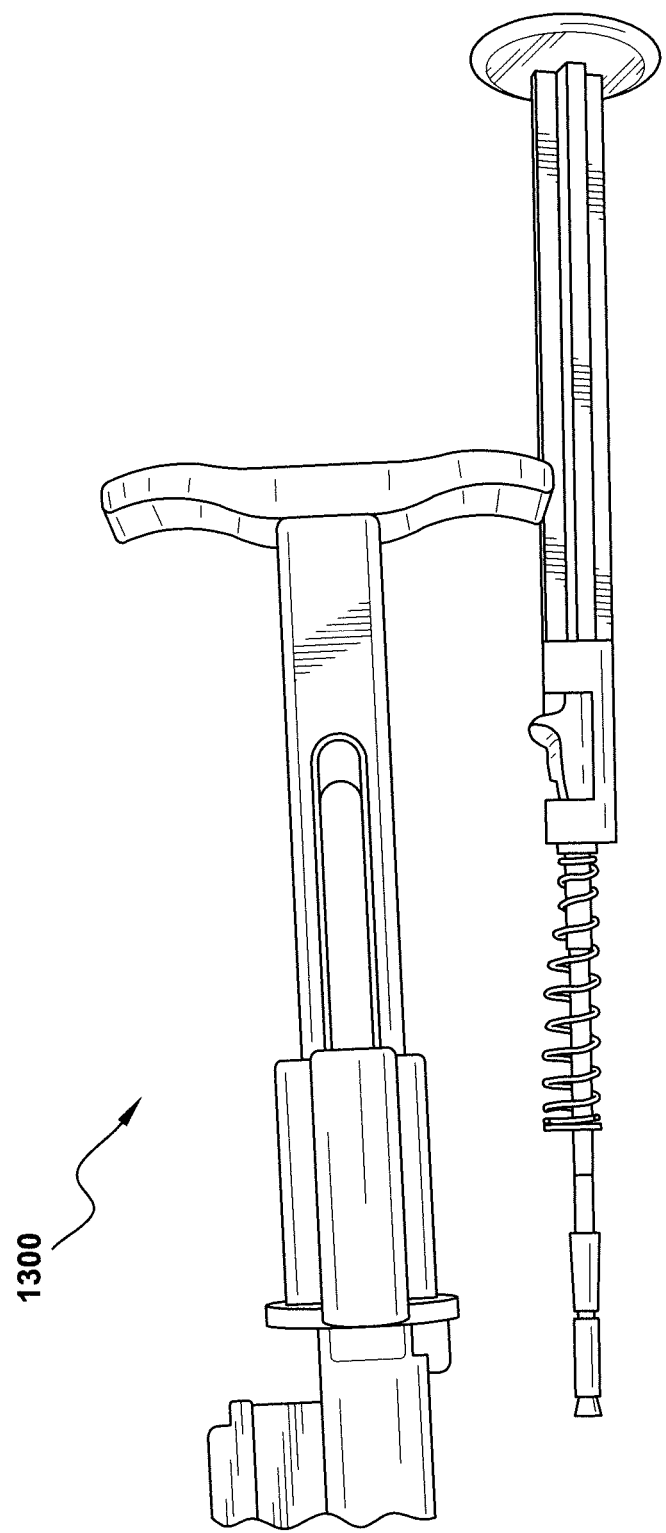
FIG. 13 illustrates an exemplary invention positioning mechanism for a plunger to be engaged with the lens injector (separated)
Figure 14:
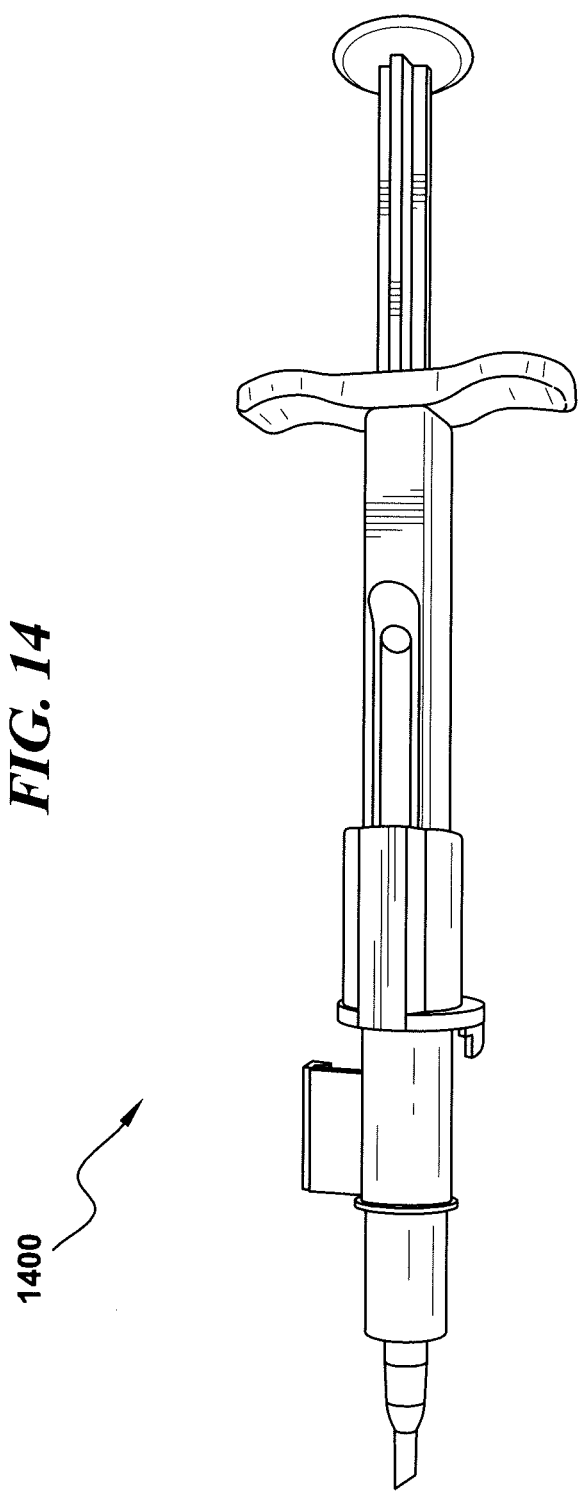
FIG. 14 illustrates an exemplary invention positioning mechanism for a plunger to be engaged with the lens injector (engaged into position)

Furthermore, the cartridge of the present invention preferably has a lock mechanism (as generally depicted in FIG. 13 (1300) and FIG. 14 (1400)) which (when the two wings are closed for folding the lens) provides a means for maintaining the Preloaded System in the folded position. The injector in the present invention comprises an injector body which holds/retains the cartridge in place and a plunger which further comprises a soft cushion connected with the plunger body. When the plunger is moving forwarded, the soft cushion directly contacts and forces the trailing haptic to bend around the optic body while the leading haptic also bend around the optic body, as shown in FIG. 11 (1100). When the haptic bending/wrapping around the optic body reaches a desired position the plunger is structured to be temporarily locked into the injector body in a pre-determined position.

The present invention allows the Wrapping Step to be performed by a lens manufacturer at its site. Surgeons simply apply sufficient amount of viscoelastic material into the cartridge and close two wings of the cartridge along the hinge line to Fold the lens and then Inject the lens. The Folded lens will unfold after being delivered into the eye into the desired predicted orientation by unfolding in a substantially coplanar fashion.

Lens Compression

Unexpected Lens Results (1500)-(1600)

A core precept of prior art IOL systems has been that compression of the lens under storage eventually leads to lens shape deformation such that when a previously compressed IOL is placed within the patient's eye the IOL will fail to properly unfold and function correctly after insertion into the patient. Traditional lens retainers and prior art preload systems are always designed to keep the lens in a totally relaxed state, i.e. without any compression or stress to the lens. There are numerous prior art literature documents that explicitly state that it is a requirement to avoid the IOL being compressed or stretched during storage and/or shipment.

The present invention is based on a surprising discovery regarding the long-term compression characteristics of AAREN SCIENTIFIC hydrophobic IOLs which allow them to be compressed during shipment/storage and still properly unfold in the patient when placement occurs. In a surprising contradiction of the prior art literature, it was discovered that a AAREN SCIENTIFIC hydrophobic intraocular lens (IOL) (or other similarly constructed IOL) can be stored in a compressed state for at least the equivalent of 2.5 and 3.5 years respectively and after injection, all the compressed haptic lenses will recover back to their initial dimensions in a very short time period. The experimental details of these tests are discussed in detail below.

Example 1

Experimental Results (1500)

Finished goods inventory lenses (EC-1R HPI and EC-1YR HPI models, by AAREN SCIENTIFIC, INC., Ontario, Calif.), preloaded in an ACCUJECT 2.2-1P instrument with lens haptics compressed into 10 mm of haptic-to-haptic distances, were aged in an incubator at 65° C. for eight weeks (56 days). This is equivalent to approximately 2.5 years of real time shelf-life at 25° C. The specification for the haptic-to-haptic distance for both lens models is 13.00+0.20 mm. At the end of the eight week accelerated ageing, these lenses were allowed to cool down to the room temperature. Then they were injected using the same preload instrument by following the steps comprising:

(1) injecting sodium hyaluronate viscoelastic (LA Lon Vicoelastic by LA LABS) into the lens holding chamber;

(2) closing the two wings of the cartridge to fold the lens; and (3) injecting the folded lens into a water cell of 30+2° C. (simulating clinical conditions of human eye temperature in a surgery environment).

Figure 15:
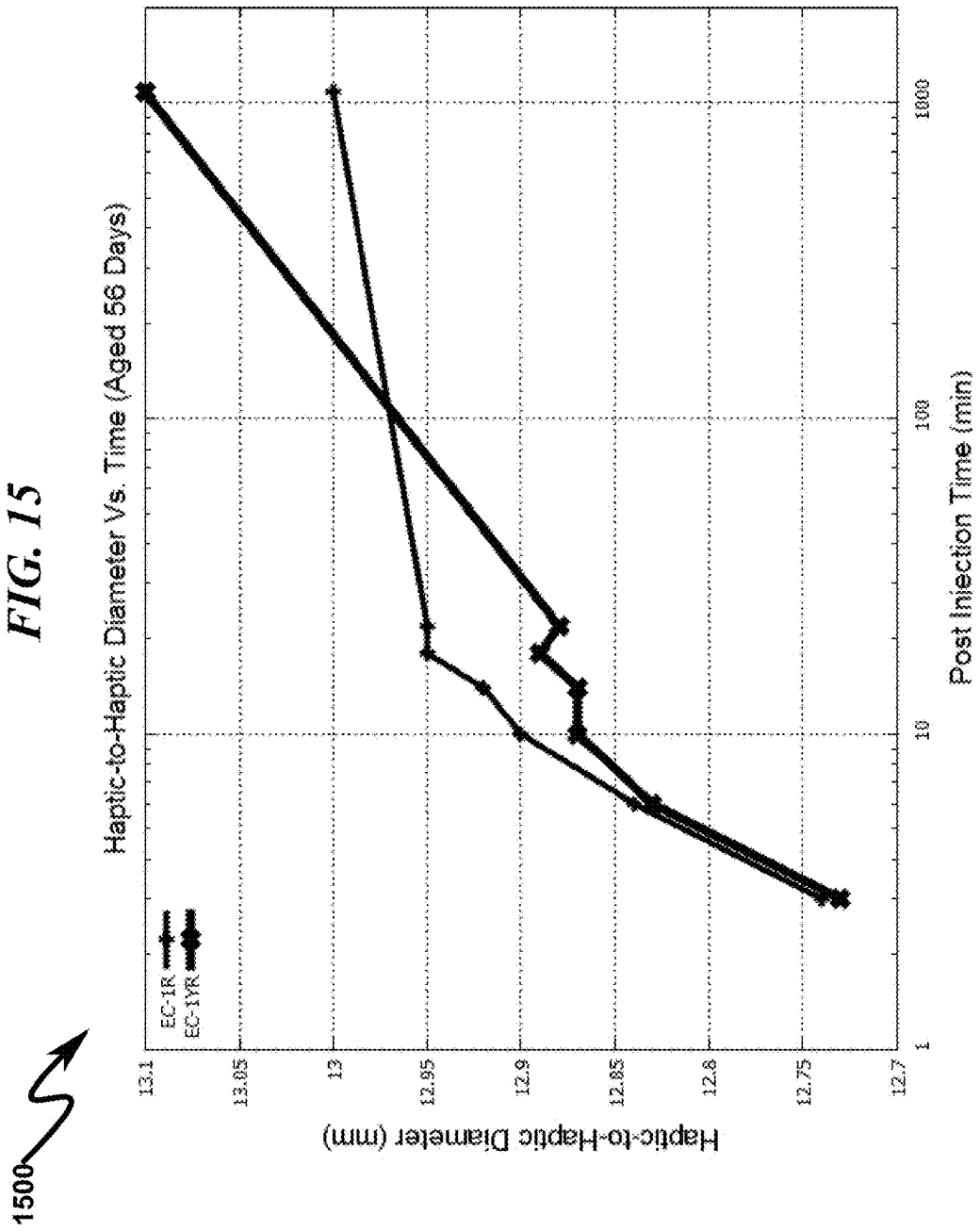
FIG. 15 illustrates an experimental graph depicting haptic-to-haptic distances vs. time for IOLs aged to 56 days at 65° C., an equivalent to 2.5 years at real time shelf-life of 25° C.

The lenses were unfolding in a substantially coplanar fashion within 30 seconds. After the unfolding, each lens was moved out from the water cell to a fixture in the air for the overall diameter (haptic-to-haptic distance) measurement on a comparator at the room temperature. Their results are summarized in TABLE 1 below and graphically depicted in FIG. 15 (1500).

TABLE 1

LENS DIMENSION RECOVERY AFTER ACCELERATED AGEING AT 65° C. FOR 56 DAYS

| Time/Conditions after Injection | Haptic-to-Haptic Diameter For EC-1R Lens (mm) | Haptic-to-Haptic Diameter For EC-1YR Lens (mm) |
|---|---|---|
| 3 minutes/ in air 25° C. | 12.74 | 12.73 |
| 6 minutes/ in air 25° C. | 12.84 | 12.83 |
| 10 minutes/ in air 25° C. | 12.90 | 12.87 |

TABLE 1-continued

LENS DIMENSION RECOVERY AFTER ACCELERATED AGEING AT 65° C. FOR 56 DAYS

| Time/Conditions after Injection | Haptic-to-Haptic Diameter For EC-1R Lens (mm) | Haptic-to-Haptic Diameter For EC-1YR Lens (mm) |
|---|---|---|
| 14 minutes/ in air 25° C. | 12.92 | 12.87 |
| 18 minutes/ in air 25° C. | 12.95 | 12.89 |
| 22 minutes/ in air 25° C. | 12.95 | 12.88 |
| 18 hours/ in water 35° C. | 13.00 | 13.10 |

Example 2

Experimental Results (1600)

Figure 16:
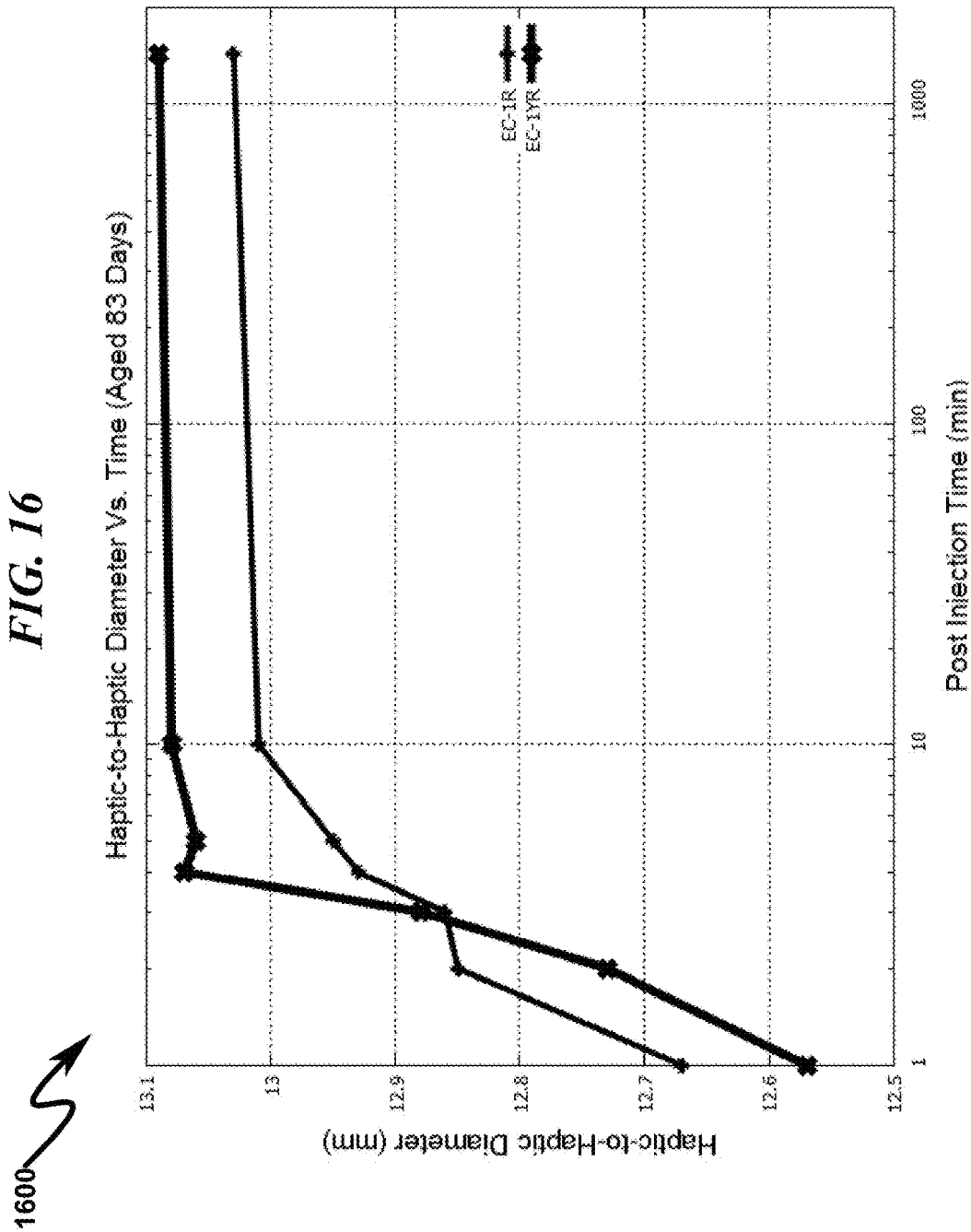
FIG. 16 illustrates an experimental graph depicting haptic-to-haptic distances vs. time for IOLs aged to 83 days at 65° C., an equivalent to 3.6 years at real time shelf-life of 25° C.

Same as in Example 1 except that the ageing is 83 days instead of 56 days. This accelerated ageing of 83 days at 65° C. is equivalent to approximately 3.6 years of shelf-life at real time conditions (25° C.). The injected lenses were allowed to recover to their initial dimensions in water at 30+2° C. and their recovered dimensions were measured during the first 10 minutes post-injection, then 24 hours later at 35° C. in water. The results are summarized in TABLE 2 below and graphically depicted in FIG. 16 (1600).

TABLE 2

LENS DIMENSION RECOVERY AT 30° C. IN WATER (OR OTHERWISE SPECIFIED) AFTER ACCELERATED AGEING AT 65° C. FOR 83 DAYS

| Time/Conditions after Injection | Haptic-to-Haptic Diameter For EC-1R Lens (mm) | Haptic-to-Haptic Diameter For EC-1YR Lens (mm) |
|---|---|---|
| 1 minutes/ in water 30° C. | 12.67 | 12.57 |
| 2 minutes/ in water 30° C. | 12.85 | 12.73 |
| 3 minutes/ in water 30° C. | 12.86 | 12.88 |
| 4 minutes/ in water 30° C. | 12.93 | 13.07 |
| 5 minutes/ in water 30° C. | 12.95 | 13.06 |
| 10 minutes/ in water 30° C. | 13.01 | 13.08 |
| 24 hours/ in water 35° C. | 13.03 | 13.09 |

The data in TABLE 2 indicates that in just one minute post injection, more than 90% of the haptic-to-haptic diameter has been recovered. This immediate recovery is very important because surgeons can only determine if a wholly recovered lens is centered in the pupil. Otherwise, surgeons have to wait until the lens is recovered and then position the lens properly before the patient can be released from the surgery room.

This data demonstrates that IOLs made from highly cross-linked polymers (including but not limited to AAREN SCIENTIFIC ACRYLMEX hydrophobic acrylic polymer) can be stored in a compressed/stressed state. This totally contradicts the traditional thinking that an IOL has to be stored in a totally relaxed state for transportation to the patient, particularly for polymers with high crosslinking.

Preloader Comparison (1700)-(4000)/(4100)-(6100)

Figure 33:
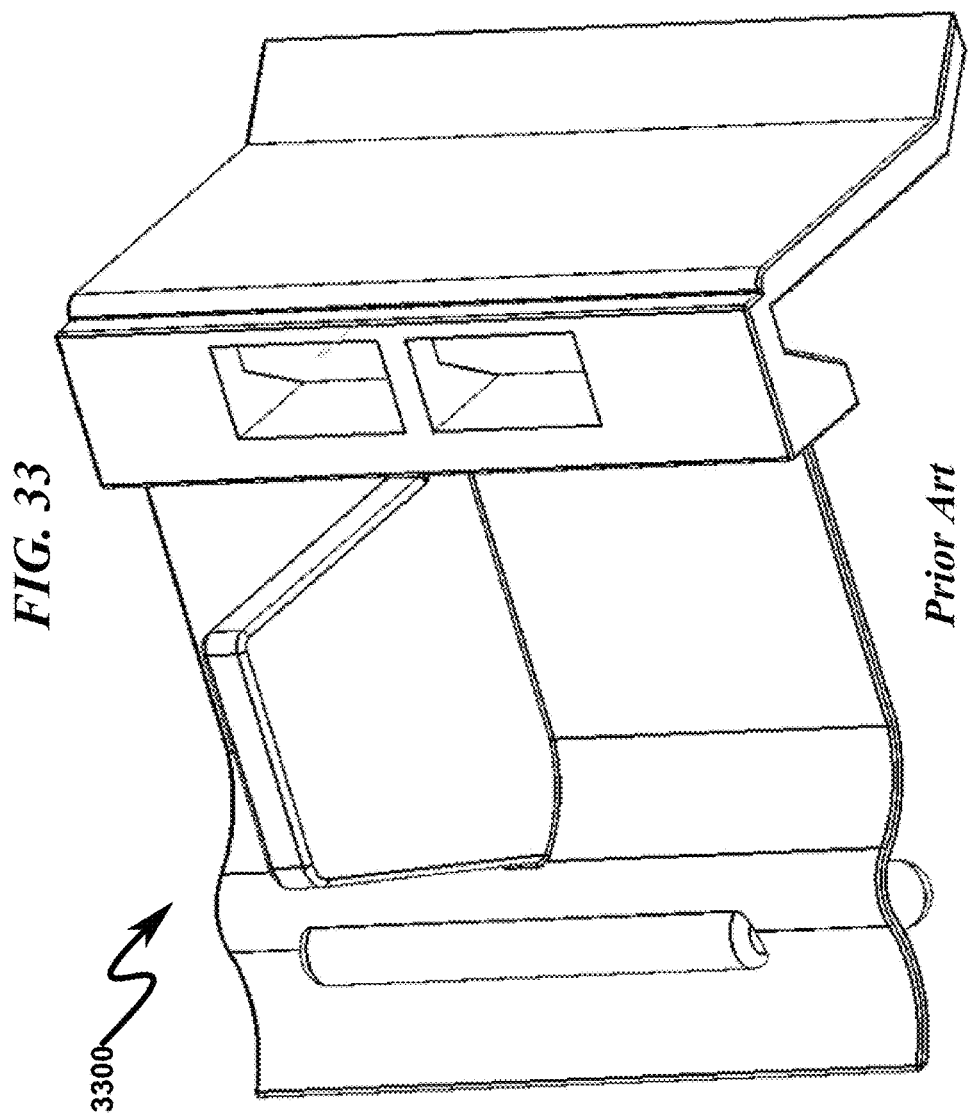
FIG. 33 illustrates a top perspective view of a prior art IOL preload lens holding portion.
Figure 34:
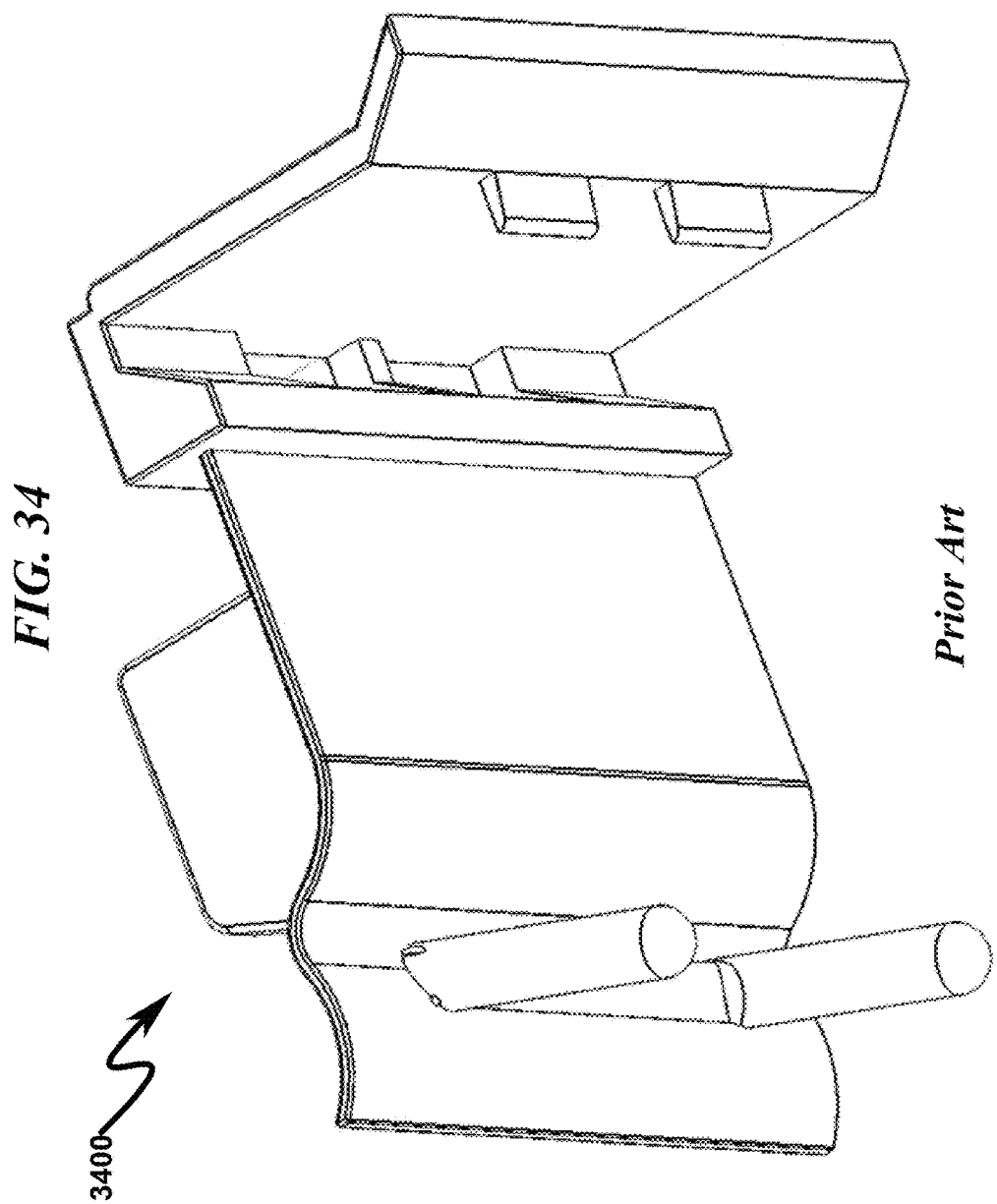
FIG. 34 illustrates an inside perspective view of a prior art IOL preload lens holding portion.
Figure 35:
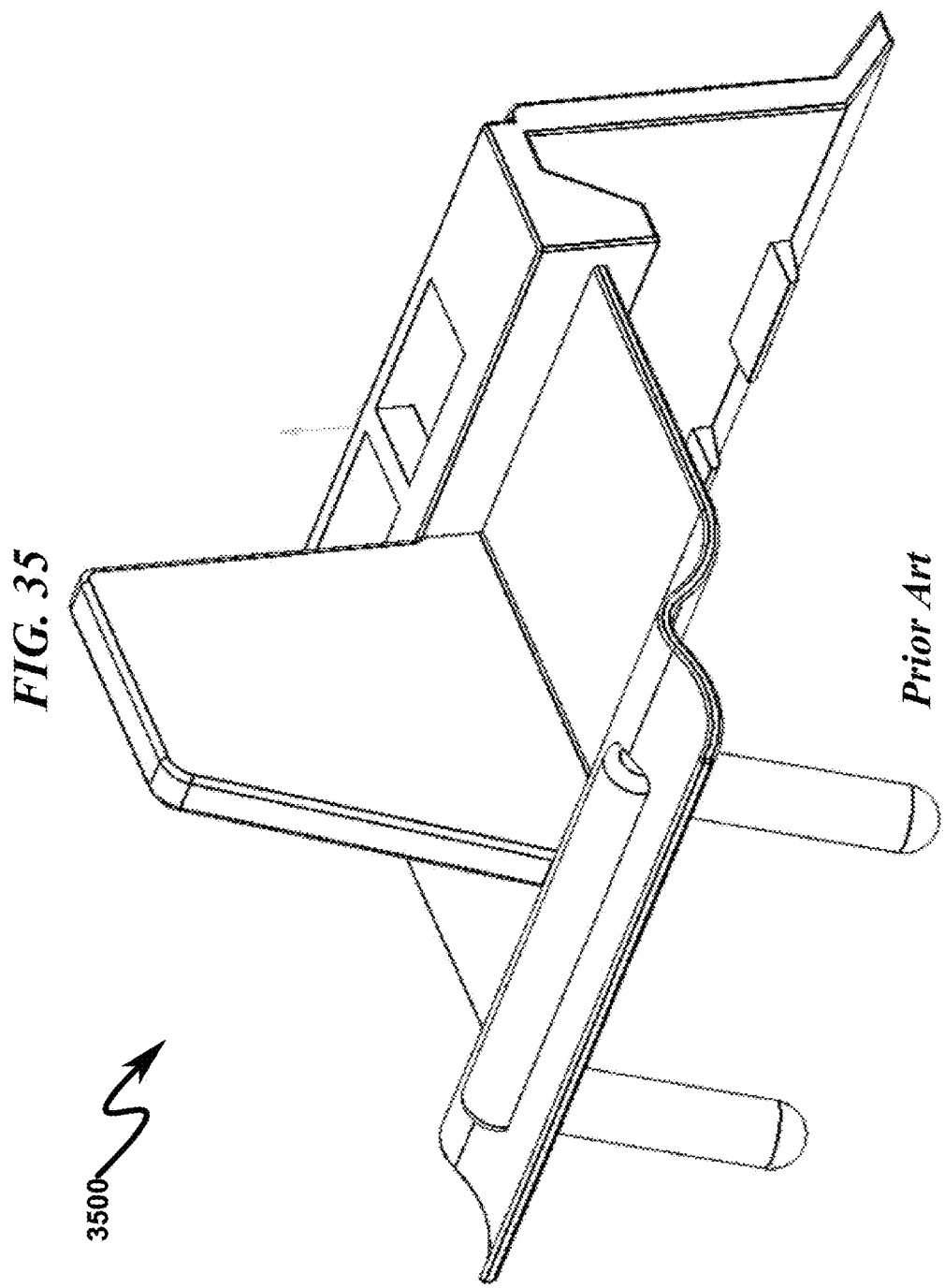
FIG. 35 illustrates a side perspective view of a prior art IOL preload clip which holds lens in a fixated position for preventing from dislocation during transportation and storage.
Figure 36:
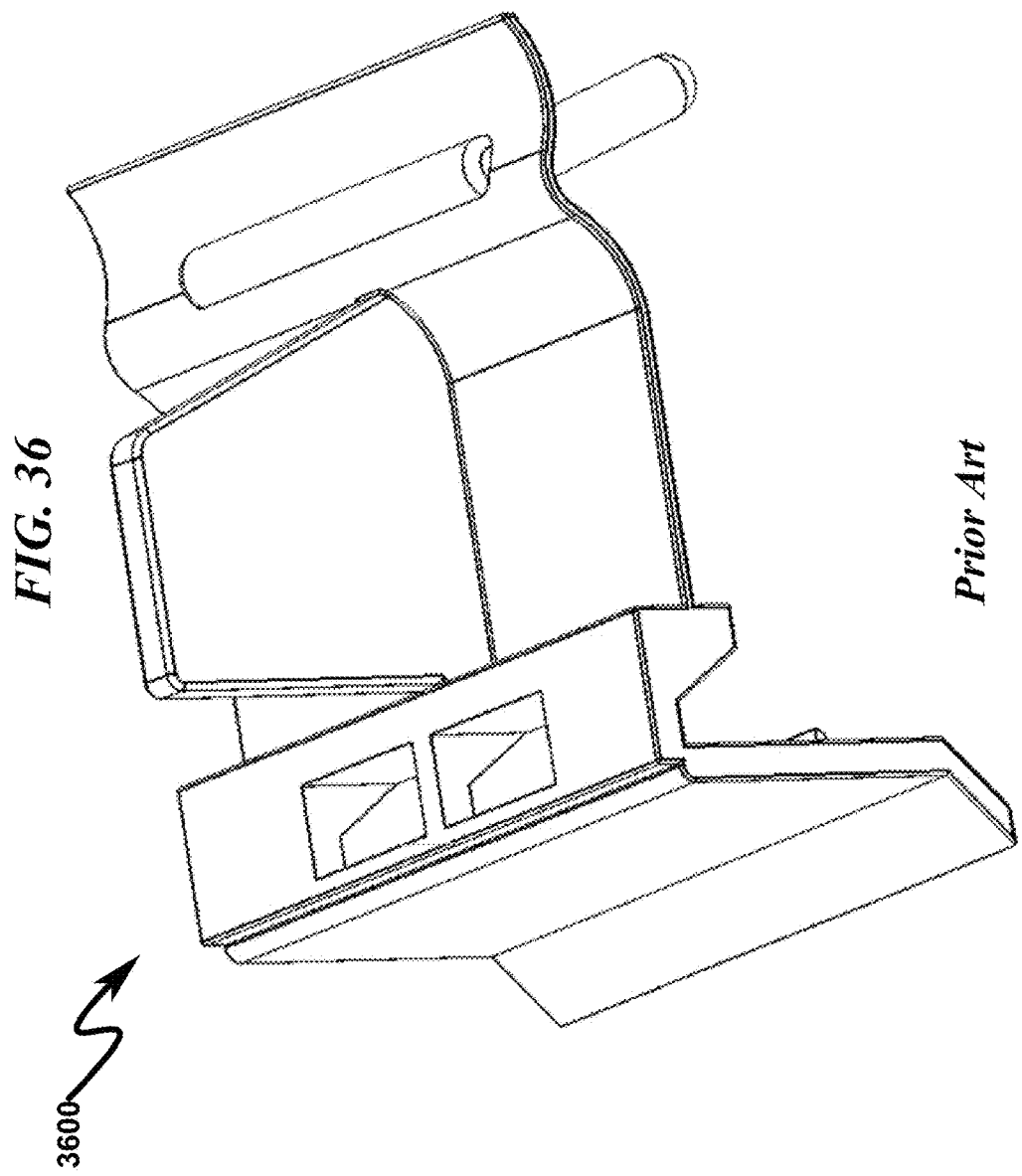
FIG. 36 illustrates a side perspective view of a prior art IOL preload clip.
Figure 37:
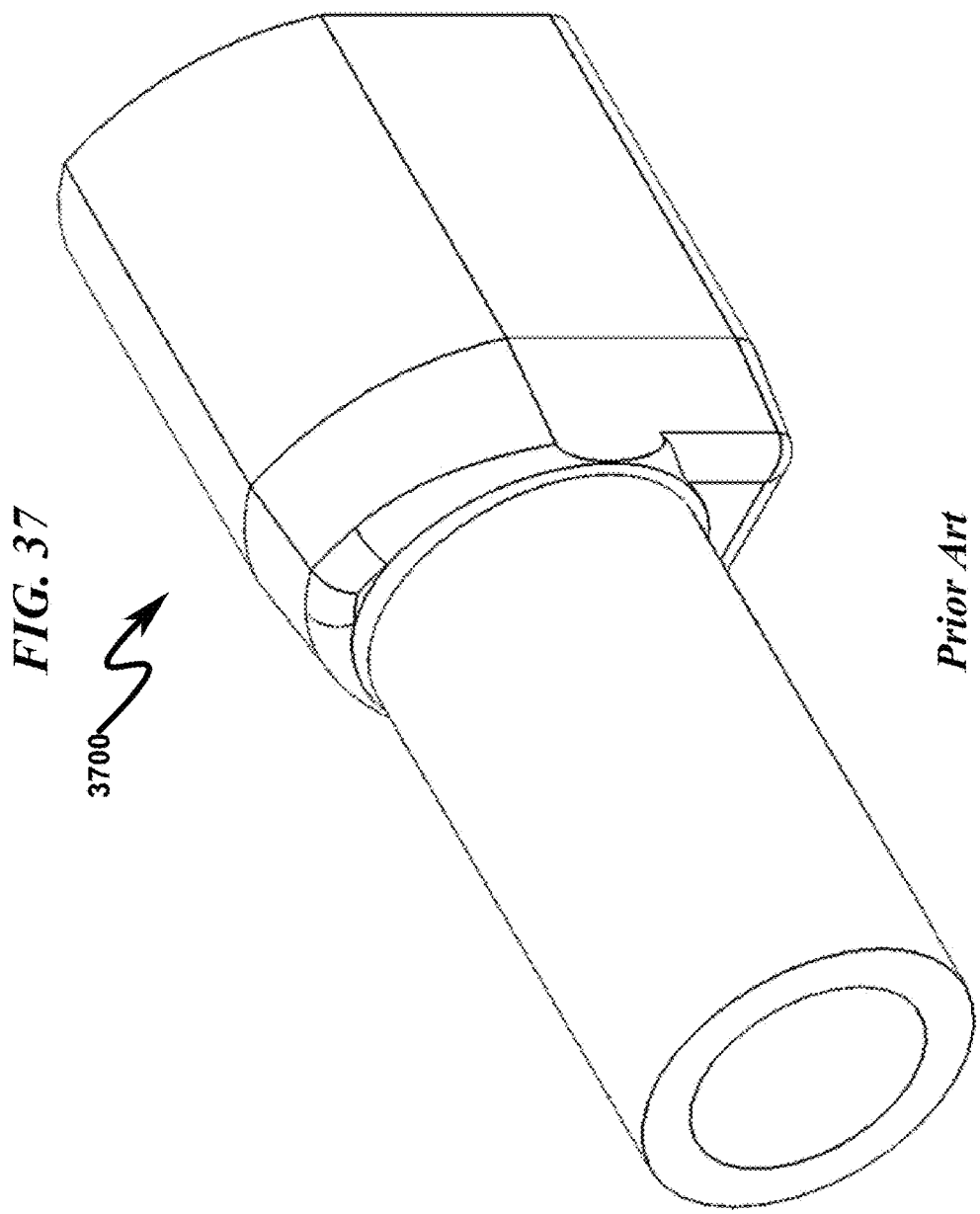
FIG. 37 illustrates a top perspective view of a prior art IOL preload silicon plunger tip.
Figure 38:
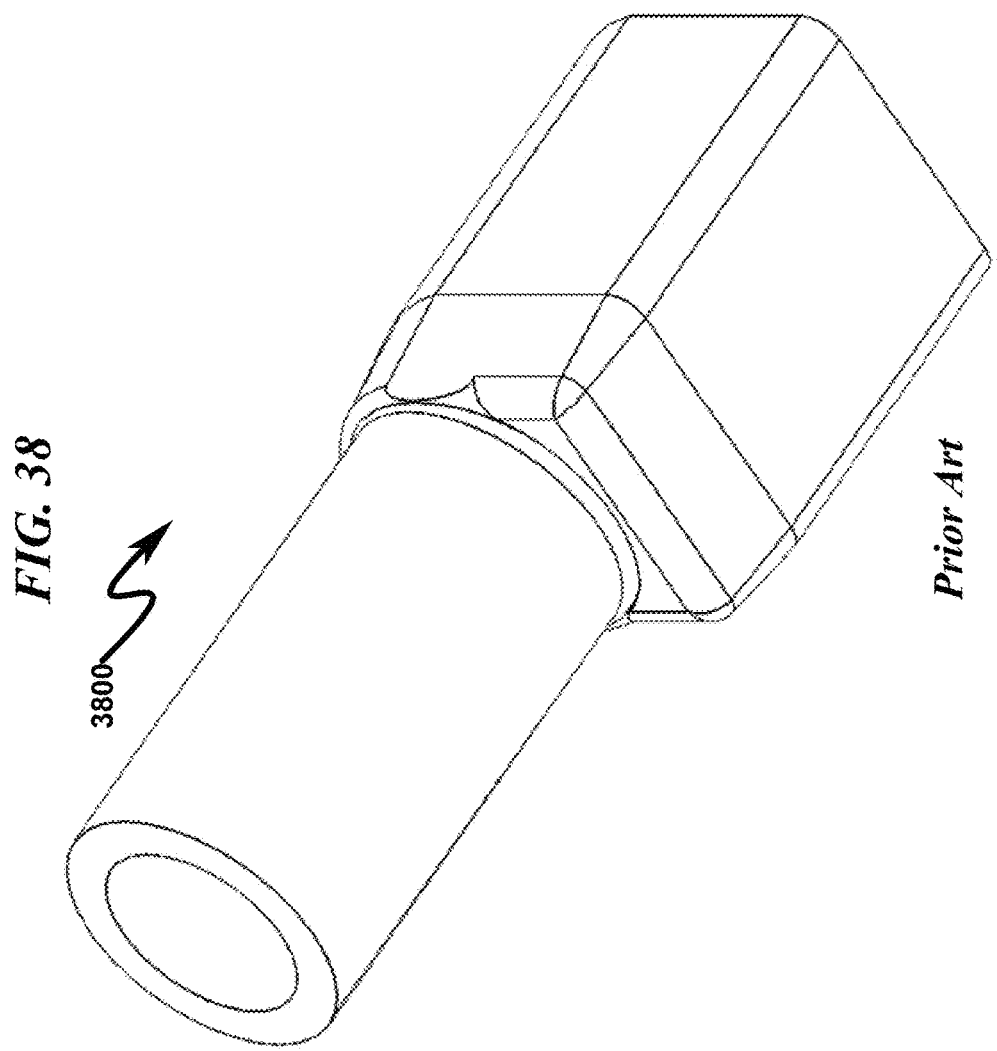
FIG. 38 illustrates a bottom perspective view of a prior art IOL preload silicon plunger tip.
Figure 39:
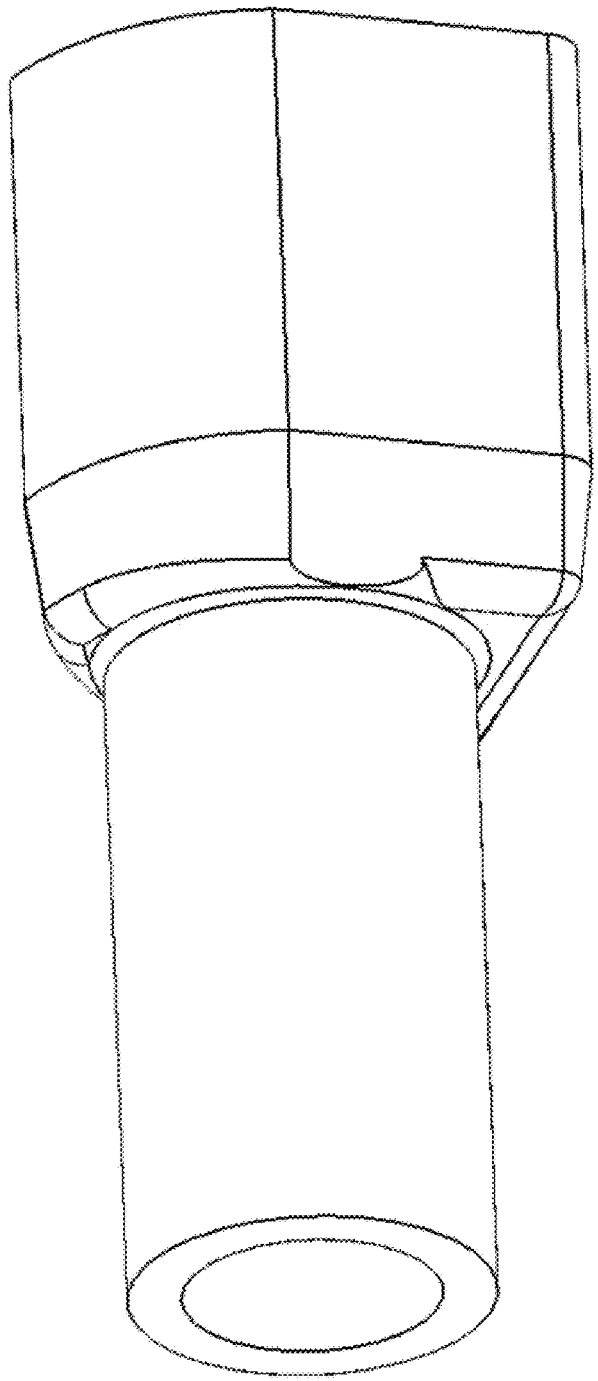
FIG. 39 illustrates a side perspective view of a prior art IOL preload silicon plunger tip.
Figure 40:
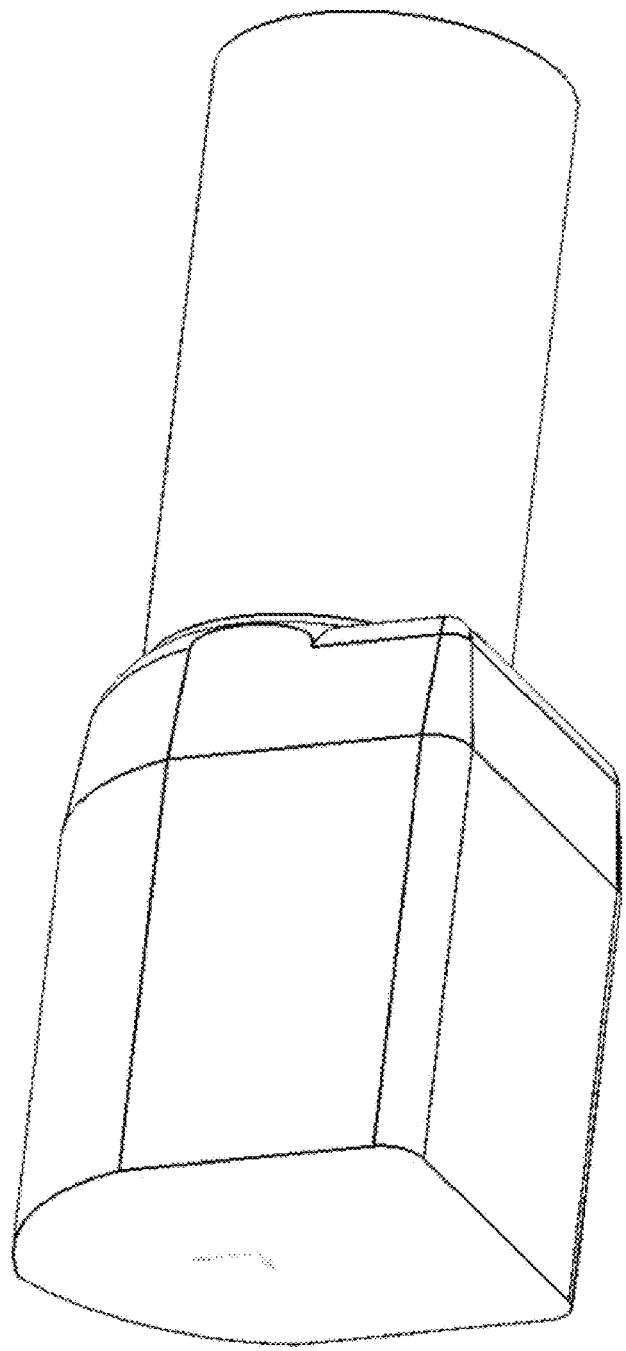
FIG. 40 illustrates a side perspective view of a prior art IOL preload silicon plunger tip.
Figure 41:
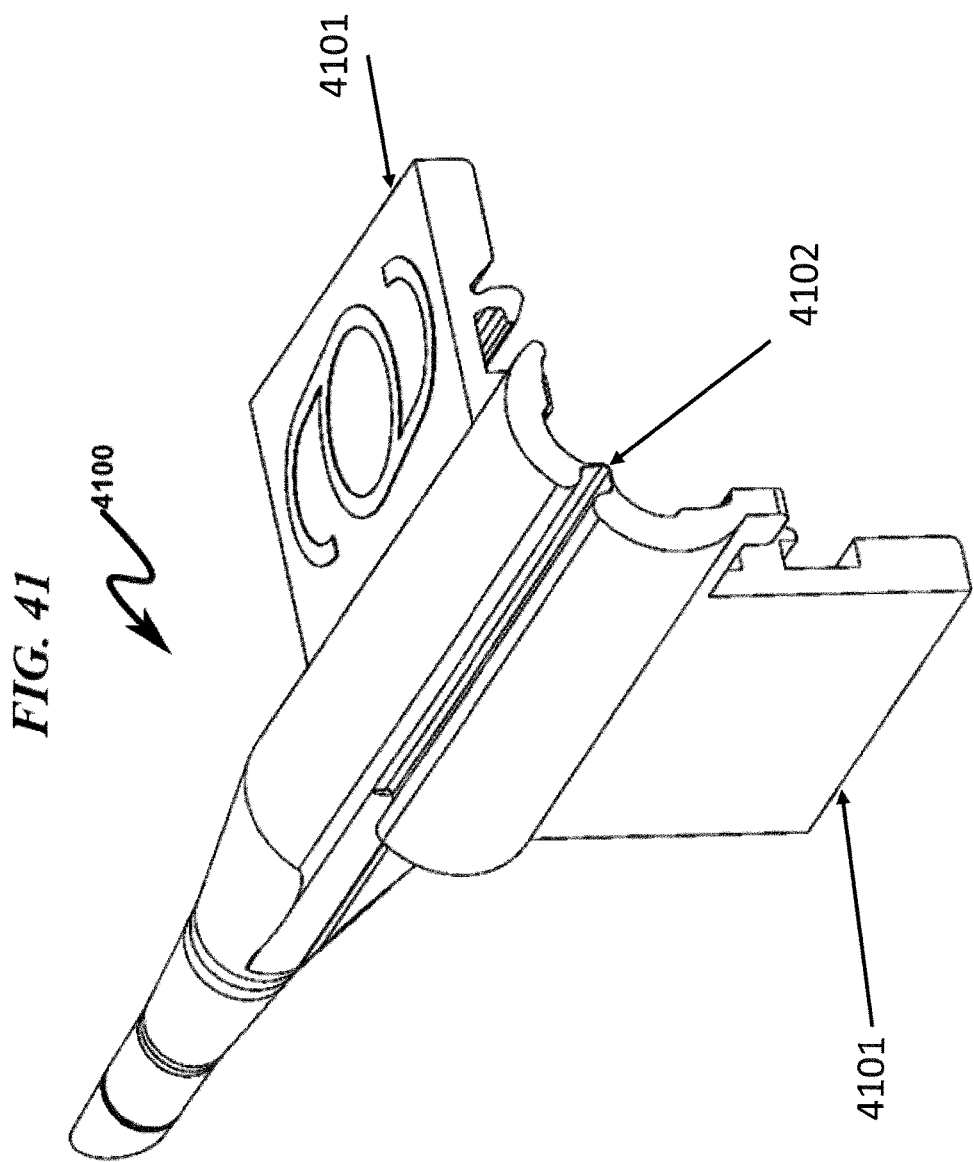
FIG. 41 illustrates a top perspective view of a present invention exemplary embodiment preloaded IOL cartridge.
Figure 42:
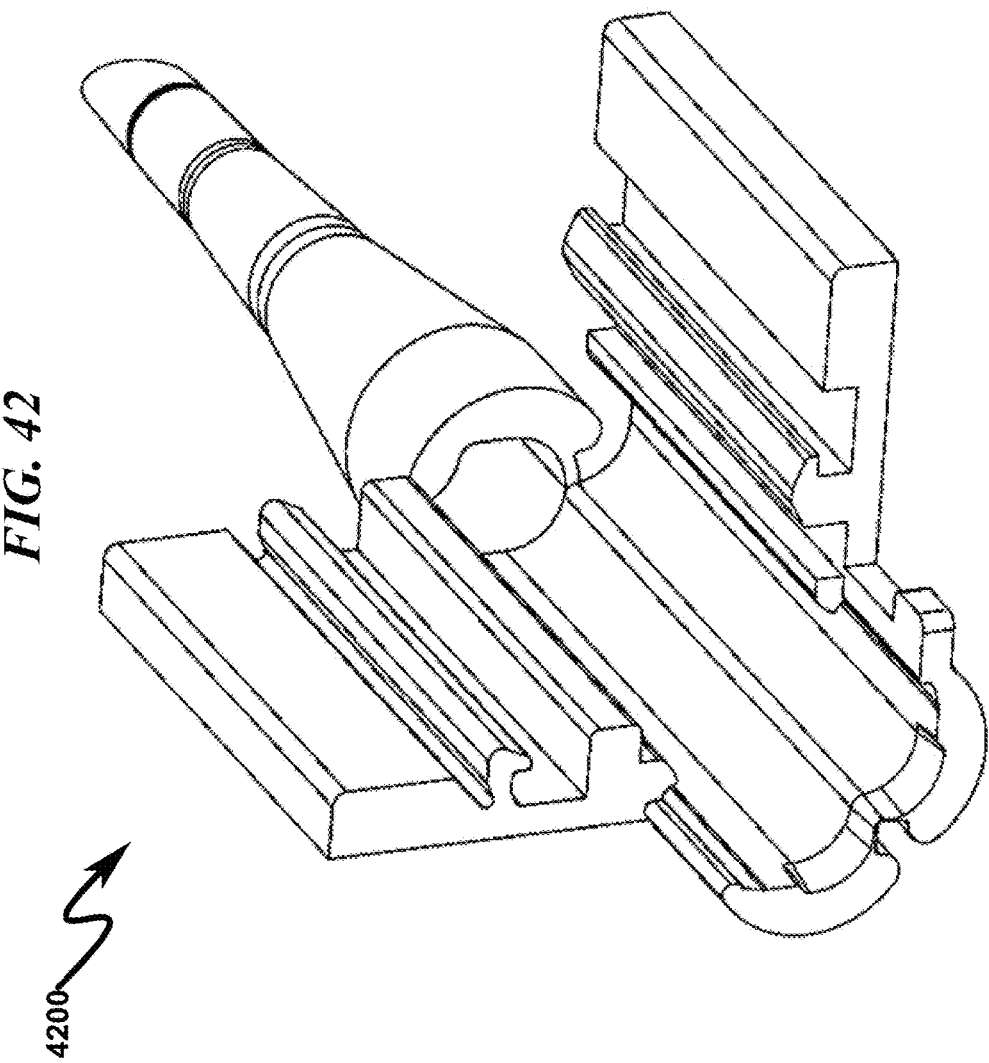
FIG. 42 illustrates a bottom perspective view of a present invention exemplary embodiment preloaded IOL cartridge.
Figure 43:
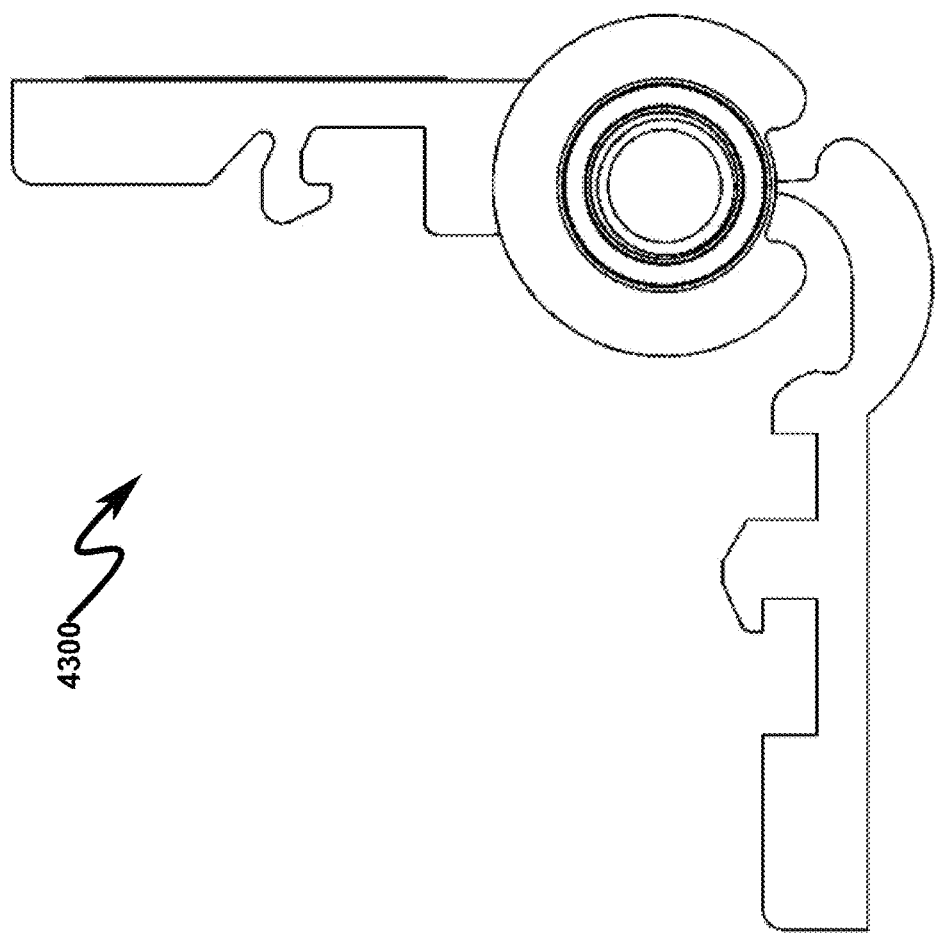
FIG. 43 illustrates a top view of a present invention exemplary embodiment preloaded IOL cartridge.
Figure 44:
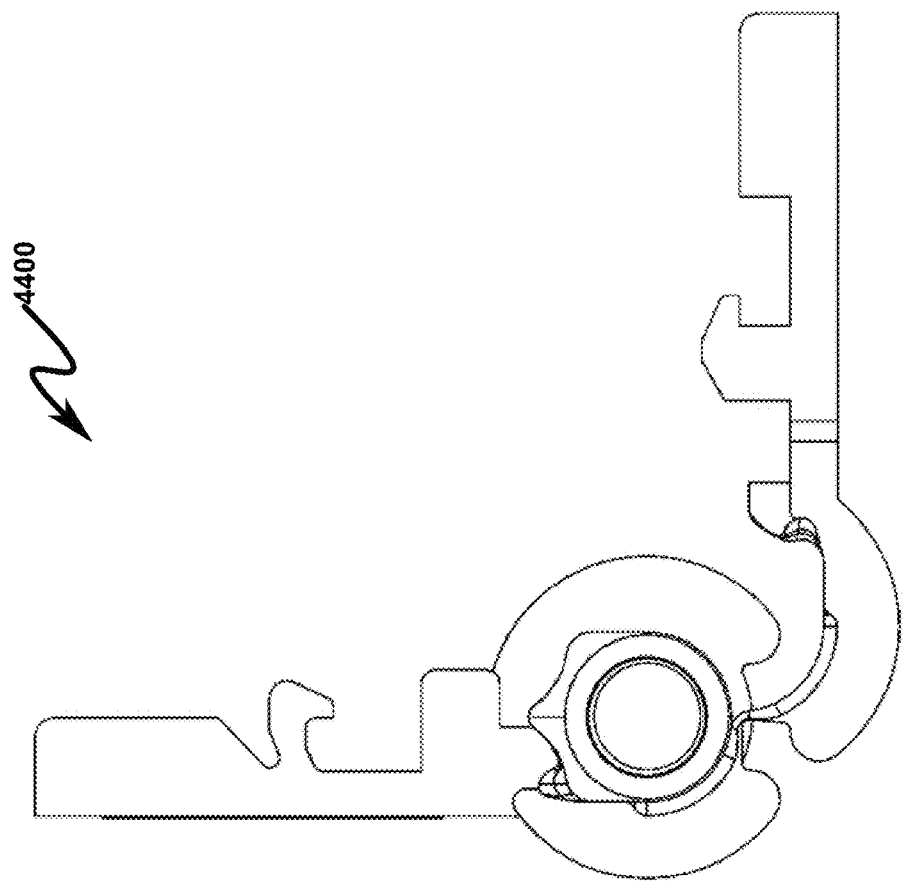
FIG. 44 illustrates a bottom view of a present invention exemplary embodiment preloaded IOL cartridge.
Figure 45:
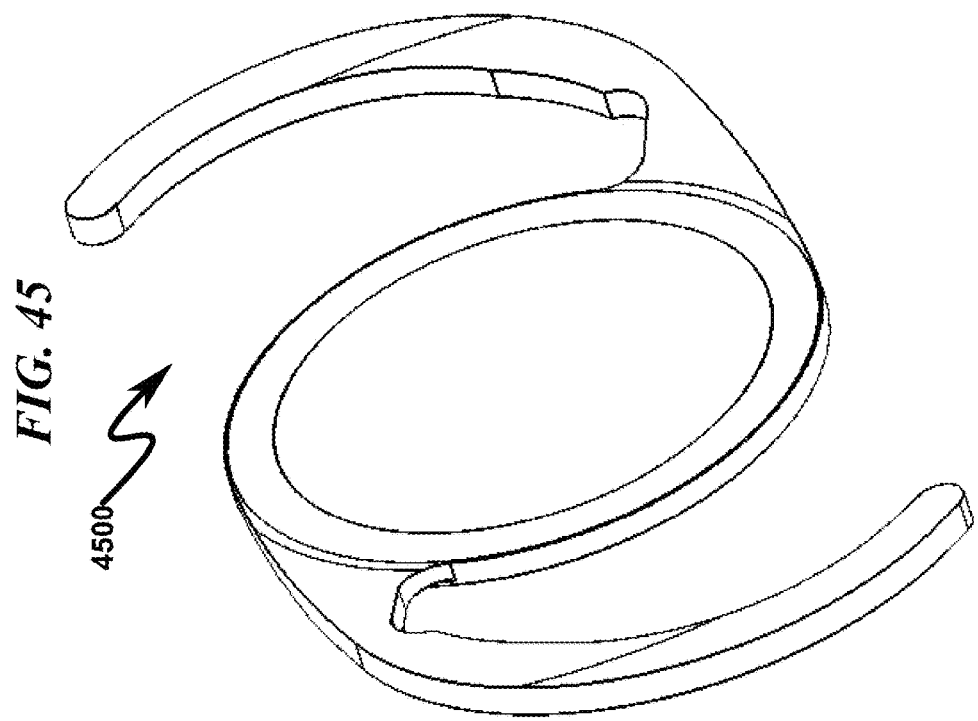
FIG. 45 illustrates a top perspective view of an IOL lens incorporating haptics useful in some preferred invention embodiments.
Figure 46:
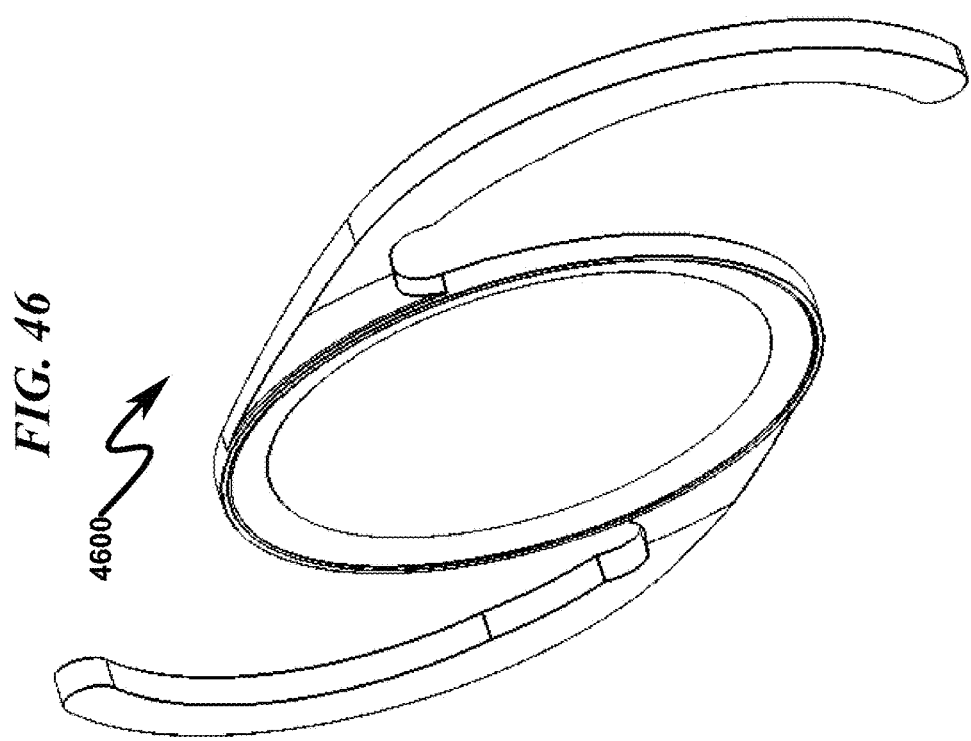
FIG. 46 illustrates a bottom perspective view of an IOL lens incorporating haptics useful in some preferred invention embodiments.
Figure 47:
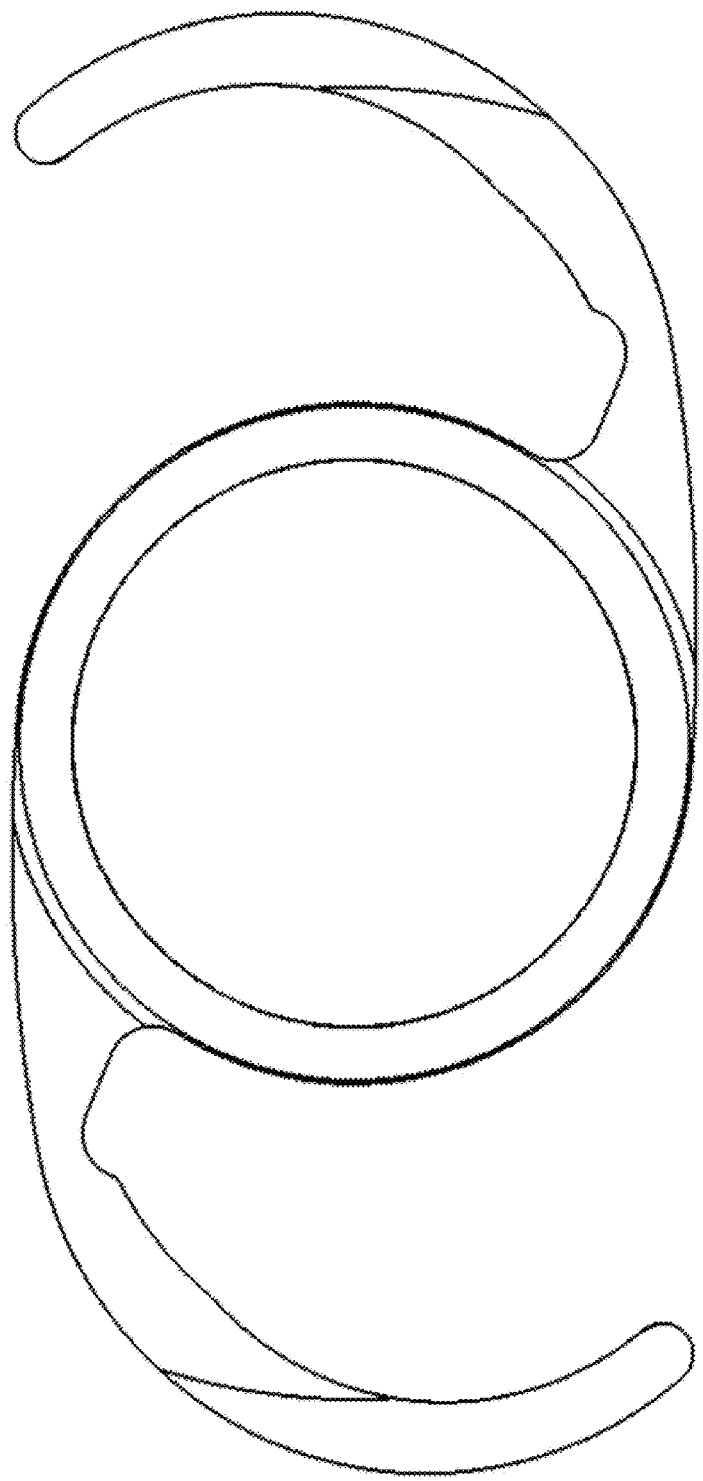
FIG. 47 illustrates a top view of an IOL lens 4700 incorporating haptics useful in some preferred invention embodiments.
Figure 48:
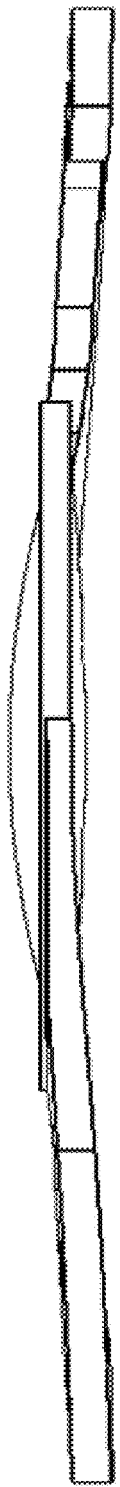
FIG. 48 illustrates a side view of an IOL lens incorporating haptics useful in some preferred invention embodiments.
Figure 61:
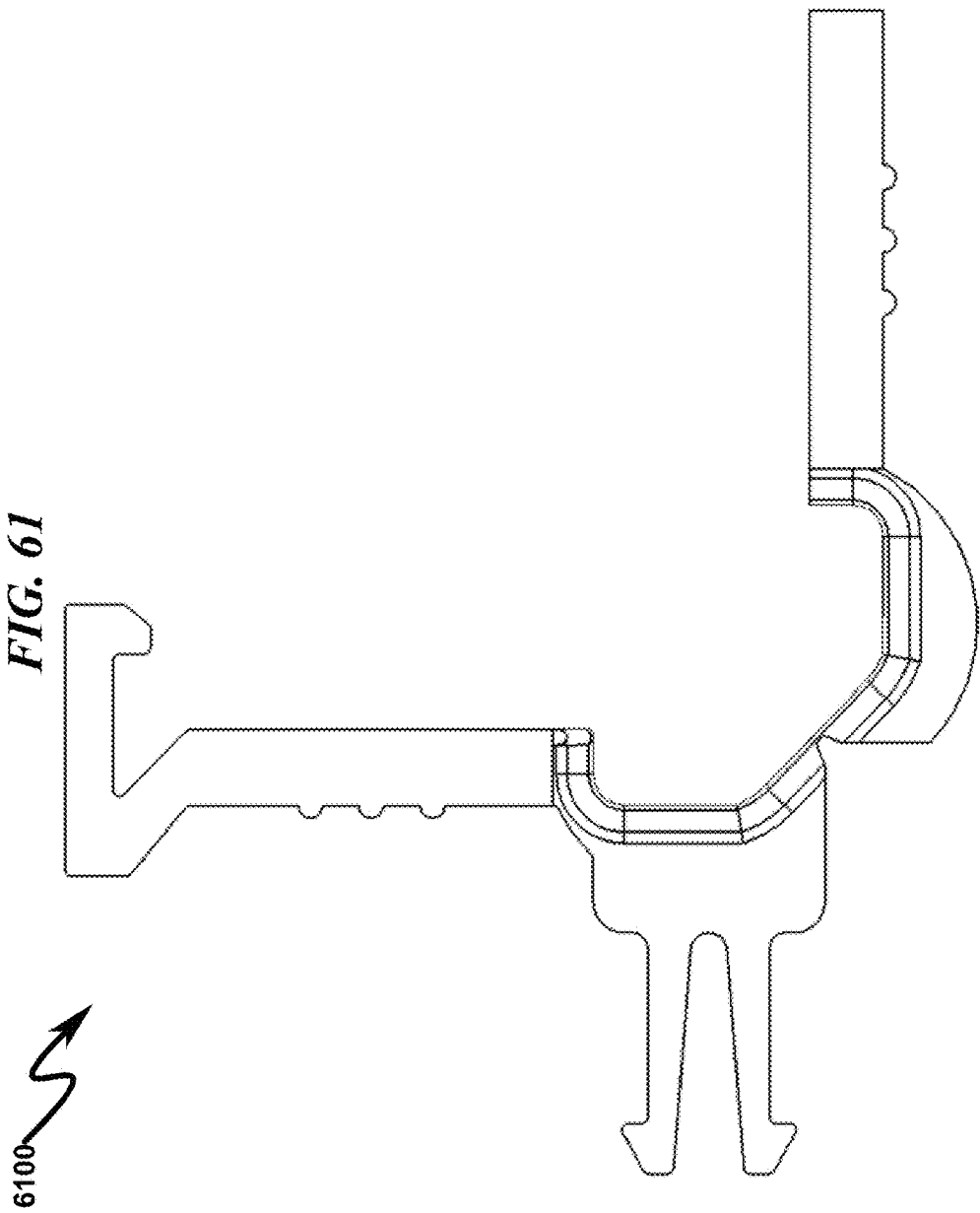
FIG. 61 illustrates a bottom view of an IOL lens holding chamber useful in some exemplary embodiments of the present invention.

The present invention as discussed herein may be contrasted with the prior art IOL preloaders as detailed in FIG. 17 (1700)-FIG. 40 (4000). The general construction of the prior art preloader as shown incorporates the IOL cartridge as detailed in FIG. 33 (3300)-FIG. 36 (3600). This cartridge assembly may be compared with that of the present invention as detailed in FIG. 41 (4100)-FIG. 44 (4400). Here it is seen that the present invention cartridge provides for rails on which the IOL (as generically depicted in FIG. 45 (4500)-FIG. 48 (4800) and further detailed in the lens holding chamber detail views of FIG. 58 (5800)-FIG. 61 (6100)) may rest prior to the cartridge assembly being folded over and snapped into a locked position.

Figure 49:
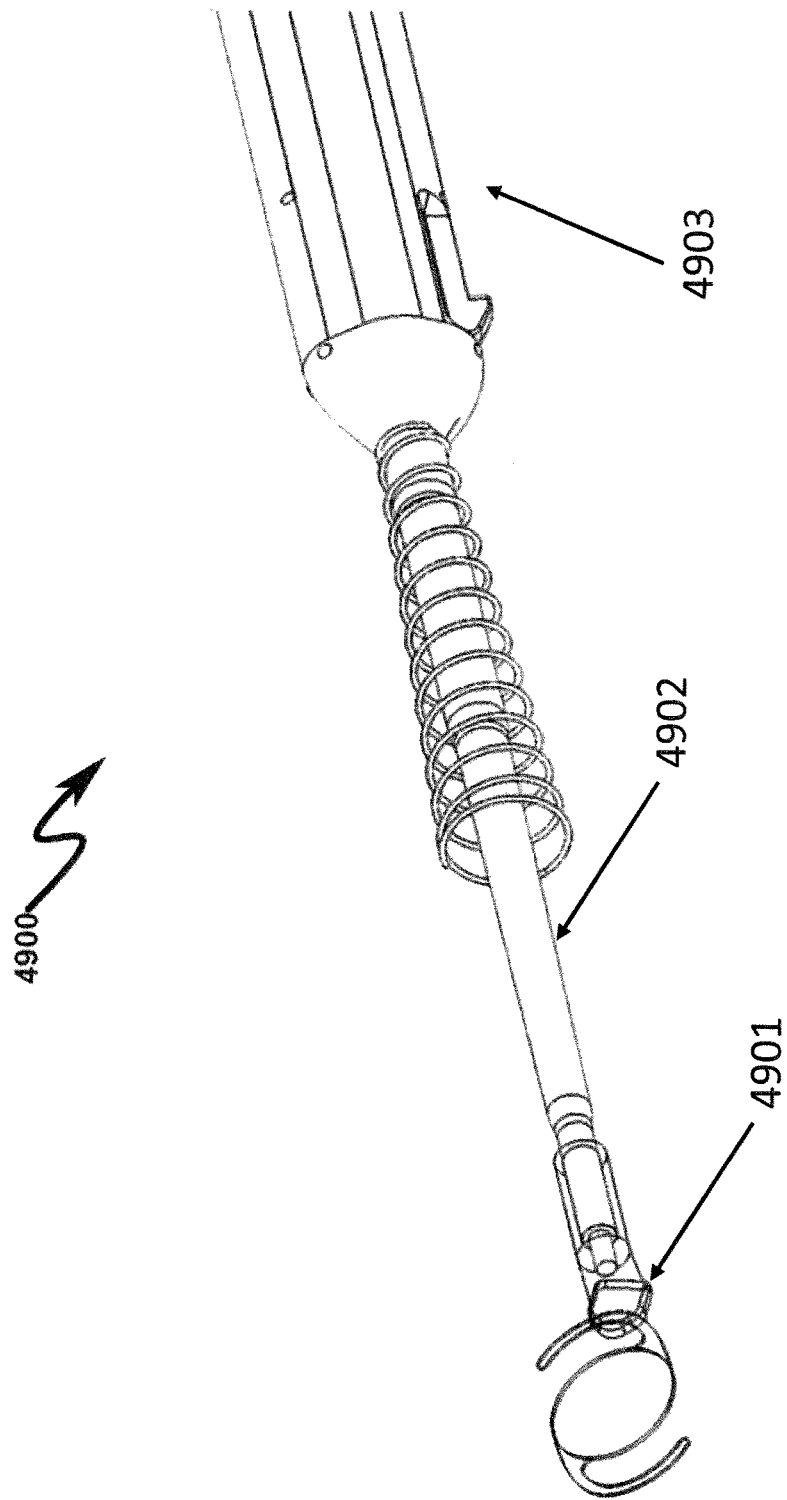
FIG. 49 illustrates a side perspective view of an injector assembly useful in some exemplary embodiments of the present invention.
Figure 50:
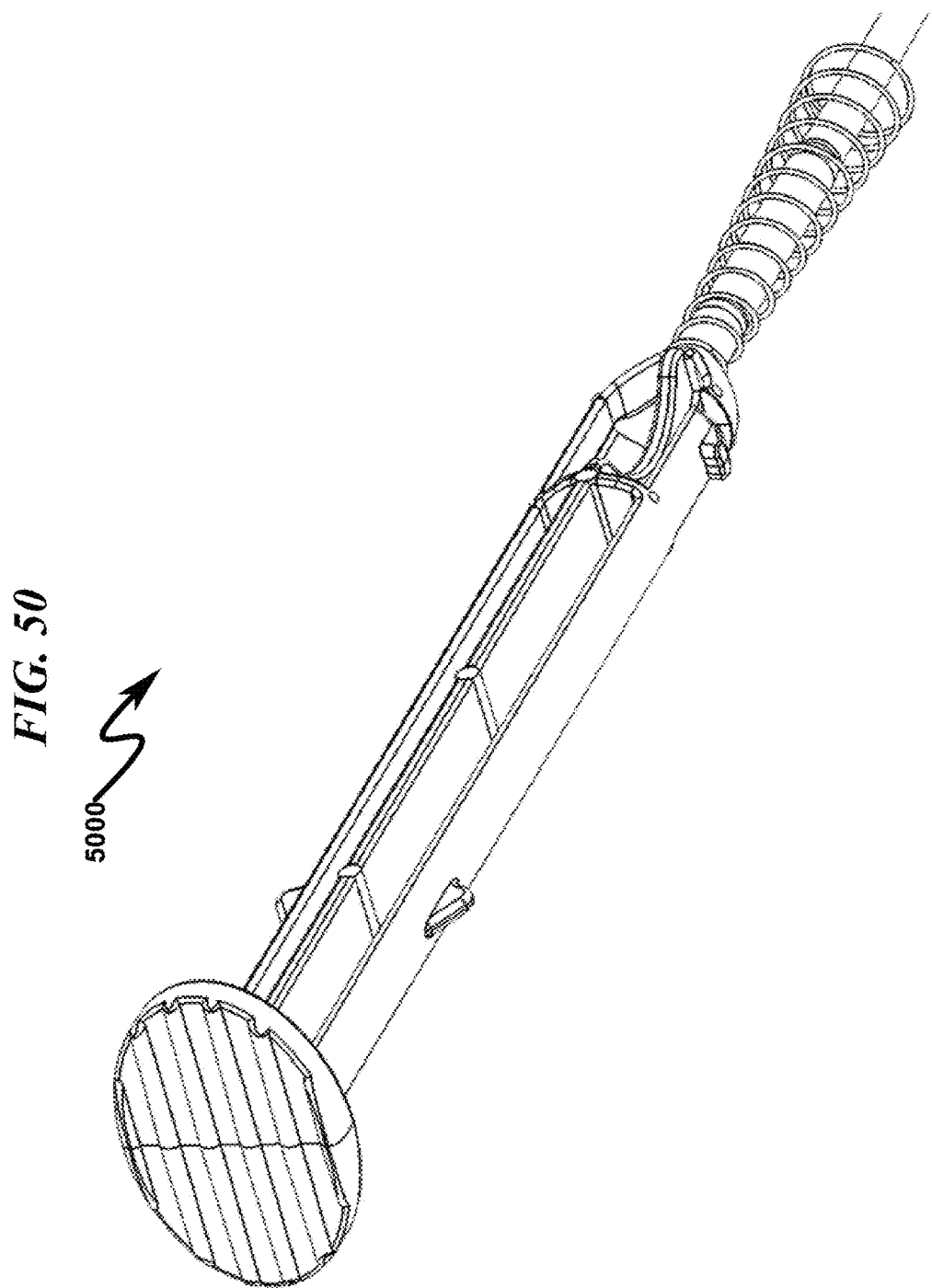
FIG. 50 illustrates a side perspective view of an injector assembly useful in some exemplary embodiments of the present invention.
Figure 51:
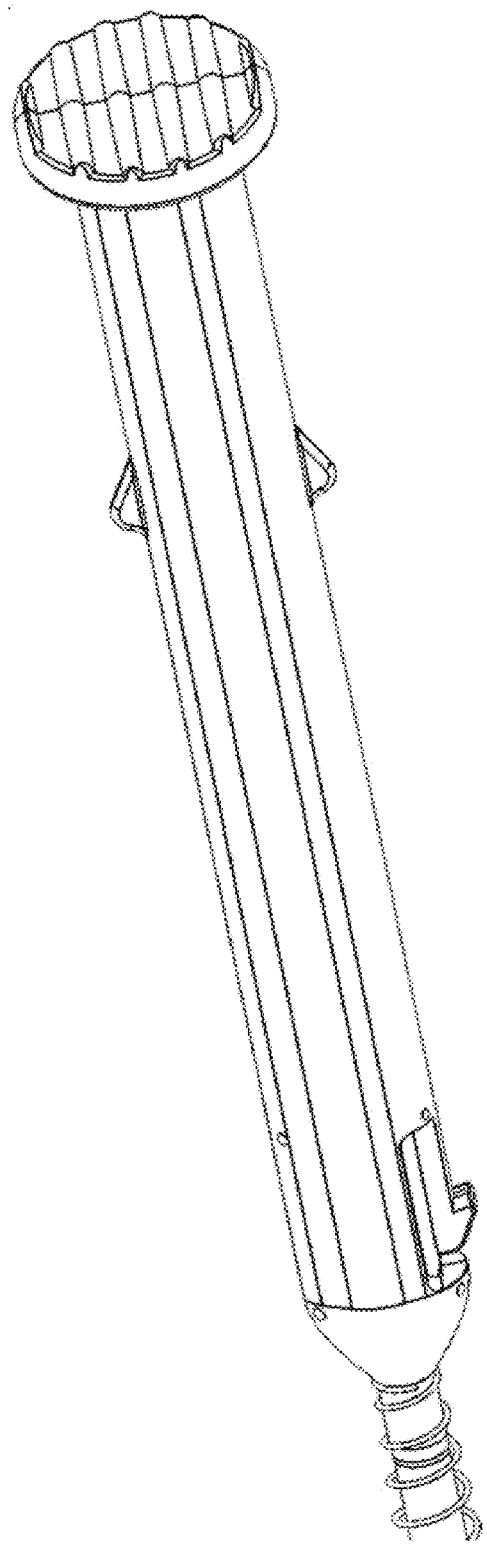
FIG. 51 illustrates an end perspective view of an injector assembly useful in some exemplary embodiments of the present invention.
Figure 52:
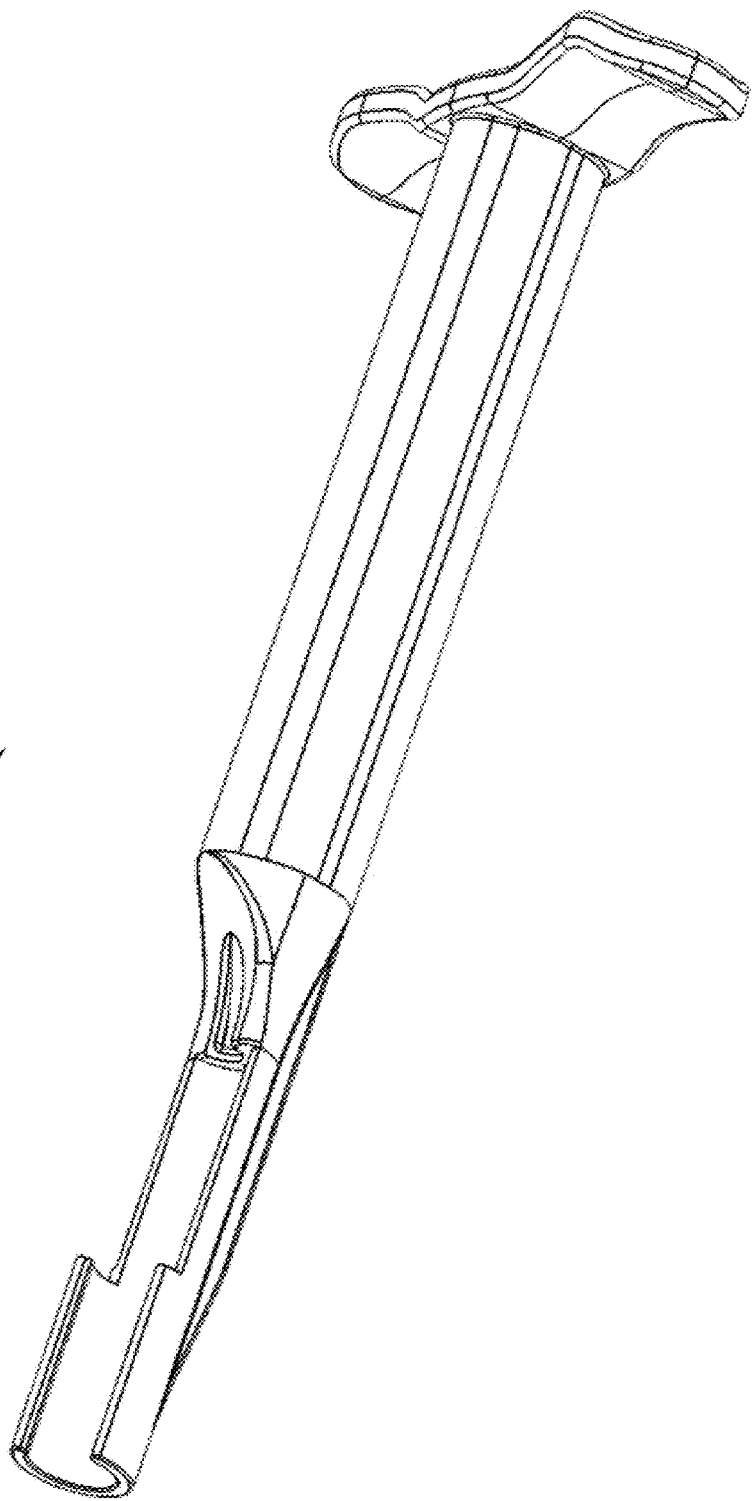
FIG. 52 illustrates a side perspective view of a handle assembly useful in some exemplary embodiments of the present invention.
Figure 53:
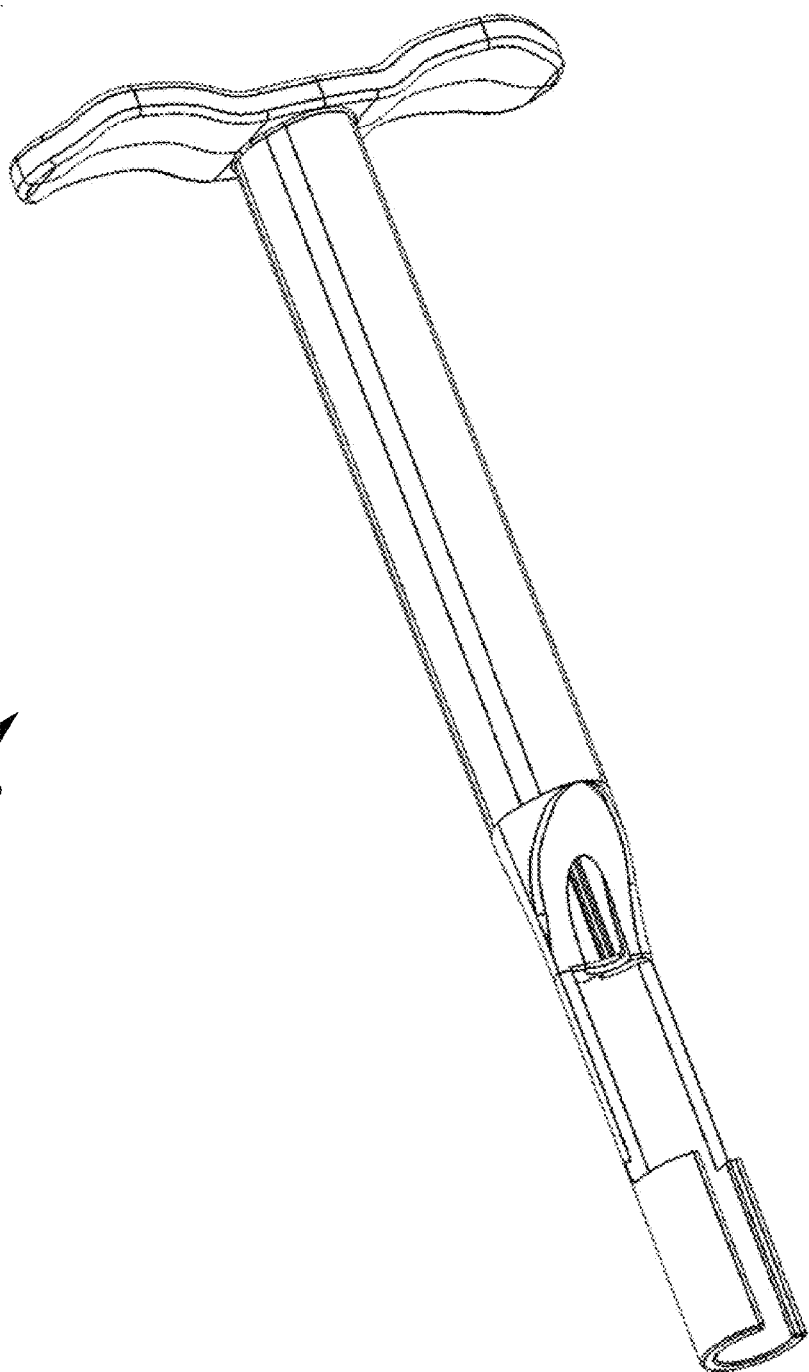
FIG. 53 illustrates a top perspective view of a handle assembly useful in some exemplary embodiments of the present invention.

Details of the plunger injector assembly are provided in FIG. 49 (4900)-FIG. 51 (5100) and provide a reference to how the plunger tip is used to press against the IOL to place it in a compressed state. The illustrated spring and locking tabs on the plunger operate with the handle (illustrated in FIG. 52 (5200)-FIG. 53 (5300)) to retain the IOL in a compressed state once the plunger is depressed within the body of the handle.

Figure 54:
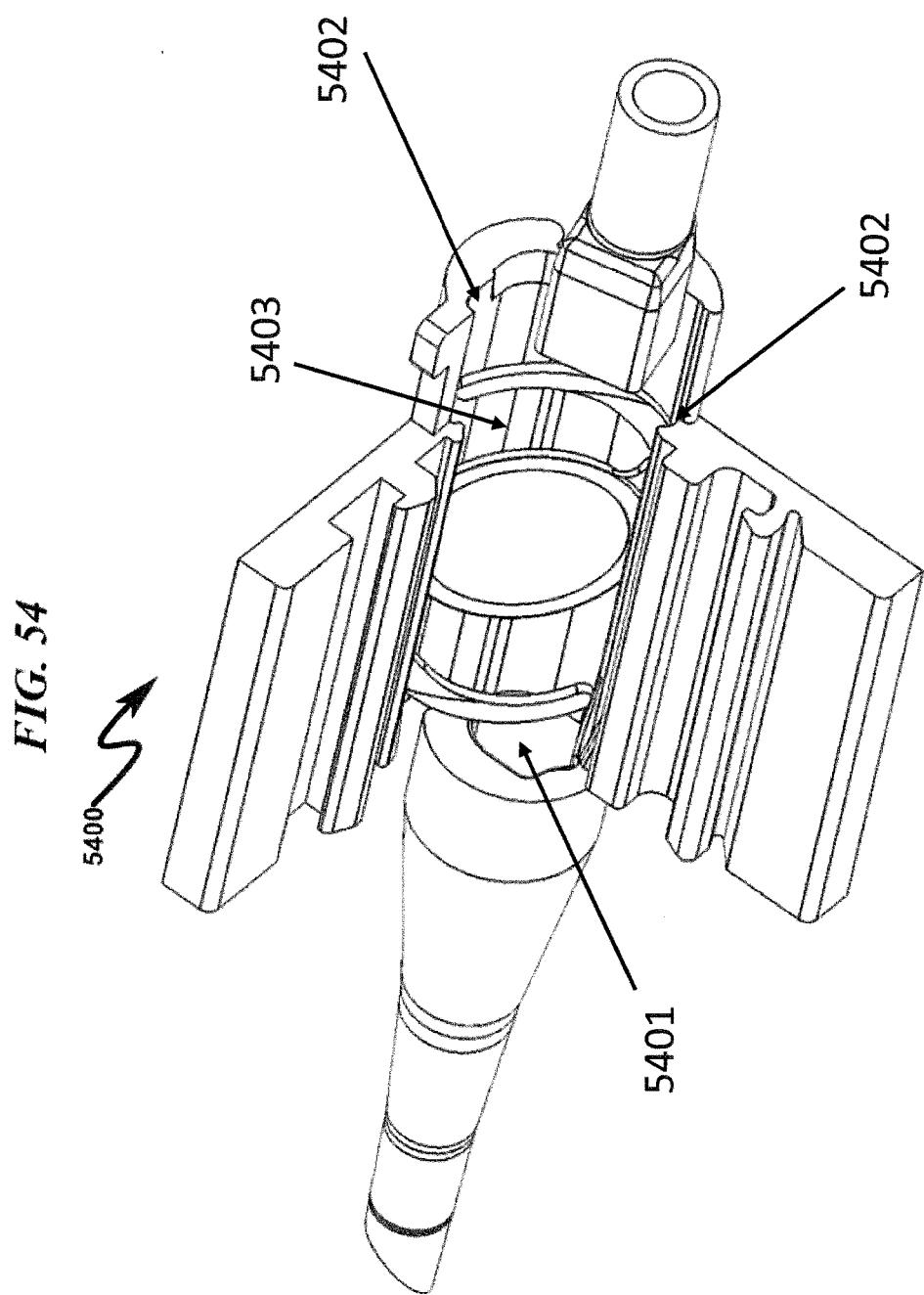
FIG. 54 illustrates a side perspective view of an IOL cartridge assembly useful in some exemplary embodiments of the present invention.
Figure 55:
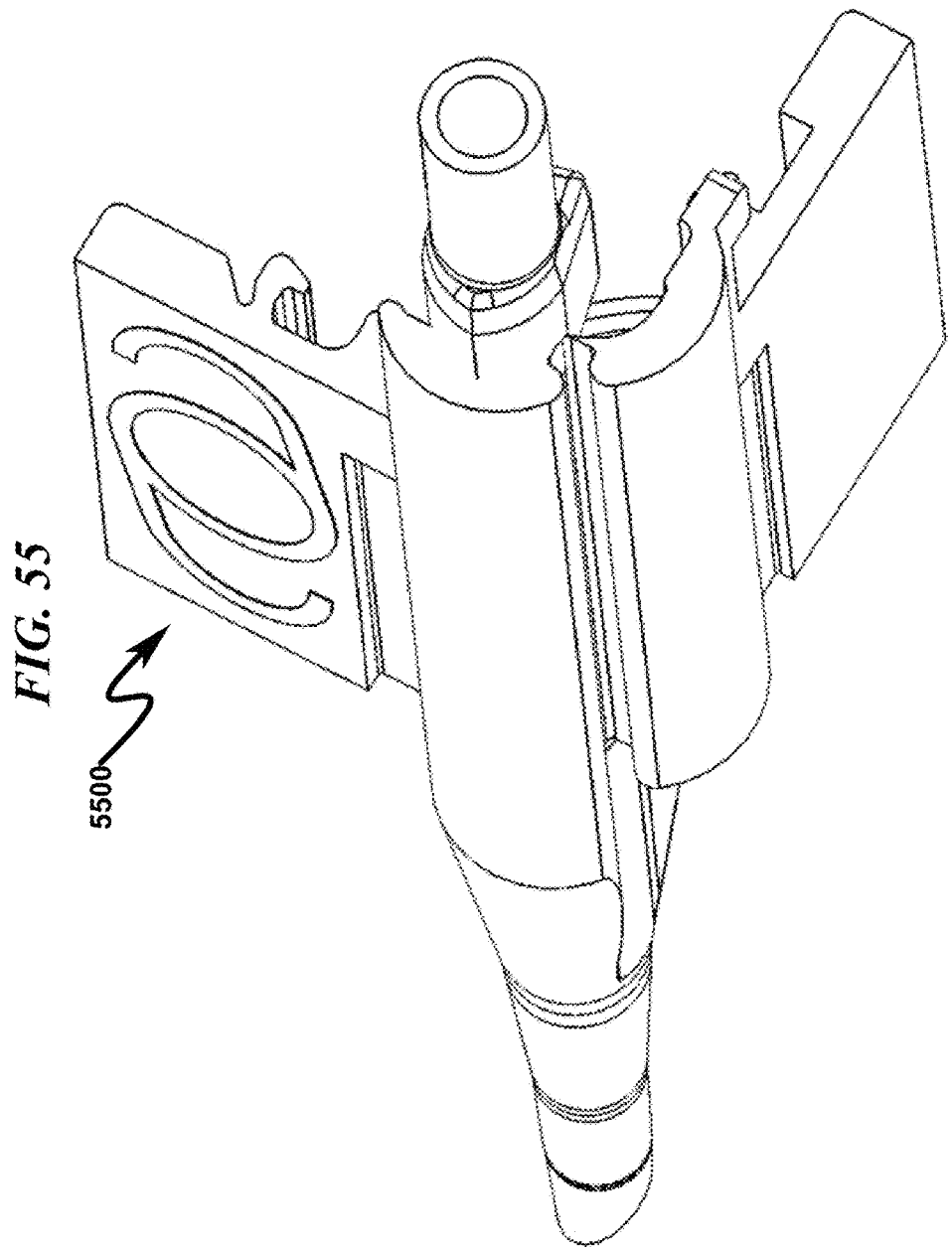
FIG. 55 illustrates a side perspective view of an IOL cartridge assembly useful in some exemplary embodiments of the present invention.
Figure 56:
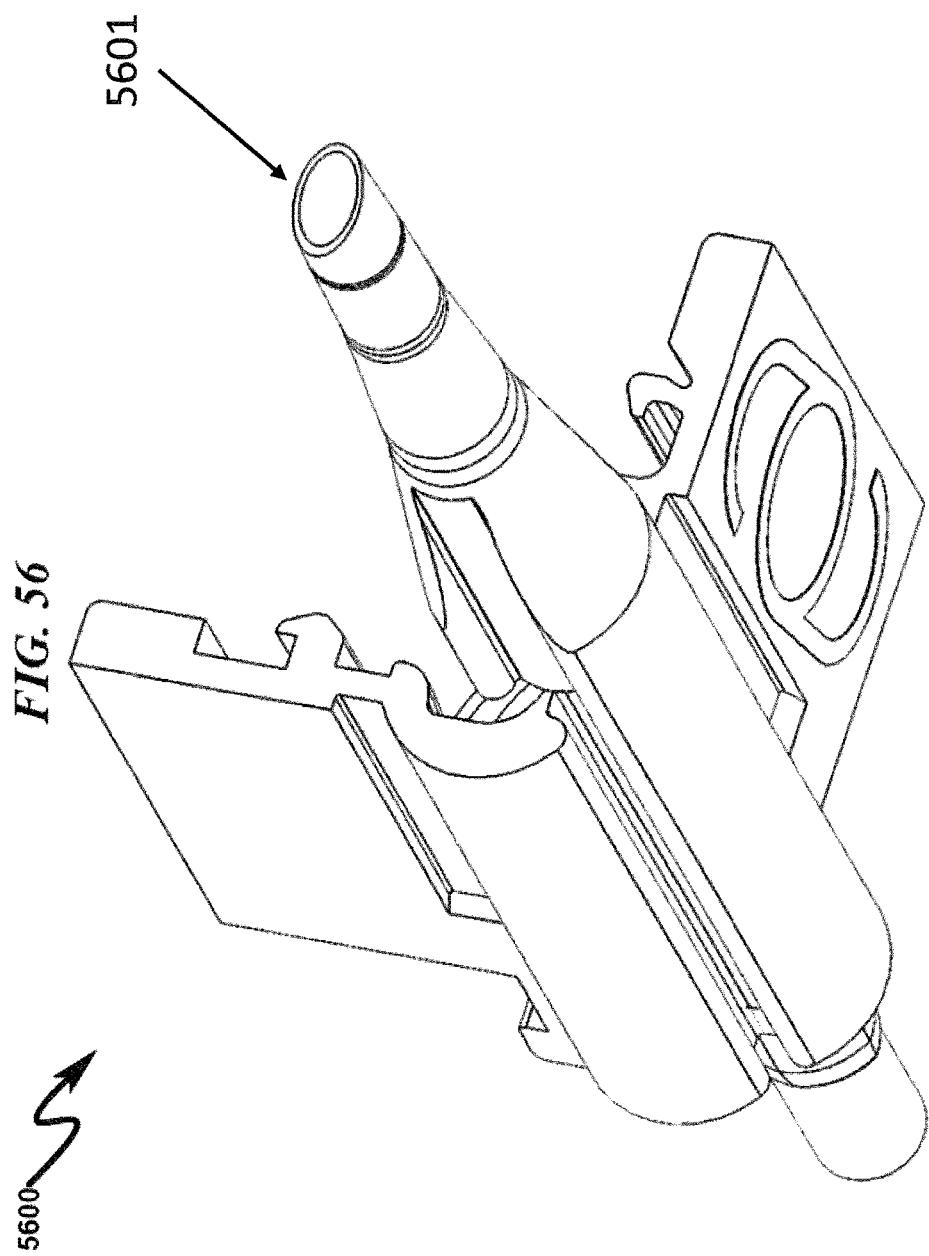
FIG. 56 illustrates a bottom perspective view of an IOL cartridge assembly useful in some exemplary embodiments of the present invention.
Figure 57:
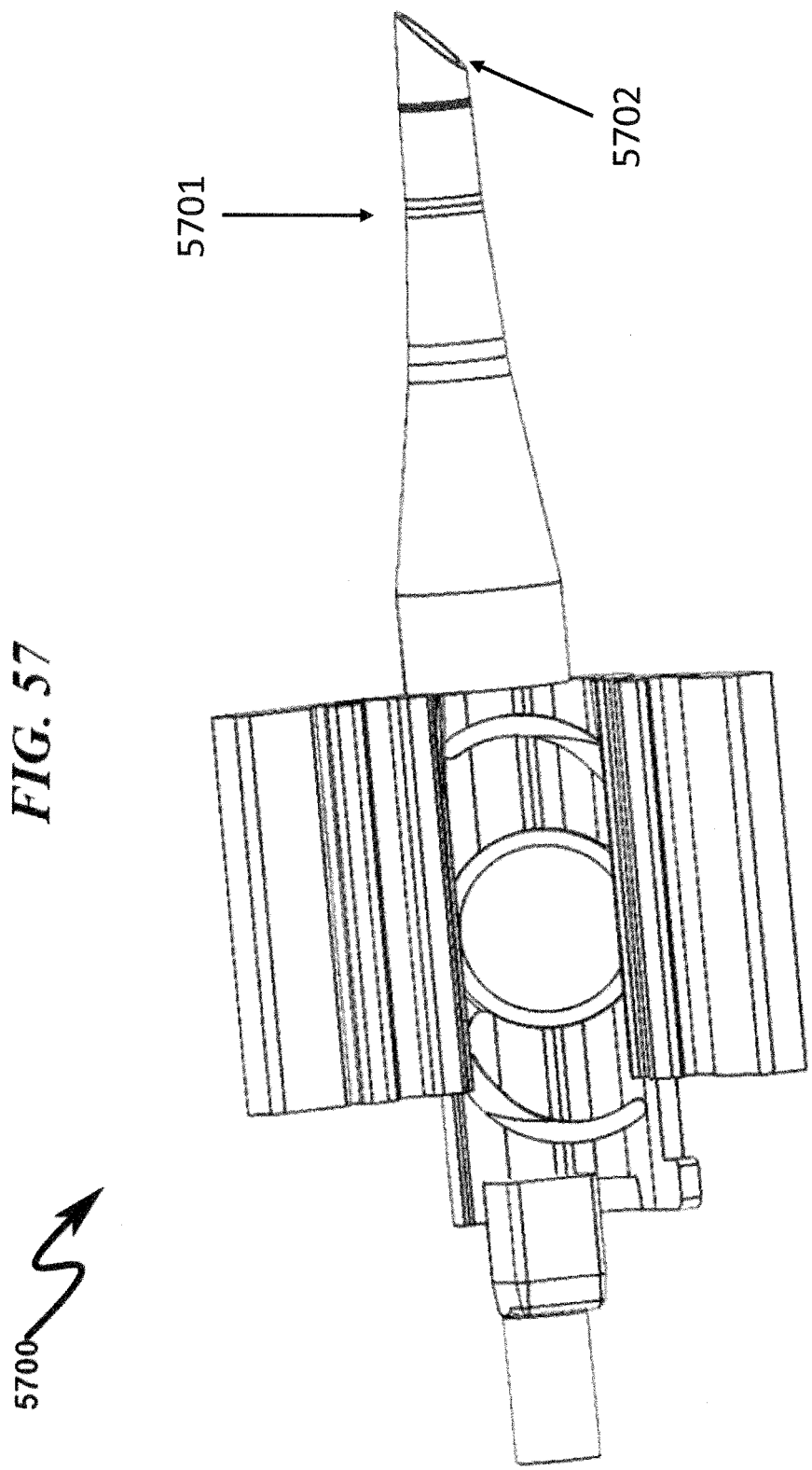
FIG. 57 illustrates a top perspective view of an IOL cartridge assembly useful in some exemplary embodiments of the present invention and illustrates the haptics in an uncompressed state prior to final manufacture.
Figure 58:
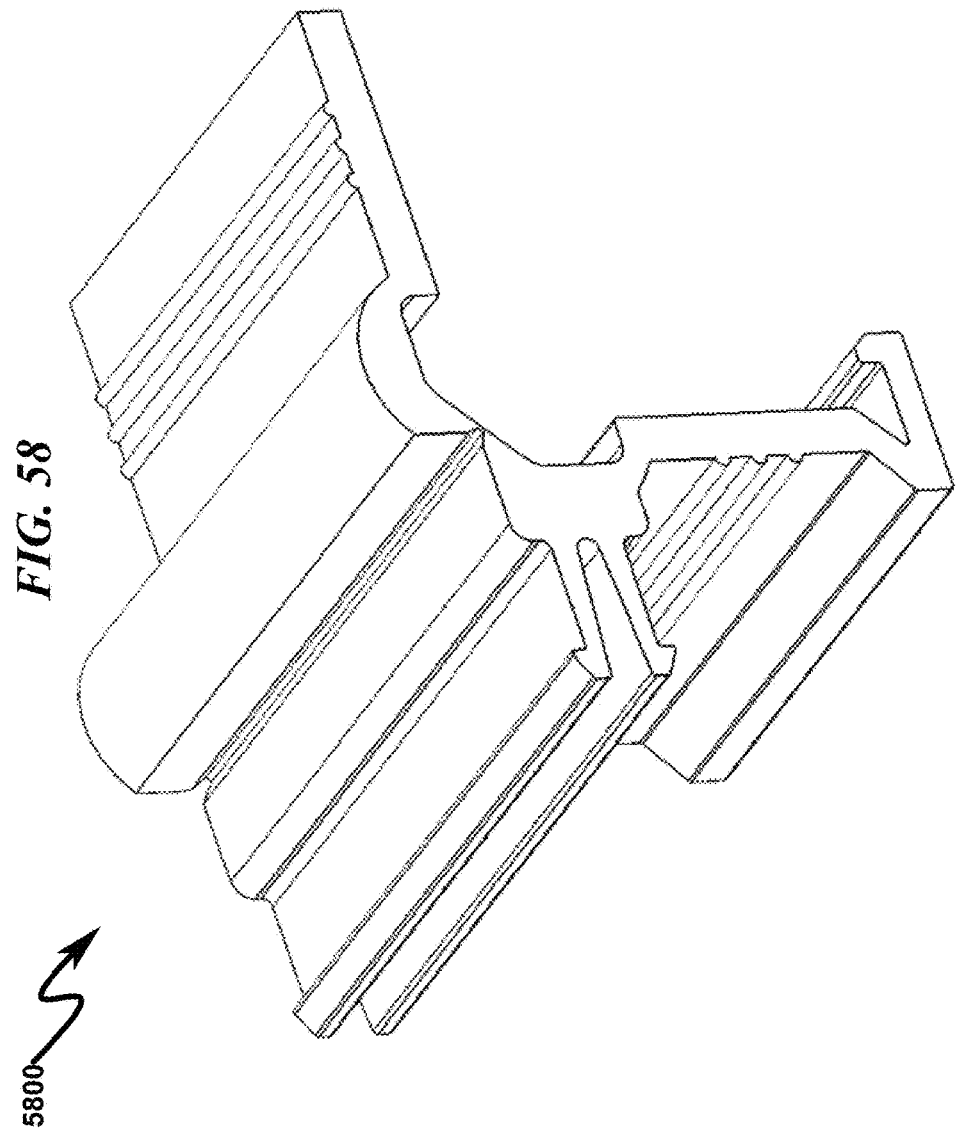
FIG. 58 illustrates a side perspective view of an IOL lens holding chamber useful in some exemplary embodiments of the present invention.
Figure 59:
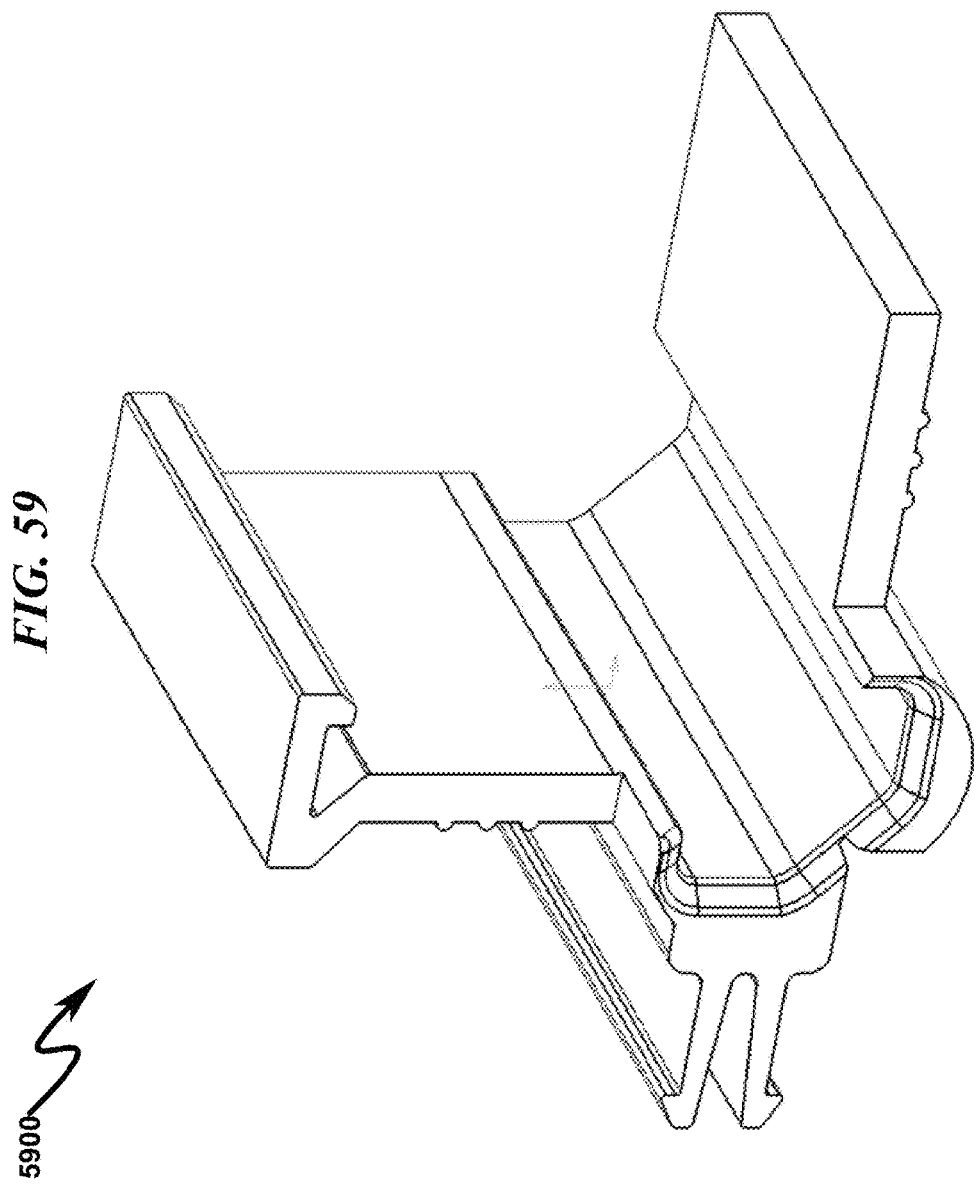
FIG. 59 illustrates a side perspective view of an IOL lens holding chamber useful in some exemplary embodiments of the present invention.
Figure 60:
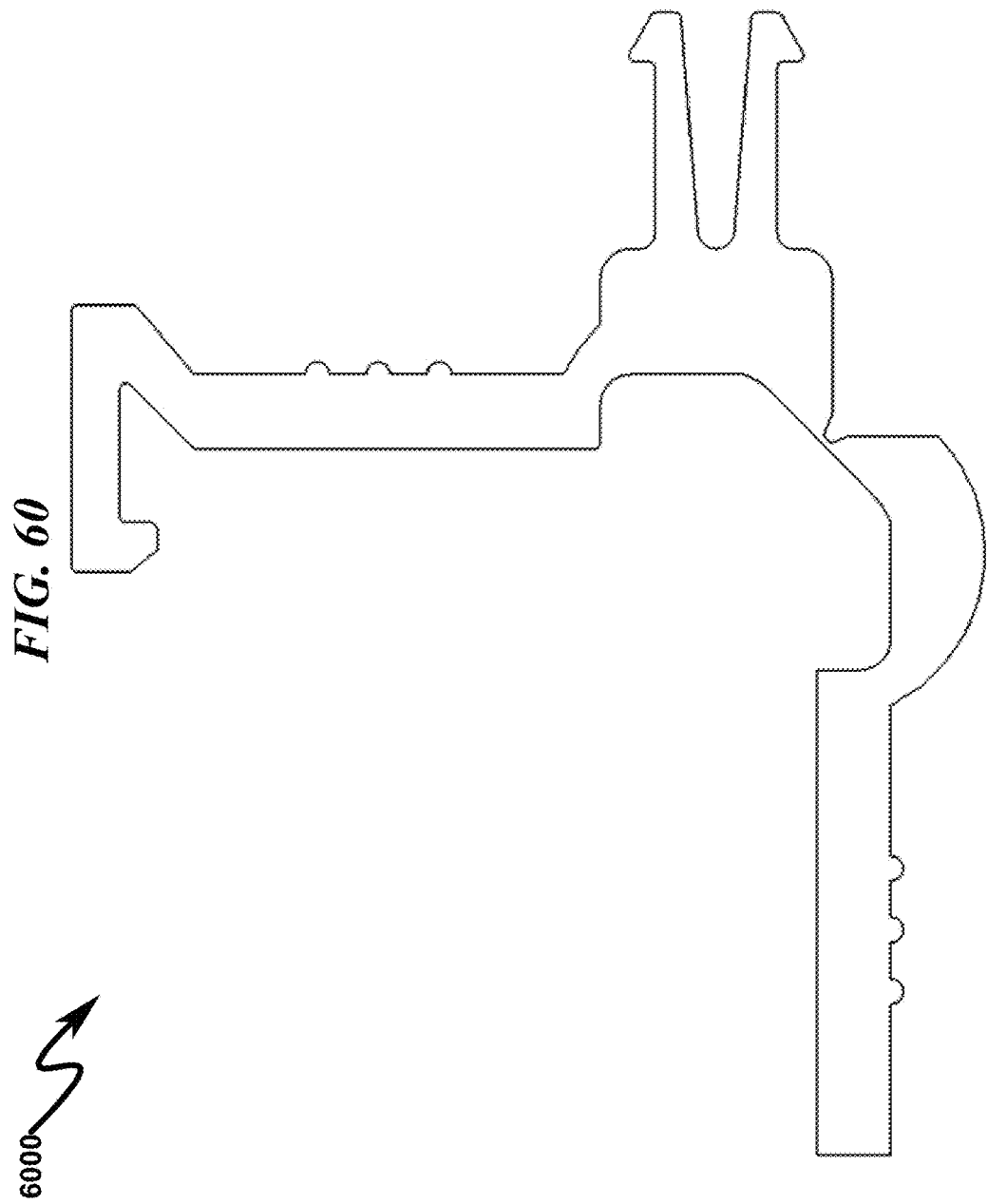
FIG. 60 illustrates a top view of an IOL lens holding chamber useful in some exemplary embodiments of the present invention.

FIG. 54 (5400)-FIG. 57 (5700) illustrate various views of the assembled placement tip (lumen), cartridge, IOL, and plunger injector tip that depresses the IOL into a compressed state. Note that FIG. 57 (5700) illustrates the IOL in an uncompressed state prior to final manufacturing in which the haptics are compressed within the lens holding chamber. FIG. 58 (5800)-FIG. 61 (6100) illustrate various views of lens holding chamber used to contain the IOL during shipment and injection.

IOL Packaging

The present invention permits the IOL to be configured to achieve consistent lens orientation during the manufacturing/packaging operation as follows. A manufacture worker advances the plunger to compress the haptic of a lens as shown in FIG. 11 (1100). At this position, the plunger has a structure which engages with the injector body to temporarily lock the plunger in this position for shipping and storage prior to surgery.

One of the embodiments for this temporary locking mechanism of the present invention is the coordination between the plunger and the injector body. The plunger has a mechanic structure (shown in FIG. 49 (4900)-FIG. 51 (5100)) which is designed for engaging into the properly sized hole in the injector handle body (FIG. 52 (5200)-FIG. 53 (5300)). When the plunger is moved forwarded reaching a desired distance for the haptic-to-haptic diameter, the mechanical structure of the plunger just arrives at the hole position of the injector body. When this happens, the operator will hear a click sound indicating that the plunger is engaged with the injector body such that the plunger cannot move backwards but it can move forward with an increased initial forward force for disengaging the lock mechanism. Without this increased initial forward force, the plunger stays in this temporarily locked position for maintaining the haptic wrapping of the lens in the cartridge.

This structure permits the IOL to be delivered in a consistent orientation FROM THE FACTORY as compared to prior art techniques which require that the IOL delivery of the folded lens to be performed by the surgeon MANUALLY PRIOR TO PLACEMENT. Thus, a significant advantage of the present invention is that the placement orientation of the IOL is determined during LOADING of the lens and is NOT a parameter that the surgeon can adjust (or determine) during the placement operation. This prevents incorrect IOL placement orientation that may occur due to lens rotation during the placement procedure. The IOL generally does not rotate during the Wrapping Process. It may, however, rotate during the injection or placement process and this is a prevention goal of the present invention.

Preloaded IOL Method

The present invention method anticipates a wide variety of variations in the basic theme of implementation, but can be generalized as a preloaded IOL method comprising:
(1) preloading an IOL within a cartridge or a lens holding portion of a preload system in a compressed state; and
(2) activating a plunger on an IOL preloaded system containing the preloaded IOL to transport the compressed IOL through the lumen of the preloading system into the eye of a patient and placing the IOL within said eye.

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

General Precautions

While not limitive of the present invention scope, the following precautions are generally applicable to the IOL placement procedure and handling/packaging of the IOL:
Indications: IOLs are intended for primary implantation in the posterior chamber in patients where a cataractous lens has been removed by cataract extraction. It is recommended that the use of the intraocular lens be initially limited to one eye. Use of the lenses is especially appropriate in patients who cannot tolerate contact lenses, those who would not be candidates for cataract spectacles, or for patients requiring an intraocular lens for occupational or other reasons.
The IOL should not be autoclaved.
The IOL should not be re-sterilize by any method.
The IOL injector should not be re-sterilized/prepared. These components should be single use only.
The IOL should be stored at room temperature.
The IOL should not be frozen or left in sunlight.
Use only sterile balanced salt solution for rinsing or soaking of the IOL.
A high level of surgical skill is required for IOL implantation. A surgeon should have observed and/or assisted on numerous surgical implantations and successfully completed one or more courses on IOL implantation before attempting to implant an IOL.
Lens Power Calculation: The power of the IOL to be implanted should be determined preoperatively. The following references provide lens power calculation methods: Binkhorst, R. D.: Intraocular Lens Power Calculation Manual, New York, Richard D. Binkhorst, 1978; Retzlaff J., Sanders D., and Kraft M.: A Manual of Implant Power Calculation.
Operational Procedure. The appropriate surgical techniques are the responsibility of the respective surgeon. He or she must assess the appropriateness of the relevant procedure based on his or her education and experience.
How Supplied. The IOL should optimally be supplied as sterile, non-pyrogenic in its own medical device tray. Sterility should be assured provided the medical device tray seal has not been compromised or the medical device tray has not been punctured.
Expiration Date: The expiration date should be clearly indicated on the outside of the box containing the IOL/injector.

One skilled in the art will recognize that these precautions may vary widely based on the particular application and are provide only as an exemplary guide to best practices when implementing the teachings of the present invention with respect to the IOL system and method disclosed herein.

Exemplary IOL Placement Process (6200)-(6400)

The present invention anticipates that a variety of IOL placement methodologies may be utilized to place IOLs that have been "pre-compressed" during manufacture (and subsequently shipped as such) to the physician for placement in a patient's eye. One such method is generally illustrated in the flowcharts of FIG. 62 (6200)-FIG. 63 (6300) and the corresponding instructional diagram provided in FIG. 64 (6400).

Figure 64:
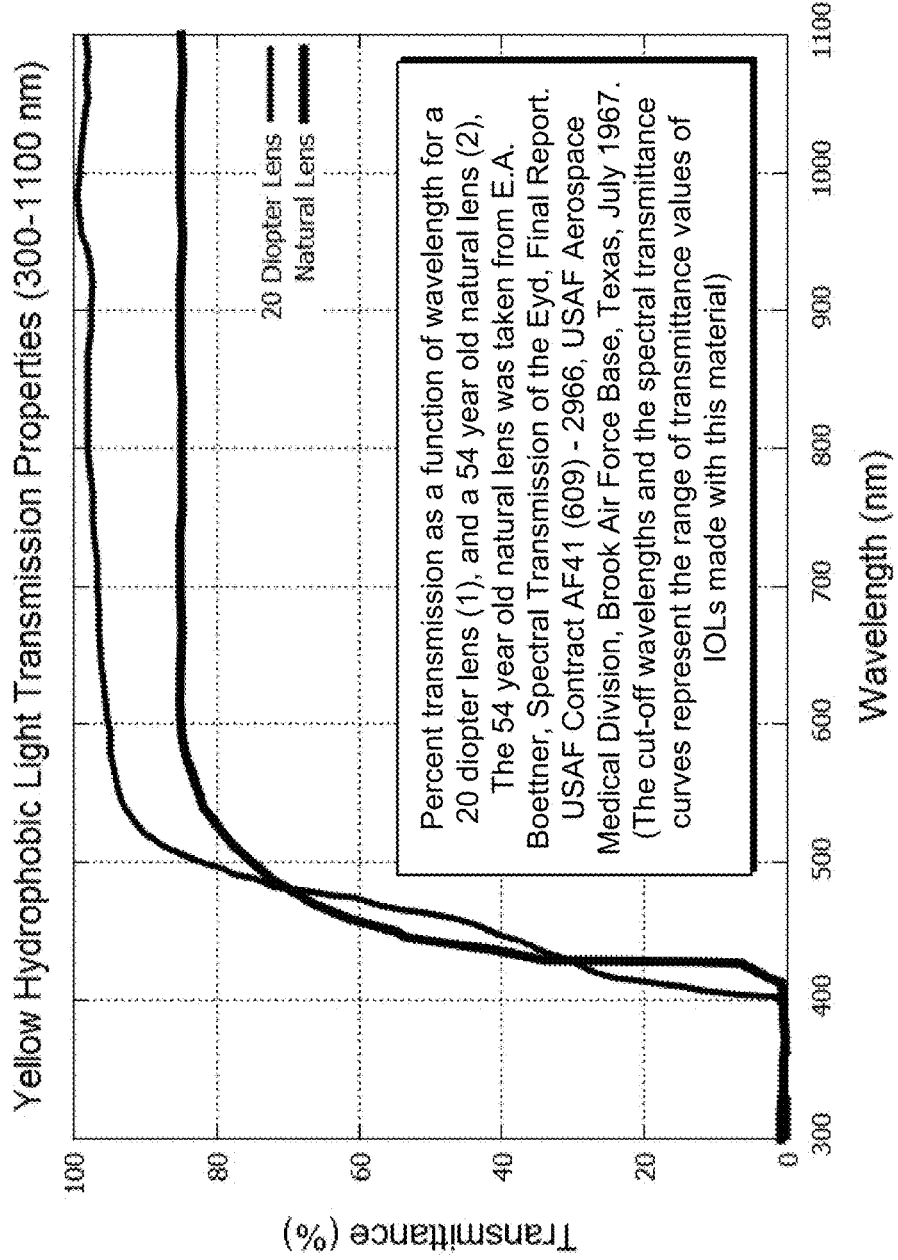
FIG. 64 illustrates an exemplary IOL characteristic useful in implementing some preferred IOL placement embodiments taught by the present invention.

While many forms of IOL are anticipated to be utilized in this exemplary placement process, an exemplary IOL performance characteristic is generally illustrated in FIG. 64 (6400). This exemplary IOL is indicated as a Heparin Surface Modified UV light-absorbing Posterior Chamber Yellow Hydrophobic Acrylic Lens that is designed to be implanted in the capsular bag following extracapsular cataract extraction. This exemplary optic is biconvex design. It may be constructed from an optically clear yellow hydrophobic acrylic material which incorporates an UV-absorbing component and has a refractive index of approximately 1.49.

Figure 62:
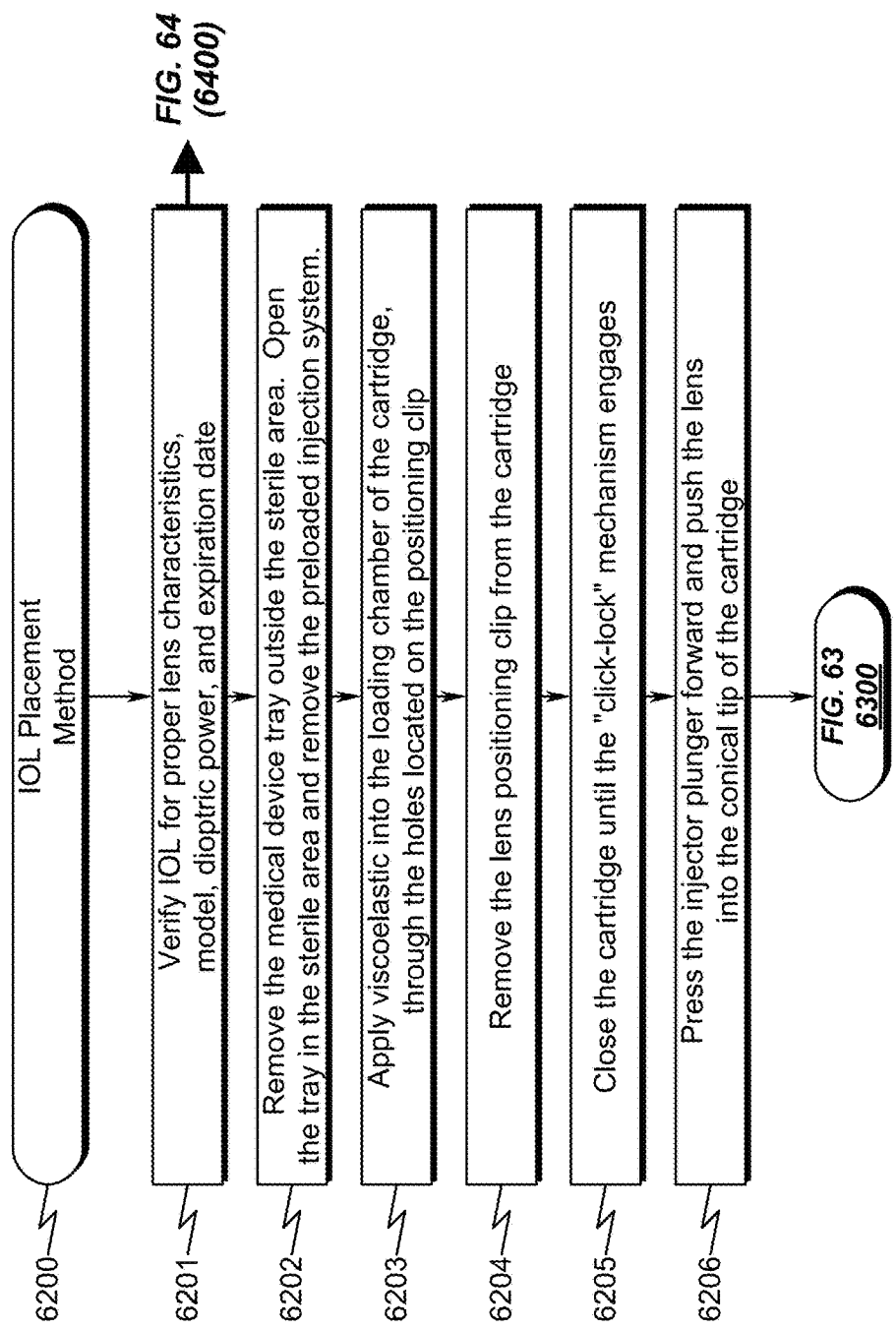
FIG. 62 illustrates an exemplary method flowchart useful in implementing a preferred IOL placement process.
Figure 63:
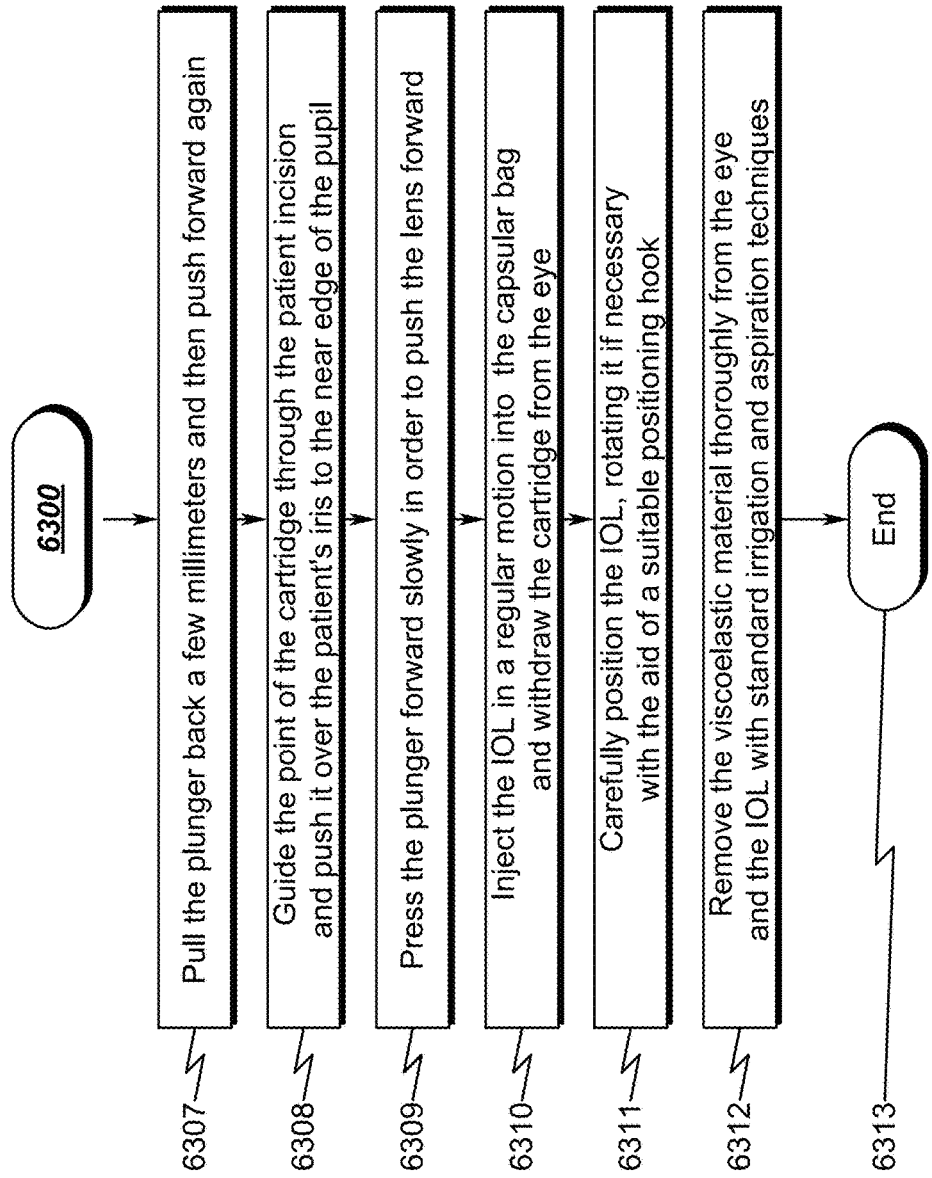
FIG. 63 illustrates an exemplary method flowchart useful in implementing a preferred IOL placement process.

The present invention IOL placement method anticipates a wide variety of variations in the basic theme of implementation, but can be generalized as depicted in FIG. 62 (6200)-FIG. 63 (6300) (with corresponding detail instructional diagram in FIG. 64 (6400)) as a preloaded IOL method comprising the following steps:
(1) Verify the label on the IOL container box for proper lens model, dioptric power, and expiration date (6201).
(2) Remove the medical device tray outside the sterile area. Open the tray in the sterile area and remove the preloaded injection system (6202). Note that in contrast to traditional injection systems, the IOL placement system has the cartridge integrated in the injector.
(3) Apply a generous amount of viscoelastic into the loading chamber of the cartridge, through the holes located on the positioning clip (6203).
(4) Remove the lens positioning clip from the cartridge (6204).
(5) Close the cartridge. Once the "click-lock" mechanism engages, the lens is securely loaded and ready for injection (6205). The lens should be injected within 5 minutes after loading. Note that viscoelastic materials may lose their lubricity if allowed to stand too long while exposed to air.
(6) Press the injector plunger forward and push the lens into the conical tip of the cartridge (6206).
(7) Pull the plunger back a few millimeters and then push forward again (6307). This step ensures that the lens is always grasped correctly.
(8) Guide the point of the cartridge through the patient incision and push it over the patient's iris to the near edge of the pupil (6308).

(9) Press the plunger forward slowly in order to push the lens forward (6309).
(10) Inject the IOL in a regular motion into the capsular bag and withdraw the cartridge from the eye (6310).
(11) Carefully position the IOL, rotating it if necessary with the aid of a suitable positioning hook (6311).
(12) Remove the viscoelastic material thoroughly from the eye and the IOL with standard irrigation and aspiration techniques (6312).

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

Preferred Embodiment System Summary

The present invention preferred exemplary system embodiment anticipates a wide variety of variations in the basic theme of construction, but can be generalized as a preloaded intraocular lens (PIOL) system comprising:
(a) intraocular lens (IOL);
(b) lens holding chamber;
(c) lumen; and
(d) injector;
wherein
the IOL comprises haptics that are wrapped around the IOL in a coplanar manner during the manufacturing of the IOL;
the lens holding chamber is configured to store the IOL a compressed state after the manufacturing of the IOL;
the lumen is directly connected to the lens holding chamber and gradually become taped leading to a distal opening end;
the lumen is configured for gradually folding the lens into a smaller configuration so that it can be injected out from the distal opening end; and
the injector further comprises an injector body which is connected with the lens holding chamber and a plunger which directly contacts the lens and exerts forwarding force onto the lens for injecting the lens though the lumen into a patient's eye.

Alternate Preferred Embodiment System Summary

Another preferred exemplary embodiment of the present invention system comprises:
(a) intraocular lens (IOL);
(b) lens holding chamber;
(c) lumen; and
(d) injector;
wherein
the IOL comprises haptics that are wrapped around the IOL in a coplanar manner during the loading of the IOL in the lens holding chamber;
the lens holding chamber is configured such that the lens may be shipped and stored in a compressed state after the loading of the IOL; and
the lumen comprises a input tube portion leading to a distal opening end wherein the lens is delivered into a the eye of a patient upon activation of the injector.

Alternate Preferred Embodiment System Summary

Another preferred exemplary embodiment of the present invention system comprises:
(a) intraocular lens (IOL);
(b) cartridge; and
(c) injector;
wherein
the IOL comprises haptics that are wrapped around the IOL in a coplanar manner during the manufacturing of the IOL;
the cartridge further comprises a lens holding portion, which is configured to store the IOL in a compressed state and to fold the lens into a folded state, and a tube portion leading to a distal opening end wherein a folded lens is delivered into a patient's eye;
the injector further comprises an injector body which is configured to receive the cartridge and a plunger which directly contacts the lens and exerts forwarding force onto the lens for injecting the lens though distal opening end into a patient's eye.

This general system summary may be augmented by the various elements described herein to produce a wide variety of invention embodiments consistent with this overall design description.

Preferred Embodiment Method Summary

The present invention preferred exemplary method embodiment anticipates a wide variety of variations in the basic theme of implementation, but can be generalized as a preloaded intraocular lens (PIOL) method, the method operating in conjunction with a preloaded intraocular lens (PIOL) system comprising:
(a) intraocular lens (IOL);
(b) lens holding chamber;
(c) lumen; and
(d) injector;
wherein
the IOL comprises haptics that are wrapped around the IOL in a coplanar manner during the manufacturing of the IOL;
the lens holding chamber is configured to store the IOL a compressed state after the manufacturing of the IOL;
the lumen is directly connected to the lens holding chamber and gradually become taped leading to a distal opening end;
the lumen is configured for gradually folding the lens into a smaller configuration so that it can be injected out from the distal opening end; and
the injector further comprises an injector body which is connected with the lens holding chamber and a plunger which directly contacts the lens and exerts forwarding force onto the lens for injecting the lens though the lumen into a patient's eye;
wherein the method comprises the steps of:
(1) preloading the IOL within the cartridge (or lens holding chamber) in a compressed state; and
(2) activating a plunger to transport the compressed IOL through the lumen into the eye of a patient and placing the IOL within the eye.

One skilled in the art will recognize that these method steps may be augmented or rearranged without limiting the teachings of the present invention. This general method summary may be augmented by the various elements described herein to produce a wide variety of invention embodiments consistent with this overall design description.

This method operates similar to that of the Prior Art depicted in FIG. 1 (0100) with the exception that that the lens haptics are compressed at the factory and not in the field. As the lens with compressed haptics passes the lumen, the lumen deforms the lens shape into a small profile gradually out from distal opening.

Alternate Preferred Embodiment Method Summary

An alternate present invention preferred exemplary method embodiment anticipates a wide variety of variations in the basic theme of implementation, but can be generalized as a preloaded intraocular lens (PIOL) method, the method operating in conjunction with a preloaded intraocular lens (PIOL) system comprising:
  (a) intraocular lens (IOL);
  (b) lens holding chamber;
  (c) lumen; and
  (d) injector;
  wherein
  the IOL comprises haptics that are wrapped around the IOL in a coplanar manner during the loading of the IOL in the lens holding chamber;
  the lens holding chamber is configured such that the lens may be shipped and stored in a compressed state after the loading of the IOL; and
  the lumen comprises a input tube portion leading to a distal opening end wherein the lens is delivered into a the eye of a patient upon activation of the injector;
  wherein the method comprises the steps of:
  (1) preloading the IOL within the cartridge (or lens holding chamber) in a compressed state; and
  (2) activating a plunger to transport the compressed IOL through the lumen into the eye of a patient and placing the IOL within the eye.
One skilled in the art will recognize that these method steps may be augmented or rearranged without limiting the teachings of the present invention. This general method summary may be augmented by the various elements described herein to produce a wide variety of invention embodiments consistent with this overall design description.

Alternate Preferred Embodiment Method Summary

An alternate present invention preferred exemplary method embodiment anticipates a wide variety of variations in the basic theme of implementation, but can be generalized as a preloaded intraocular lens (PIOL) method, the method operating in conjunction with a preloaded intraocular lens (PIOL) system comprising:
  (a) intraocular lens (IOL);
  (b) cartridge;
  (c) injector;
  wherein
  the IOL comprises haptics that are wrapped around the IOL in a coplanar manner during the manufacturing of the IOL;
  the cartridge further comprises a lens holding portion which is configured to store the IOL a compressed state after the manufacturing of the IOL and a lumen portion leading to a distal opening end wherein a folded lens is delivered into a patient's eye
  wherein the method comprises the steps of:
  (3) preloading the IOL within the cartridge (or lens holding chamber) in a compressed state; and
  (4) activating a plunger to transport the compressed IOL through the lumen into the eye of a patient and placing the IOL within the eye.
One skilled in the art will recognize that these method steps may be augmented or rearranged without limiting the teachings of the present invention. This general method summary may be augmented by the various elements described herein to produce a wide variety of invention embodiments consistent with this overall design description.

This method operates similar to that of the Prior Art depicted in FIG. 1 (0100) with the exception that that the lens haptics are compressed at the factory and not in the field and the cartridge comprises a loading chamber and lumen. As the lens with compressed haptics passes the lumen, the lumen deforms the lens shape into a small profile gradually out from distal opening.

Preloaded IOL Method

The present invention method anticipates a wide variety of variations in the basic theme of implementation, but can be generalized as a preloaded IOL method comprising:
  (1) preloading an IOL within a cartridge or lens holding chamber in a compressed state; and
  (2) activating a plunger on an IOL preloaded system containing the preloaded IOL to transport the compressed IOL through the lumen of the preloading system into the eye of a patient and placing the IOL within the eye.
This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

Preferred Embodiment IOL Product-by-Process

The present invention anticipates a preloaded intraocular lens (IOL) product-by-process as within the overall invention scope, wherein the product-by-process is created using a preloaded intraocular lens (IOL) formation process comprising:
  (1) wrapping haptics around the IOL in a coplanar manner during the manufacturing of the IOL;
  (2) storing the IOL a compressed within an IOL delivery system, the system comprising:
    (a) lens holding chamber;
    (b) lumen; and
    (c) injector;
    wherein
    the IOL comprises haptics that are wrapped around the IOL in a coplanar manner during the loading of the IOL in the lens holding chamber;
    the lens holding chamber is configured such that the lens may be shipped and stored in a compressed state after the loading of the IOL; and
    the lumen comprises a input tube portion leading to a distal opening end wherein the lens is delivered into a the eye of a patient upon activation of the injector.
This general product formation methodology may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

System/Method/Product-by-Process Variations

The present invention anticipates a wide variety of variations in the basic theme of construction. The examples presented previously do not represent the entire scope of possible usages. They are meant to cite a few of the almost limitless possibilities.

This basic system, method, and product-by-process may be augmented with a variety of ancillary embodiments, including but not limited to:

An embodiment wherein the cartridge comprises internal rails inside the lens holding chamber on which the IOL rests.

An embodiment wherein the cartridge further comprises a hinge that comprises wings configured to be opened for receiving the IOL or closed for folding the IOL.

An embodiment wherein the cartridge is configured such that when the IOL is positioned in the rails the central portion of the IOL does not touch the hinge.

An embodiment wherein the injector provides a means for compressing the haptic bodies of the IOL and for holding the IOL in a compressed configuration.

An embodiment wherein the haptic-to-haptic distance of the compressed IOL ranges from 7 mm to 12 mm.

An embodiment wherein the haptic-to-haptic distance of the compressed IOL ranges from 9 mm to 11 mm.

An embodiment wherein the IOL comprises AAREN SCIENTIFIC ACRYLMEX hydrophobic acrylic polymer.

An embodiment wherein the IOL comprises a cross-linked hydrophilic acrylic polymer.

An embodiment wherein the IOL comprises water in the range of 20% to 30%.

An embodiment wherein the IOL comprises water in the range of 24% to 27%.

An embodiment wherein the IOL comprises a UV absorber.

An embodiment wherein the IOL comprises a yellow dye.

An embodiment wherein the IOL comprises a cross-linked hydrophobic acrylic polymer, the cross-linked hydrophobic polymer comprising a cross-linker comprising a weight percentage in the range of 1% to 6%.

An embodiment wherein the cartridge further comprises a lock mechanism configured to provide a means for maintaining the IOL in a folded state.

An embodiment wherein the injector further comprises an injector body that retains the cartridge in place and a plunger shaft 4903 further comprising a soft cushion 4901 connected to a plunger body 4902.

An embodiment wherein the plunger is configured to be temporarily locked into the injector body in a pre-determined position.

An embodiment wherein the lens holding chamber and the lumen are directly connected and are configured to allow the lens to gradually decrease in profile as the lens passes through the lumen.

One skilled in the art will recognize that other embodiments are possible based on combinations of elements taught within the above invention description.

CONCLUSION

A preloaded intraocular lens (IOL) system/method utilizing haptic compression has been disclosed. The disclosed system/method utilizes an IOL packaged in a compressed state that is inserted into a patient using a cartridge and lumen through which the IOL is advanced. Within this context the haptics to the IOL are wrapped around the IOL in a coplanar fashion during the loading of the IOL to permit the IOL to be shipped and stored in a compressed state. This compressed state is achieve by wrapping the haptics of the IOL during the manufacturing process to ensure that the IOL is properly aligned and thus delivered in a predetermined orientation within the patient's eye. This compressed packaging of the IOL permits a more uniform and consistent placement of the IOL in the patient and eliminates the potential for physician error during the critical IOL placement procedure.

What is claimed is:

1. A preloaded intraocular lens system comprising:
(a) an intraocular lens (IOL) defining an optical axis and a center plane perpendicular to said optical axis;
(b) a lens holding chamber;
(c) a lumen; and,
(d) an injector;
said IOL having C-shaped haptics;
each of said haptics having an attached end attached to said IOL and a free end;
said haptics being compressed so as to cause said haptics with said free ends thereof to be compressed and thereby wrapped around said IOL in said center plane with said free ends remaining coplanar with said IOL,
said free ends of said haptics remaining coplanar with said IOL during the entire loading of said IOL into and while in said lens holding chamber;
said lens holding chamber having mutually adjacent walls for holding said IOL therebetween so as to permit said IOL to be shipped and stored with said haptics in a compressed state after said loading of said IOL;
said IOL being held in said compressed state by elastic forces created by said compressed haptics; and,
said lumen having an input tube portion leading to a distal opening end wherein said IOL is delivered into an eye of a patient upon activation of said injector.

2. The preloaded intraocular lens system of claim 1 wherein said lens holding chamber and said lumen are components of a cartridge and wherein said lens holding chamber has internal rails on which said IOL rests.

3. The preloaded intraocular lens system of claim 2 wherein said cartridge further includes a hinge having wings, said wings being configured to be opened for receiving said IOL or closed for folding said IOL.

4. The preloaded intraocular lens system of claim 3 wherein said cartridge is configured such that when said IOL is positioned in said rails, a central portion of said IOL does not touch said hinge of said cartridge.

5. The preloaded intraocular lens system of claim 2 wherein the haptic-to-haptic distance of said compressed IOL ranges from 7 mm to 12 mm.

6. The preloaded intraocular lens system of claim 5 wherein the haptic-to-haptic distance of said compressed IOL ranges from 9 mm to 11 mm.

7. The preloaded intraocular lens system of claim 2 wherein said IOL comprises a cross-linked hydrophobic acrylic polymer.

8. The preloaded intraocular lens system of claim 7 wherein said cross-linked hydrophobic polymer comprises a cross-linker in an amount of approximately 1% to 6% by weight.

9. The preloaded intraocular lens system of claim 8 wherein said IOL comprises a UV absorber.

10. The preloaded intraocular lens system of claim 9 wherein said IOL comprises a yellow dye.

11. The preloaded intraocular lens system of claim 2 wherein said IOL comprises a cross-linked hydrophilic acrylic polymer.

12. The preloaded intraocular lens system of claim 11 wherein said IOL comprises water in an amount of 20% to 30% by weight.

13. The preloaded intraocular lens system of claim 12 wherein said IOL comprises water in an amount of 24% to 27% by weight.

14. The preloaded intraocular lens system of claim 11 wherein said IOL comprises a UV absorber.

15. The preloaded intraocular lens system of claim 14 wherein said IOL comprises a yellow dye.

16. The preloaded intraocular lens system of claim 2 wherein said cartridge further comprises a lock mechanism for maintaining said IOL in a folded state.

17. The preloaded intraocular lens system of claim 2 wherein said injector further comprises an injector body that retains said cartridge in place and a plunger shaft further comprising a soft cushion connected to a plunger body.

18. The preloaded intraocular lens system of claim 17 wherein said plunger shaft is configured to be temporarily locked into said injector body in a pre-determined position.

19. The preloaded intraocular lens system of claim 1 wherein said lens holding chamber and said lumen are directly connected and are configured to allow said IOL to gradually decrease in profile as said IOL passes through said lumen.

20. The preloaded intraocular lens system of claim 19, wherein the haptic-to-haptic distance of said compressed IOL ranges from 7 mm to 12 mm.

21. The preloaded intraocular lens system of claim 20 wherein the haptic-to-haptic distance of said compressed IOL ranges from 9 mm to 11 mm.

22. The preloaded intraocular lens system of claim 19 wherein said IOL comprises a cross-linked hydrophobic acrylic polymer.

23. The preloaded intraocular lens system of claim 22 wherein said cross-linked hydrophobic polymer comprises a cross-linker in an amount of approximately 1% to 6% by weight.

24. The preloaded intraocular lens system of claim 23 wherein said IOL comprises a UV absorber.

25. The preloaded intraocular lens system of claim 24 wherein said IOL comprises a yellow dye.

26. The preloaded intraocular lens system of claim 19 wherein said IOL comprises a cross-linked hydrophilic acrylic polymer.

27. The preloaded intraocular lens system of claim 26 wherein said IOL comprises water in an amount of 20% to 30% by weight.

28. The preloaded intraocular lens system of claim 27 wherein said IOL comprises water in an amount of 24% to 27% by weight.

29. The preloaded intraocular lens system of claim 26 wherein said IOL comprises a UV absorber.

30. The preloaded intraocular lens system of claim 29 wherein said IOL comprises a yellow dye.

31. A method of placing an intraocular lens (IOL) with a preloaded intraocular lens system within an eye of a patient, the method comprising:
(1) providing a preloaded IOL system, said system including:
(a) an intraocular lens (IOL) defining an optical axis and a center plane perpendicular to said optical axis;
(b) a lens holding chamber;
(c) a lumen; and,
(d) an injector;
said IOL having C-shaped haptics;
each of said haptics having an attached end attached to said IOL and a free end;
said haptics being compressed so as to cause said haptics with said free ends thereof to be compressed and thereby wrapped around said IOL in said center plane with said free ends remaining coplanar with said IOL,
said free ends of said haptics remaining coplanar with said IOL during the entire loading of said IOL into and while in said lens holding chamber;
said lens holding chamber having mutually adjacent walls for holding said IOL therebetween so as to permit said IOL to be shipped and stored with said haptics in a compressed state after said loading of said IOL;
said IOL being held in said compressed state by elastic forces created by said compressed haptics; and,
said lumen having an input tube portion leading to a distal opening end;
(2) preloading said IOL within said lens holding chamber in said compressed state; and,
(3) activating a plunger to transport said compressed IOL through said lumen into the eye of said patient and placing said IOL within said eye.

32. The method of claim 31 wherein said lens holding chamber and said lumen are components of a cartridge and wherein said lens holding chamber has internal rails on which said IOL rests.

33. The method of claim 32 wherein said cartridge further comprises a hinge having wings, said wings being configured to be opened for receiving said IOL or closed for folding said IOL.

34. The method of claim 33 wherein said cartridge is configured such that when said IOL is positioned in said rails the central portion of said IOL does not touch the hinge of said cartridge.

35. The method of claim 32 wherein the haptic-to-haptic distance of said compressed IOL ranges from 7 mm to 12 mm.

36. The method of claim 35 wherein the haptic-to-haptic distance of said compressed IOL ranges from 9 mm to 11 mm.

37. The method of claim 32 wherein said IOL comprises a cross-linked hydrophobic acrylic polymer.

38. The method of claim 37 wherein said cross-linked hydrophobic polymer comprises a cross-linker in an amount of approximately 1% to 6% by weight.

39. The method of claim 38 wherein said IOL comprises a UV absorber.

40. The method of claim 39 wherein said IOL comprises a yellow dye.

41. The method of claim 32 wherein said IOL comprises a cross-linked hydrophilic acrylic polymer.

42. The method of claim 41 wherein said IOL comprises water in an amount of 20% to 30% by weight.

43. The method of claim 42 wherein said IOL comprises water in an amount of 24% to 27% by weight.

44. The method of claim 41 wherein said IOL comprises a UV absorber.

45. The method of claim 44 wherein said IOL comprises a yellow dye.

46. The method of claim 32 wherein said cartridge further comprises a lock mechanism for maintaining said IOL in a folded state.

47. The method of claim 32 wherein said injector further comprises an injector body that retains said cartridge in place and a plunger shaft further comprising a soft cushion connected to a plunger body.

48. The method of claim 47 wherein said plunger is configured to be temporarily locked into said injector body in a pre-determined position.

49. The method of claim 31 wherein said lens holding chamber and said lumen are directly connected and are configured to allow said IOL to gradually decrease in profile as said IOL passes through said lumen.

50. The method of claim 49, wherein the haptic-to-haptic distance of said compressed IOL ranges from 7 mm to 12 mm.

51. The method of claim 50 wherein the haptic-to-haptic distance of said compressed IOL ranges from 9 mm to 11 mm.

52. The method of claim 49 wherein said IOL comprises a cross-linked hydrophobic acrylic polymer.

53. The method of claim 52 wherein said cross-linked hydrophobic polymer comprises a cross-linker in an amount of approximately 1% to 6% by weight.

54. The method of claim 53 wherein said IOL comprises a UV absorber.

55. The method of claim 54 wherein said IOL comprises a yellow dye.

56. The method of claim 49 wherein said IOL comprises a cross-linked hydrophilic acrylic polymer.

57. The method of claim 56 wherein said IOL comprises water in an amount of 20% to 30% by weight.

58. The method of claim 57 wherein said IOL comprises water in an amount of 24% to 27% by weight.

59. The method of claim 56 wherein said IOL comprises a UV absorber.

60. The method of claim 59 wherein said IOL comprises a yellow dye.

* * * * *